(12) United States Patent
Phan et al.

(10) Patent No.: US 6,753,415 B2
(45) Date of Patent: Jun. 22, 2004

(54) 23-O-SUBSTITUTED 5-O-MYCAMINOSYLTYLONIDE DERIVATIVES

(75) Inventors: Ly Tam Phan, Malden, MA (US); Yao-Ling Qiu, Somerville, MA (US); Yat Sun Or, Cambridge, MA (US); Nha Vo, Malden, MA (US); Tianying Jian, Boston, MA (US); Ying Hou, Everett, MA (US); Marina Busuyek, Natick, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/126,076

(22) Filed: Apr. 19, 2002

(65) Prior Publication Data

US 2003/0212010 A1 Nov. 13, 2003

(51) Int. Cl.[7] ..................... A61K 31/7048; C07H 17/08

(52) U.S. Cl. .......................... 536/7.1; 536/7.4; 514/28; 514/29

(58) Field of Search ................... 536/7.1, 7.4; 424/180; 514/29, 28

(56) References Cited

U.S. PATENT DOCUMENTS

| | | | |
|---|---|---|---|
| 4,436,729 A | * | 3/1984 | Ganguly et al. ............ 424/180 |
| 4,468,511 A | | 8/1984 | Kirst et al. ................... 536/7.1 |
| 4,629,786 A | | 12/1986 | Debono et al. .............. 536/7.1 |

FOREIGN PATENT DOCUMENTS

| | | | |
|---|---|---|---|
| EP | 0099747 A1 | 2/1984 | ........... C07H/17/08 |
| EP | 0100645 A1 | 2/1984 | ........... C07H/17/08 |
| EP | 0627443 A1 | 12/1994 | ........... C07H/17/08 |
| WOPCT/IB | WO 95/02594 | 1/1995 | ......... C07D/407/12 |
| WO | WO 03/011882 A1 | 2/2003 | ........... C07H/17/08 |

OTHER PUBLICATIONS

Kirst, Herbert A. "Synthesis and Evaluation of Tylosin–Related Macrolides Modified at the Aldehyde Function: A New Series of Oraly Effective Antibiotics", Journal of Medicinal Chemistry, 1988, 31(8), 1631–41.*

Omura, S. "Ribosome–binding activities and antimicrobial activities of tylosin and its related compounds", Journal of Antibiotics, 1983, 36(12), 1709–12.*

Willard, Kevin E. et al "Identification and Synthesis of an Oxidation Product of Tilmicosin", Journal of Agricultural and Food Chemistry, 1988, 46(8), 3265–71).*

A. Tanaka et al.: "Synthesis of Recyclized Macrolide Antibiotics and related Derivatives from Mycaminosyltylonolide." Bulletin of the Chemical Society of Japan, vol. 54, No. 12. 1981. pp. 3837–3845. XP008019387 p. 3837. compound 1.

Kirst et al.: "Synthesis and Antimicrobial Evaluation of Acyl Derivatives of 16–Membered Macrolide Antibiotics Related to Tylosin." Journal of Antibiotics vol. 39, No. 8, 1986, pp. 1108–1122, XP001149216.

Kirst et al.: "Preparation and Evaluation of 3,4–Ester Derivatives of 16–Membered Macrolide Antibiotics Related to Tylosin." Journal of Antibiotics, vol. 39, No. 12, 1986, pp. 1724–1735, XP001149217.

Annex to Form PCT/ISA/206 Communication Relating to the Results of the Partial International Search for International Application No.: PCT/US 03/12211, Jul. 24, 2003.

* cited by examiner

*Primary Examiner*—Ganapathy Krishnan
(74) *Attorney, Agent, or Firm*—Jason D. Ferrone

(57) ABSTRACT

There are described novel 5-O-mycaminosyltylonide (OMT) analogs possessing increased antibacterial activity toward Gram positive and Gram negative bacteria as well as macrolide resistant Gram positives and pharmaceutically acceptable compositions comprising a therapeutically effective amount of a compound of the invention in combination with a pharmaceutically acceptable carrier. Also described are a method for treating bacterial infections by administering to a patient a pharmaceutical composition containing a therapeutically-effective amount of a compound of the invention, and processes for the preparation of such compounds

15 Claims, No Drawings

23-O-SUBSTITUTED 5-O-MYCAMINOSYLTYLONIDE DERIVATIVES

REFERENCE TO RELATED APPLICATION

Reference is made to copending, commonly assigned U.S. patent application Ser. No. 10/125,840, filed on even date herewith.

TECHNICAL FIELD

The present invention relates to novel macrolides having antibacterial activity and useful in the treatment and prevention of bacterial infections. More particularly, the invention relates to a novel class of 4'-substituted 16-membered macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic families (14-, 15- and 16-membered ring derivatives) exhibit a wide range of characteristics (antibacterial spectrum, side-effects and bioavailability). Among the commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type). Sixteen membered macrolides usually contain an amino-disaccharide-4-O-(L-mycarosyl)-D-mycaminose and/or D-desosamine. One class has only neutral sugars. The sixteen membered macrolides can be classified into two major groups—the leucomycins and the tylosin series.

The tylosin series is divided into two groups—IIA and IIB—which differ at the C-6-side chain and the nature of the sugars on the chromophore. Tylosin consists of a substituted 16-membered ring lactone (tylonolide), an aminosugar (D-mycaminose) attached to C-5, two neutral sugars (D-mycinose attached at C-23 and L-mycarose attached at C-4') and an acetaldehyde at C-6.

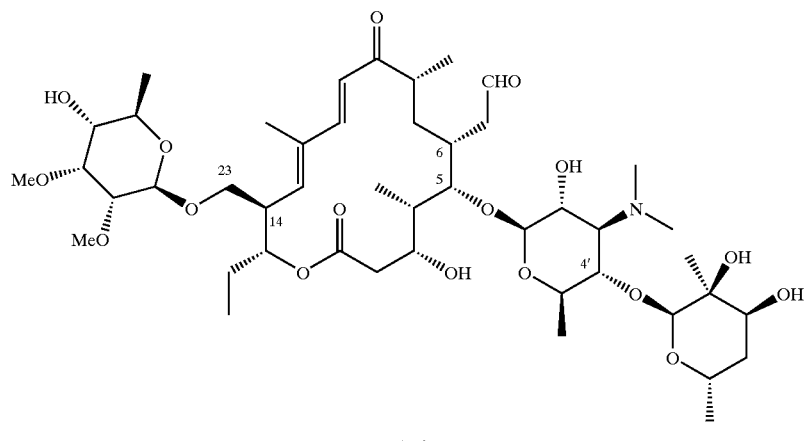

Tylosin

Considerable research efforts have been carried out on tylosin and its derivatives but not much success has been observed with this subclass. The search for macrolides active against $MLS_B$-resistant strains ($MLS_B$=Macrolides-Lincosamides-Type B Streptogramines) has become a major goal, in addition to improving the overall profile of the macrolides in terms of acid stability, tolerance and pharmacokinetics.

SUMMARY OF THE INVENTION

The present invention provides a novel class of 5-O-mycaminosyltylonide (OMT) analogs possessing increased antibacterial activity toward Gram positive and Gram negative bacteria as well as macrolide resistant Gram positives. In addition, the present invention provides a class of 5-O-mycaminosyltylonide analogs that are more acid stable and overcome bacterial resistance.

In one embodiment, the present invention provides compounds represented by Formula I, or a pharmaceutically acceptable salt, ester or prodrug thereof:

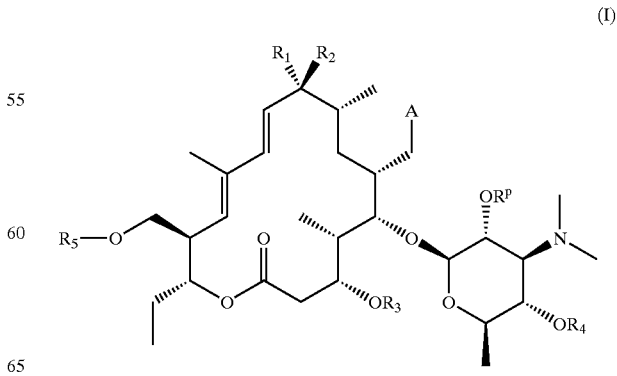

(I)

In Formula I

A is selected from the group consisting of:
(1) —CHO or a protected aldehyde;
(2) —CN;
(3) —CH=N—NR$_6$R$_7$, wherein R$_6$ and R$_7$ are each independently selected from the group consisting of:
   (a) hydrogen;
   (b) C$_1$–C$_6$-alkyl, optionally substituted with one or more substituents selected from the group consisting of: halogen, aryl, substituted aryl, heterocyclic, and substituted heterocyclic;
   (c) C$_2$–C$_6$-alkenyl, optionally substituted with one or more substituents selected from the group consisting of: halogen, aryl, substituted aryl, heterocyclic, and substituted heterocyclic;
   (d) C$_2$–C$_6$-alkynyl, optionally substituted with one or more substituents selected from the group consisting of: halogen, aryl, substituted aryl, heterocyclic, and substituted heterocyclic; and
   (e) R$_6$ and R$_7$, taken together with the nitrogen atom to which they are connected, form a 3- to 7-membered ring which may optionally contain a hetero-function selected from the group consisting of: —O—, —NH—, —N(C$_1$–C$_6$-alkyl)-, —N(aryl)-, —N(heteroaryl)-, —S—, —S(O)—, and —S(O)$_2$—;
(4) —CH=N—OR$_6$, where R$_6$ is as previously defined;
(5) —CH$_2$X, wherein X is selected from the group consisting of:
   (a) hydroxy or protected hydroxy;
   (b) halogen;
   (c) —NR$_6$R$_7$, where R$_6$ and R$_7$ are as previously defined;
   (d) —NR$_6$C(O)—R$_8$, where R$_6$ is as previously defined and R$_8$ is selected from the group consisting of:
      i. hydrogen;
      ii. C$_1$–C$_6$-alkyl, optionally substituted with one or more substituents selected from the group consisting of: halogen, aryl, substituted aryl, heterocyclic, and substituted heterocyclic;
      iii. C$_2$–C$_6$-alkenyl, optionally substituted with one or more substituents selected from the group consisting of: halogen, aryl, substituted aryl, heterocyclic, and substituted heterocyclic;
      iv. C$_2$–C$_6$-alkynyl, optionally substituted with one or more substituents selected from the group consisting of: halogen, aryl, substituted aryl, heterocyclic, and substituted heterocyclic;
      v. aryl;
      vi. substituted aryl;
      vii. heterocyclic; and
      viii. substituted heterocyclic;
   (e) —NR$_6$C(O)—NR$_7$R$_8$, where R$_6$, R$_7$, and R$_8$ are as previously defined;
   (f) —NR$_6$—NR$_7$R$_8$, where R$_6$, R$_7$ and R$_8$ are as previously defined;
   (g) —NR$_6$—NR$_7$C(O)—R$_8$, where R$_6$, R$_7$ and R$_8$ are as previously described;
   (h) —S(O)$_n$—R$_9$, where R$_9$ is selected from the group consisting of: aryl, substituted aryl, heterocyclic, and substituted heterocyclic, where n is 0, 1 or 2;
   (i) —S(O)$_n$—(C$_1$–C$_6$-alkyl), optionally substituted with one or more substituents selected from the group consisting of: aryl, substituted aryl, heterocyclic, and substituted heterocyclic, where n is as previously defined;
   (j) —S(O)$_n$—(C$_2$–C$_6$-alkenyl), optionally substituted with one or more substituents selected from the group consisting of: aryl, substituted aryl, heterocyclic, and substituted heterocyclic, where n is as previously defined;
   (k) —S(O)$_n$—(C$_2$–C$_6$-alkynyl), optionally substituted with one or more substituents selected from the group consisting of: aryl, substituted aryl, heterocyclic, and substituted heterocyclic, where n is as previously defined; and
   (l) —O—M—Y, where M is:
      i. absent,
      ii. —C(O)—,
      iii. —C(O)N(R$_6$)—, where R$_6$ is as previously defined,
      iv. C$_1$–C$_6$-alkyl-N(R$_6$)—, where R$_6$ is as previously defined,
      v. C$_2$–C$_6$-alkenyl-N(R$_6$)—, where R$_6$ is as previously defined, or
      vi. C$_2$–C$_6$-alkynyl-N(R$_6$)—, where R$_6$ is as previously defined,
      and where Y is:
      i. hydrogen,
      ii. C$_1$–C$_6$-alkyl, optionally substituted with one or more substituents selected from the group consisting of: halogen, —OR$_6$, aryl, substituted aryl, heterocyclic, and substituted heterocyclic, where R$_6$ is as previously defined,
      iii. C$_2$–C$_6$-alkenyl, optionally substituted with one or more substituents selected from the group consisting of: halogen, —OR$_6$, aryl, substituted aryl, heterocyclic, and substituted heterocyclic, where R$_6$ is as previously defined,
      iv. C$_2$–C$_6$-alkynyl, optionally substituted with one or more substituents selected from the group consisting of: halogen, —OR$_6$, aryl, substituted aryl, heterocyclic, and substituted heterocyclic, where R$_6$ is as previously defined,
      v. aryl,
      vi. substituted aryl,
      vii. heterocyclic, or
      viii. substituted heterocyclic;
(6) heterocyclic or substituted heterocyclic;

R$_1$ and R$_2$ are each independently selected from the group consisting of:
(1) hydrogen;
(2) hydroxy;
(3) protected hydroxy;
(4) —OC(O)—C$_1$–C$_{12}$-alkyl, optionally substituted with one or more substituents selected from the group consisting of: halogen, aryl, substituted aryl, heterocyclic, substituted heterocyclic, —OR$_6$, and —NR$_6$R$_7$, where R$_6$ and R$_7$ are as previously defined;
(5) —OR$_6$, where R$_6$ is as previously defined;
(6) halogen;
(7) —NR$_6$R$_7$, where R$_6$ and R$_7$ are as previously defined; and
(8) R$_1$ and R$_2$ taken together are=O;

R$_3$ is selected from the group consisting of:
(1) hydrogen;
(2) a hydroxy protecting group;

(3) —C(O)—$C_1$–$C_{12}$-alkyl, optionally substituted with one or more substituents selected from the group consisting of: halogen, aryl, substituted aryl, heterocyclic, substituted heterocyclic, —$OR_6$, and —$NR_6R_7$, where $R_6$ and $R_7$ are as previously defined;

(4) $C_1$–$C_6$-alkyl, optionally substituted with one or more substituents selected from the group consisting of: halogen, aryl, substituted aryl, heterocyclic, substituted heterocyclic, —$OR_6$, and —$NR_6R_7$, where $R_6$ and $R_7$ are as previously defined;

(5) $C_2$–$C_6$-alkenyl, optionally substituted with one or more substituents selected from the group consisting of: halogen, aryl, substituted aryl, heterocyclic, substituted heterocyclic, —$OR_6$, and —$NR_6R_7$, where $R_6$ and $R_7$ are as previously defined; and (6) $C_2$–$C_6$-alkynyl, optionally substituted with one or more substitutents selected from the group consisting of: halogen, aryl, substituted aryl, heterocyclic, substituted heterocyclic, —$OR_6$, and —$NR_6R_7$, where $R_6$ and $R_7$ are as previously defined;

$R_4$ is —M—Y, where M and Y are as previously defined;

$R_5$ is —M—Y, where M and Y are as previously defined; and $R^P$ is hydrogen or a hydroxy protecting group.

In another embodiment, the present invention provides a process for preparing novel compounds represented by Formula I wherein the groups A, $R_1$, $R_2$, $R_3$, $R_4$, $R_5$ and $R^P$ are as previously defined.

DETAILED DESCRIPTION

A first embodiment of the invention is a compound represented by Formula I as described above.

Representative compounds of the invention are those selected from the group consisting of:

Compound of Formula I: A=—CHO, $R_1$ and $R_2$ taken together are=O, $R_3$=H, $R_4$=H, $R_5$=4-quinoline-carboxyl and $R^P$=H;

Compound of Formula I; A=—CHO, $R_1$ and $R_2$ taken together are=O, $R_3$=H, $R_4$=H, $R_5$=3-pyridyl-acetyl and $R^P$=H;

Compound of Formula I: A=—CHO, $R_1$ and $R_2$ taken together are=O, $R_3$H, $R_4$=H, $R_5$=3-pyridine-propionyl and $R^P$=H;

Compound of Formula I: A=—CHO, $R_1$ and $R_2$ taken together are=O, $R_3$=H, $R_4$=H, $R_5$=3-pyridine-acrylyl and $R^P$=H;

Compound of Formula I: A=—CHO, $R_1$ and $R_2$ taken together are=O, $R_3$=H, $R_4$=H, $R_5$=C(O)$NH_2$ and $R^P$=H;

Compound of Formula I: A=—CHO, $R_1$ and $R_2$ taken together are=O, $R_3$=H, $R_4$=H, $R_5$=C(O)NHPhenyl and $R^P$=H;

Compound of Formula I: A=—CHO, $R_1$ and $R_2$ taken together are=O, $R_3$=H, $R_4$=H, $R_5$=C(O)NH-p-tolyl and $R^P$=H;

Compound of Formula I: A=—CHO, $R_1$ and $R_2$ taken together are=O, $R_3$=H, $R_4$=H, $R_5$=C(O)NH-4-methylthiophenyl and $R^P$=H;

Compound of Formula I: A=—CHO, $R_1$ and $R_2$ taken together are=O, $R_3$=H, $R_4$=H, $R_5$=C(O)NH-4-methoxyphenyl and $R^P$=H;

Compound of Formula I: A=—CHO, $R_1$ and $R_2$ taken together are=O, $R_3$=H, $R_4$=H, $R_5$=C(O)NH-4-dimethylaminophenyl and $R^P$=H;

Compound of Formula I: A=—CHO, $R_1$ and $R_2$ taken together are=O, $R_3$=H, $R_4$=H, $R_5$=C(O)NH-4-phenoxyphenyl and $R^P$=H;

Compound of Formula I: A=—CHO, $R_1$ and $R_2$ taken together are=O, $R_3$=H, $R_4$=H, $R_5$=C(O)NH-4-cyanophenyl and $R^P$=H;

Compound of Formula I: A=—CHO, $R_1$ and $R_2$ taken together are=O, $R_3$=H, $R_4$=H, $R_5$=C(O)NH-4-nitrophenyl and $R^P$=H;

Compound of Formula I: A=—CHO, $R_1$ and $R_2$ taken together are=O, $R_3$=H, $R_4$=H, $R_5$=C(O)NH-α,α,α-trifluoro-p-tolyl and $R^P$=H;

Compound of Formula I: A=—CHO, $R_1$ and $R_2$ taken together are=O, $R_3$=H, $R_4$=H, $R_5$=C(O)NH-4-fluoro-3-nitrophenyl and $R^P$=H;

Compound of Formula I: A=—CHO, $R_1$ and $R_2$ taken together are=O, $R_3$=H, $R_4$=H, $R_5$=C(O)NH-3,4-difluorophenyl and $R^P$=H;

Compound of Formula I: A=—CHO, $R_1$ and $R_2$ taken together are=O, $R_3$=H, $R_4$=H, $R_5$=C(O)NH-3,5-difluorophenyl and $R^P$=H;

Compound of Formula I: A=—CHO, $R_1$ and $R_2$ taken together are=O, $R_3$=H, $R_4$=H, $R_5$=C(O)NH-4-acetylphenyl and $R^P$=H;

Compound of formula I: A=—CHO, $R_1$ and $R_2$ taken together are=O, $R_3$=H, $R_4$=H, $R_5$=C(O)NH-(4-fluoro)phenyl and $R^P$=H;

Compound of Formula I: A=—CHO, $R_1$ and $R_2$ taken together are=O, $R_3$=H, $R_4$=H, $R_5$=C(O)NH-(4-chloro)phenyl and $R^P$=H;

Compound of Formula I: A=—CHO, $R_1$ and $R_2$ taken together are=O, $R_3$=H, $R_4$=H, $R_5$=C(O)NH-(4-bromo)phenyl and $R^P$=H;

Compound of Formula I: A=—CHO, $R_1$ and $R_2$ taken together are=O, $R_3$=H, $R_4$=H, $R_5$=C(O)NH$CH_2$Phenyl and $R^P$=H;

Compound of Formula I: A=—CHO, $R_1$ and $R_2$ taken together are=O, $R_3$=H, $R_4$=H, $R_5$=C(O)NH$CH_2CH_2$Phenyl and $R^P$=H;

Compound of Formula I: A=—CHO, $R_1$ and $R_2$ taken together are=O, $R_3$=H, $R_4$=H, $R_5$=C(O)NH$CH_2CH_2$Br and $R^P$=H;

Compound of Formula I: A=—CHO, $R_1$ and $R_2$ taken together are=O, $R_3$=H, $R_4$=H, $R_5$=C(O)NH$CH_2$CH$CH_2$ and $R^P$=H;

Compound of Formula I: A=—CHO, $R_1$ and $R_2$ taken together are=O, $R_3$=H, $R_4$=H, $R_5$=C(O)NH$CH_2$CHCH-3-quinolyl and $R^P$=H;

Compound of Formula I: A=—CHO, $R_1$ and $R_2$ taken together are=O, $R_3$=H, $R_4$=H, $R_5$=$CH_2OCH_3$ and $R^P$=H;

Compound of Formula I: A=—CHO, $R_1$ and $R_2$ taken together are=O, $R_3$=H, $R_4$=H, $R_5$=$CH_2OCH_2$Phenyl and $R^P$=H;

Compound of Formula I: A=—CHO, $R_1$ and $R_2$ taken together are=O, $R_3$=$CH_2OCH_2$Phenyl, $R_4$=H, $R_5$=$CH_2OCH_2$Phenyl and $R^P$=H;

Compound of Formula I: A=—CHO, $R_1$ and $R_2$ taken together are=O, $R_3$=H, $R_4$=H, $R_5$=$CH_3$ and $R^P$=H;

Compound of Formula I: A=—CHO, $R_1$ and $R_2$ taken together are=O, $R_3$=H, $R_4$=H, $R_5$=$CH_2$CCH and $R^P$=H;

Compound of Formula I: A=—CHO, $R_1$ and $R_2$ taken together are=O, $R_3$=H, $R_4$=H, $R_5$=$(CH_2)_4$Br and $R^P$=H;

Compound of Formula I: A=—CHO, $R_1$ and $R_2$ taken together are=O, $R_3$=H, $R_4$=H, $R_5$=CH$_2$CHCHCH$_2$Cl and $R^P$=H;

Compound of Formula I: A=—CHO, $R_1$ and $R_2$ taken together are=O, $R_3$=H, $R_4$=H, $R_5$=CH$_2$Phenyl and $R^P$=H;

Compound of Formula I: A=—CHO, $R_1$ and $R_2$ taken together are=O, $R_3$=H, $R_4$=H, $R_5$=CH$_2$CHCH$_2$ and $R^P$=H;

Compound of Formula I: A=—CHO, $R_1$ and $R_2$ taken together are=O, $R_3$=CH$_2$CHCH$_2$, $R_4$=H, $R_5$=CH$_2$CHCH$_2$ and $R^P$=H;

Compound of Formula I: A=—CHO, $R_1$ and $R_2$ taken together are=O, $R_3$=H, $R_4$=H, $R_5$=CH$_2$CHCH-(3-quinolyl) and $R^P$=H;

Compound of Formula I: A=—CHO, $R_1$ and $R_2$ taken together are=O, $R_3$=H, $R_4$=CH$_2$CHCH-(3-quinolyl) and $R^P$=H;

Compound of Formula I: A=CHO, $R_1$ and $R_2$ taken together are=O, $R_3$=H, $R_4$=(t-butoxycarboxy)-3-(3-quinolyl), $R_5$=CH$_2$-phenyl, and $R^P$=H;

Compound of Formula I: A=CHO, $R_1$ and $R_2$ taken together are=O, $R_3$=H, $R_4$=CH$_2$CHCH$_2$, $R_5$=H and $R^P$=H;

Compound of Formula I: A=CHO, $R_1$ and $R_2$ taken together are=O, $R_3$=H, $R_4$=CHCHCH$_2$-3-quinolyl, $R_5$=H and $R^P$=H;

Compound of Formula I: A=CHO, $R_1$ and $R_2$ taken together are=O, $R_3$=H, $R_4$=CHCHCH$_2$-3-quinolyl, $R_5$=—C(O)NH-Phenyl and $R^P$=H;

Compound of Formula I: A=CHO, $R_1$ and $R_2$ taken together are=O, $R_3$=H, $R_4$=CH$_3$, $R_5$=H and $R^P$=H;

Compound of Formula I: A=CHO, $R_1$ and $R_2$ taken together are=O, $R_3$=H, $R_4$=CH$_2$-phenyl, $R_5$=H and $R^P$=H;

Compound of Formula I: A=CHO, $R_1$ and $R_2$ taken together are=O, $R_3$=H, $R_4$=CH$_2$-phenyl, $R_5$=H and $R^P$=H;

Compound of Formula I: A=CHO, $R_1$ and $R_2$ taken together are=O, $R_3$=H, $R_4$=CH$_2$CCH, $R_5$=CH$_3$ and $R^P$=H;

Compound of Formula I: A=CHO, $R_1$ and $R_2$ taken together are=O, $R_3$=H, $R_4$=2-fluoro-3-nitrobenzyl, $R_5$=CH$_3$ and $R^P$=H;

Compound of Formula I: A=CHO, $R_1$ and $R_2$ taken together are=O, $R_3$=H, $R_4$=(2-pyridyl)thiophenyl, $R_5$=CH$_3$ and $R^P$=H;

Compound of Formula I: A=CHO, $R_1$ and $R_2$ taken together are=O, $R_3$=H, $R_4$=CH$_2$CC-(3-quinolyl), $R_5$=CH$_3$ and $R^P$=H;

Compound of Formula I: A=CHO, $R_1$ and $R_2$ taken together are=O, $R_3$=H, $R_4$=CH$_2$CC-(3-pyrimidyl), $R_5$=CH$_3$ and $R^P$=H;

Compound of Formula I: A=CHO, $R_1$ and $R_2$ taken together are=O, $R_3$=H, $R_4$=CH$_2$CC-(3-pyridinyl), $R_5$=CH$_3$ and $R^P$=H;

Compound of Formula I: A=CHO, $R_1$ and $R_2$ taken together are=O, $R_3$=H, $R_4$=CH$_2$CHCH-(3-pyrimidinyl), $R_5$=CH$_3$ and $R^P$=H; and Compound of Formula I: A=CHO, $R_1$ and $R_2$ taken together are=O, $R_3$=H, $R_4$=CH$_2$CH$_2$CH$_2$-(3-pyrimidinyl), $R_5$=CH$_3$ and $R^P$=H.

Definitions

The terms "$C_1$–$C_3$-alkyl," "$C_1$–$C_6$-alkyl" or "$C_1$–$C_{12}$-alkyl," as used herein, refer to saturated, straight- or branched-chain hydrocarbon radicals containing between one and three, one and six or one and twelve carbon atoms, respectively. Examples of $C_1$–$C_3$ alkyl radicals include, but are not limited to, methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl, and examples of $C_1$–$C_{12}$-alkyl radicals include, but are not limited to, methyl, ethyl, propyl, isopropyl, n-butyl, tert-butyl, neopentyl, n-hexyl, n-octyl, n-decyl, and n-dodecyl.

The term "$C_2$–$C_6$-alkenyl," as used herein, refers to straight- or branched-chain hydrocarbon radicals containing between two and six carbon atoms with one or more double bonds in the chain. Examples of $C_2$–$C_6$-alkenyl include, but are not limited to, propenyl, isobutenyl, 1,3-hexadienyl, n-hexenyl, and 3-pentenyl.

The term "$C_2$–$C_6$-alkynyl," as used herein, refers to straight- or branched-chain hydrocarbon radicals containing between two and six carbon atoms with one or more triple bonds in the chain optionally containing one or more double bond. Examples of $C_2$–$C_6$-alkynyl include, but are not limited to, propynyl, isopentynyl, 1,3-hexadienyl, n-hexynyl, 3-pentynyl, and 1-hexen-3-ynyl.

The term "$C_1$–$C_6$-alkoxy," as used herein, refers to a $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "aprotic solvent," as used herein, refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methyl pyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl," as used herein, refers to unsubstituted carbocyclic aromatic groups including, but not limited to, phenyl, 1- or 2-naphthyl and the like.

The terms "$C_3$–$C_5$-cycloalkyl- and $C_3$–$C_7$-cycloalkyl," as used herein refer to carbocyclic groups of 3 to 5 or 3 to 7 carbon atoms, respectively, such as for example, cyclopropyl, cyclobutyl, cyclopentyl, cyclohexyl, and cycloheptyl.

The term "$C_1$–$C_3$-alkyl-$C_3$–$C_5$-cycloalkyl," as used herein refers to a $C_3$–$C_5$-cycloalkyl radical, as defined above, attached to a $C_1$–$C_3$-alkyl radical by replacement of a hydrogen atom on the latter.

The terms "halo" and "halogen," as used herein, refer to an atom selected from fluorine, chlorine, bromine and iodine.

The term "heteroaryl," as used herein, refers to a cyclic aromatic radical having from five to ten ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic," as used herein, refers to heterocycloalkyl and heteroaryl. The term "substituted heterocyclic," as used herein, refers to substituted heterocycloalkyl and substituted heteroaryl.

The term "substituted aryl," as used herein refers to an aryl group, as defined herein, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_7$-cycloalkyl, $CF_3$, $CH_2CF_3$, $CH_2C_2$, $CH_2OH$, $CH_2CH_2OH$, $CH_2NH_2$, $CH_2SO_2CH_3$, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl," as used herein refers to a heteroaryl group as defined herein substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, NHCONH-heteroaryl, $SO_2$—$C_1$–$C_6$-alkyl, NHCONH-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl," as used herein, refers to a heterocycloalkyl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted cycloalkyl," as used herein, refers to a $C_3$–$C_7$ cycloalkyl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_{c6}$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

"Hydroxy-protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, Protective Groups in Organic Synthesis, 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy," refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group," as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G. M, Wuts, Protective Groups in Organic Synthesis, op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, 1,3-dioxolane, 1,3-dioxane and the like.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of protogenic solvents may be found in organic chemistry textbooks or in specialized monographs, for example: Organic Solvents Physical Properties and Methods of Purification, 4th ed., edited by John A. Riddick et al., op. cit.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL)

by use of a 96 fixed tip-pipetting station. The inoculum for each bacterial strain was standardized to $5\times10^5$ CFU/mL by optical comparison to a 0.5 McFarland turbidity standard. The plates were inoculated with 10 μl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 μg/ml to about 0.03 μg/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of the compounds of the present invention per day in single or multiple doses.

Synthetic Methods

The compounds and processes of the present invention will be better understood in connection with the following synthetic schemes which are illustrative of the methods by which the compounds of the invention may be prepared. The groups A, $R_1$, $R_2$, $R_3$, $R_4$, $R_5$, $R_6$, $R_7$, $R_8$, $R_9$, and $R^p$ are as defined previously, and unless otherwise noted below.

Abbreviations

Abbreviations which have been used in the descriptions of the scheme and the examples that follow are: Ac for acetyl; AIBN for azobisisobutyronitrile; BSA for bis(trimethylsilyl)acetamide; $Bu_3SnH$ for tributyltin hydride; Bz for benzoyl; CDI for carbonyldiimidazole; DBU for 1,8-diazabicyclo[5.4.0]undec-7-ene; DCC for 1,3-dicyclohexylcarbodiimide; DEAD for diethylazodicarboxylate; DIEA for diisopropylethylamine; DMAP for 4-N,N-dimethylamino-pyridine; DMF for dimethyl formamide; DMSO for dimethyl sulfoxide; DPPA for diphenylphosphoryl azide; EtOAc for ethyl acetate; HMDS for hexamethyldisilazane; KHMDS for potassium bis(trimethylsilyl)amide; MeOH for methanol; $NaN(TMS)_2$ for sodium bis(trimethylsilyl)amide; NMO for N-methylmorpholine N-oxide; PCC for pyridinium chlorochromate; PDC for pyridinium dichromate; TBAF for tetrabutylammonium fluoride; TBDMS for tert-butyldimethylsilyl; TBDP for tert-butylchloro-diphenyl; TBDPS for tert-butyldiphenylsilyl; TEA for triethylamine; TEA for trifluoroacetic acid; THF for tetrahydrofuran; TMS for trimethylsilyl and TPP for triphenylphosphine.

Scheme 1.
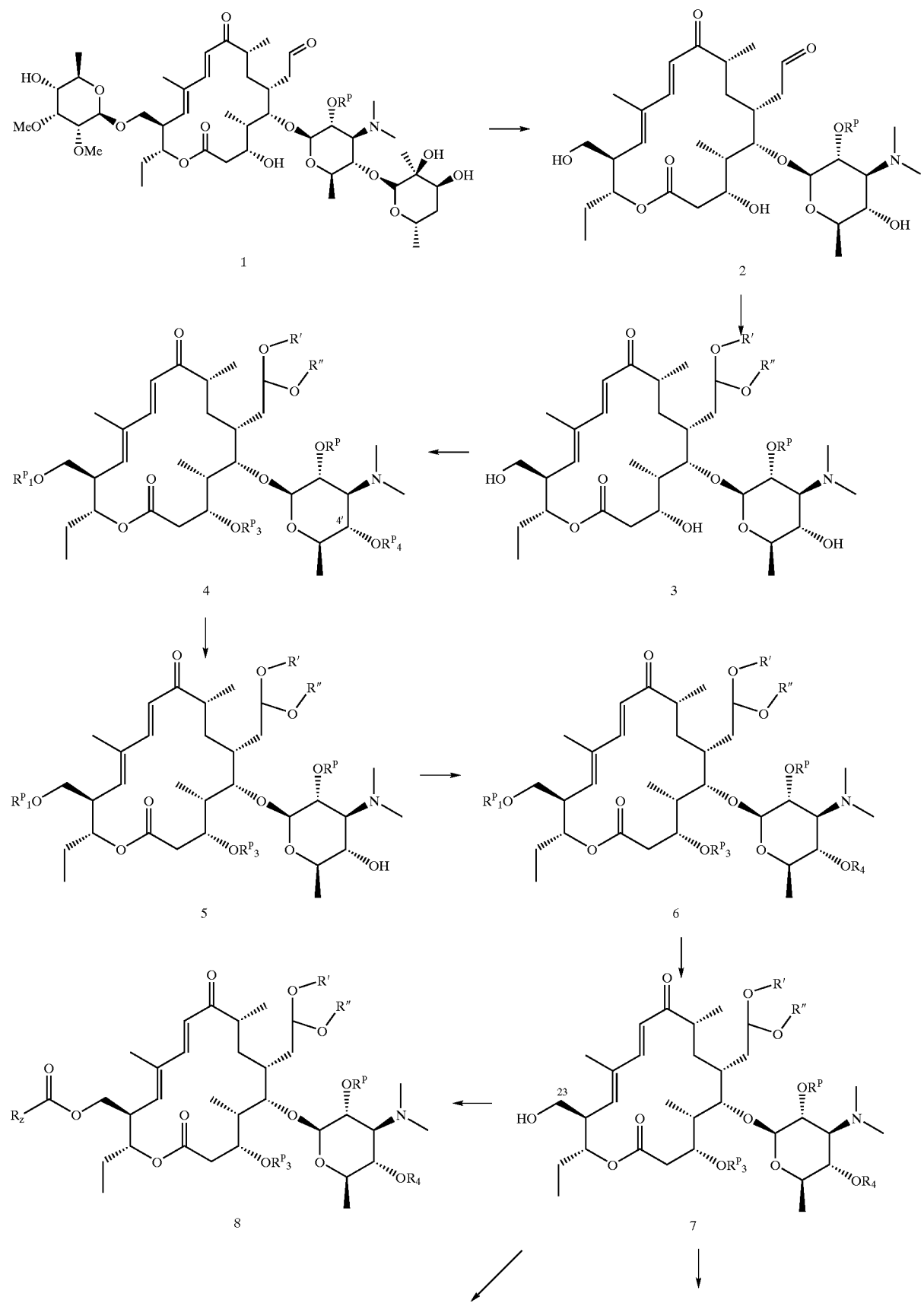

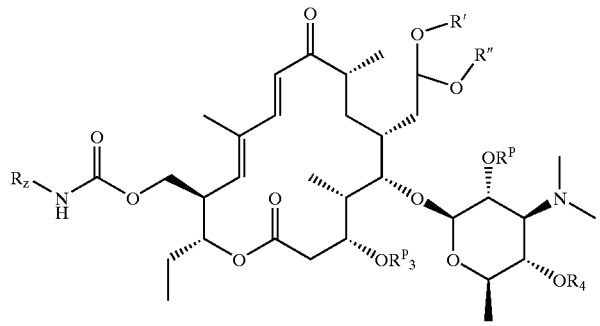

9

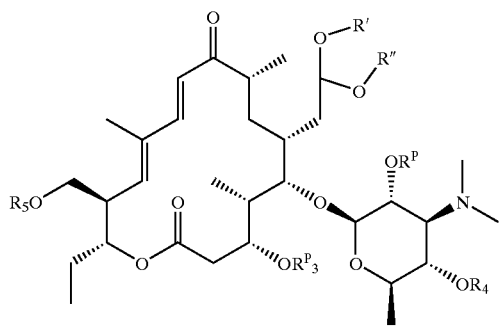

10

One synthetic method of the present invention pertaining to the preparation of the compounds of Formula I is illustrated in scheme 1. In scheme 1, 2'-protected tylosin (1 of scheme 1, where $OR^P$ is an ester) is treated with dilute aqueous acids (0.1–5N), such as hydrochloric acid, sulfuric acid, p-toluenesulfonic acid, 10-camphorsulfonic acid, trifluoroacetic acid, acetic acid, or the like, optionally in an organic solvent such as acetone, acetonitrile, methanol, ethanol, or the like, or combinations thereof, at a temperature from about 0° C. to about 100° C. for 0.5–24 hours, to provide protected 2 where $OR^P$ is an ester. 2 is treated with acetyl chloride, hydrochloric acid, p-toluenesulfonic acid, 10-camphorsulfonic acid, acetic acid, or the like, to provide a pH from about 1 to about 4 in an alcoholic solvent, such as methanol, ethanol, ethylene glycol, or the like, to provide an acetal 3, where R' and R" are independently or together alkyl, alkenyl or alkynyl. 3 is further treated with a silylating agent such as HMDS, BSA, TMSCl, triethylsilyl chloride, TBDMSCl, TBDPSCl, or the like, optionally with the addition of a catalyst such as, DMAP, imidazole, or the like, in an aprotic solvent such as methylene chloride, ethylene chloride, THF, chloroform, DMF, acetonitrile, or the like, at a temperature from about 0° C. to about 50° C. for 1–48 hours, to provide 4, where $R^P_1$ and $R^P_3$ are hydroxy protecting groups. Selective deprotection at 4' is achieved by treating 4 with an acid such as acetic acid, propanoic acid or phenolic acid, and the like, in an organic solvent such as acetone, acetonitrile, methanol, ethanol, or the like, or combinations thereof, at a temperature from about −20° C. to about 100° C. for 1–24 hours, to provide 5. 5 can be alkylated by an alkylating agent such as an alkyl halide, alkyl sulphonate, alkynyl halide, alkenyl halide, arylallyl halide, heteroarylallyl halide, benzyl halide, or the like, in an aprotic solvent such as methylene chloride, THF, DMSO, DMF, dioxane, acetonitrile, or the like, or mixtures thereof, optionally containing water (1–90% in volume), at a temperature from about −20° C. to about 100° C., in the presence of a base such as lutidine, DBU, DMAP, sodium hydroxide, potassium hydroxide, sodium hydride, potassium hydride, potassium tert-butoxide, potassium hydroxide, KHMDS, or the like, optionally adding a phase-transfer catalyst such as tetrabutylammonium iodide, benzyltriethylammonium chloride, n-cetyltrimethylammonium bromide, tetraphenylphosphonium bromide, 18-crown-6, or the like, to provide the corresponding ether 6. Simultaneous deprotection at C-20 acetal and C-23-bis-siloxyl groups on 6 with an aqueous acidic solution of sulfuric acid, hydrochloric acid, hydrofluoric acid, acetic acid, or the like, in an organic solvent such as acetone, acetonitrile, THF, 1,4-dioxane, or the like, or combinations thereof, at a temperature from about 0° C. to about 100° C. for 1–24 hours, to provide a 2'-protected intermediate which is further deprotected by methanolysis at temperatures ranging from about room temperature to about reflux, thereby removing the $R^P$ protecting group at the 2'-position, where $OR^P$ is an ester or siloxyl group, to provide a compound of Formula I, where A=CHO and $R_5$ is hydrogen.

The C-23-siloxyl group of 6 can be selectively deprotected by treatment with an acid such as acetic acid, propanoic acid, or the like, in an organic solvent such as acetone, acetonitrile, methanol, ethanol, or the like, or combinations thereof, at a temperature from about 0° C. to about 100° C. for 1–24 hours, to provide 7.

In one embodiment of scheme 1, 7 can be further acylated by an acylating reagent such as carboxylic acid, acyl chloride, anhydride, mixed anhydride, or the like, in an aprotic organic solvent such as methylene chloride, ethylene chloride, THF, chloroform, DMF, acetonitrile or the like, at a temperature from about 0° C. to about 100° C. for about 0.5–48 hours, optionally in the presence of a base such as triethylamine, pyridine, DBU, DMAP, imidazole, sodium hydride, potassium hydride, potassium tert-butoxide, potassium hydroxide, KHMDS, or the like, and a condensation agent such as DCC, CDI, para-nitrophenyl chloroformate, molecular sieves, or the like, to provide the corresponding ester 8, where Rz can be $C_1$–$C_6$-alkyl, $C_2$–$C_6$-alkenyl or $C_2$–$C_6$-alkynyl, each optionally substituted with one or more substituents selected from the group consisting of halogen, $OR_6$, aryl, substituted aryl, heterocyclic and substituted heterocyclic, where $R_6$ is as previously defined.

In another embodiment of scheme 1, 7 can also be treated with an isocyanate reagent in an aprotic solvent such as methylene chloride, ethylene chloride, THF, chloroform, DMF, acetonitrile, or the like, at a temperature from about 0° C. to about 50° C. for 1–48 hours, optionally in the presence of a base such as triethylamine, pyridine, DBU, DMAP, imidazole, sodium hydride, potassium tert-butoxide, potassium hydroxide, KHMDS or the like, to provide the corresponding carbamate 9.

In yet another embodiment of scheme 1, 7 can be alkylated by an alkylating agent such as an alkyl halide, alkyl sulphonate, alkynyl halide, alkenyl halide, arylallyl halide, heteroarylallyl halide, benzyl halide, or the like, in an aprotic solvent such as methylene chloride, TBF, DMSO, DMF, dioxane, acetonitrile, or the like or mixtures thereof, optionally containing water (1–90% in volume), at a temperature from about −20° C. to about 100° C., in the presence of a base such as lutidine, DBU, DMAP, sodium hydroxide, potassium hydroxide, sodium hydride, potassium hydride, potassium tert-butoxide, potassium hydroxide, KHMDS, or the like, and optionally adding a phase-transfer catalyst such as tetrabutylammonium iodide, benzyltriethylammonium chloride, n-cetyltrimethylammonium bromide, tetraphenylphosphonium bromide, 18-crown-6, or the like, to provide 10. Removal of the protecting groups on 8, 9 and 10 (as described above for 6) provides compounds of Formula I.

hydride, potassium tert-butoxide, potassium hydroxide, KHMDS, or the like, and optionally adding a phase-transfer catalyst such as tetrabutylammonium iodide, benzyltriethylammonium chloride, n-cetyltrimethylammonium bromide, Scheme 2

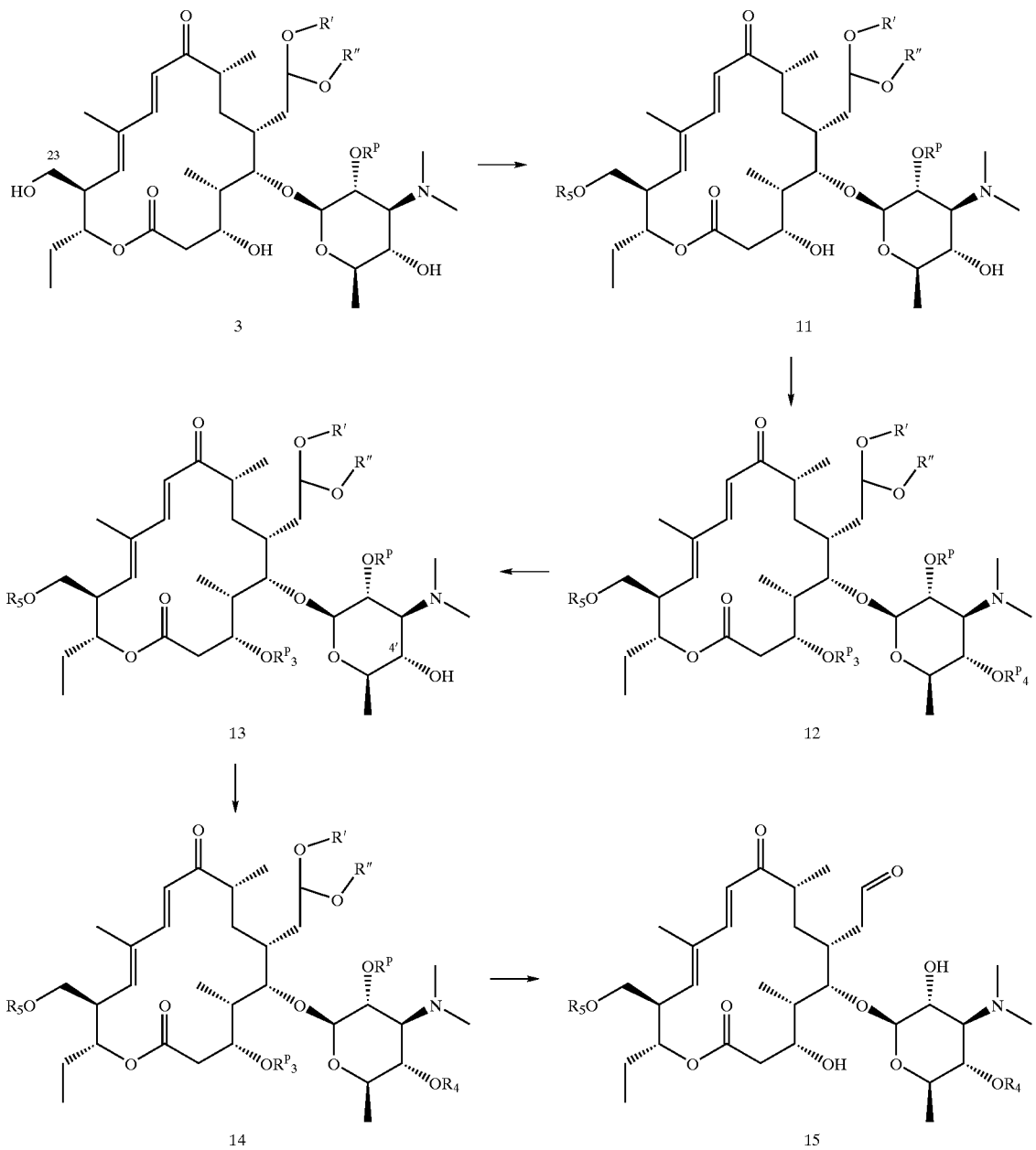

In yet another process of the invention for the preparation of the compounds of Formula I, 3 of Scheme 2, where $OR^P$ is an ester can be alkylated by an alkylating agent such as an alkyl halide, alkyl sulphonate, alkynyl halide, alkenyl halide, arylallyl halide, heteroarylallyl halide, benzyl halide, or the like, in an aprotic solvent such as methylene chloride, THF, DMSO, DMF, dioxane, acetonitrile, or the like or mixtures thereof, optionally containing water (1–90% in volume), at a temperature from about −20° C. to about 100° C., in the presence of a base such as lutidine, DBU, DMAP, sodium hydroxide, potassium hydroxide, sodium hydride, potassium tetraphenylphosphonium bromide, 18-crown-6, or the like, to provide 11. 11 is then treated with a silylating agent such as HMDS, BSA, triethylsilyl chloride, TMSCl, TBDMSCl, TBDPSCl, or the like, optionally with the addition of a catalyst such as, DMAP, imidazole, or the like, in an aprotic solvent such as methylene chloride, ethylene chloride, THF, chloroform, DMF, acetonitrile, or the like, at a temperature from about 0° C. to about 50° C. for about 1–48 hours, to provide 12, where $R^P_3$ and $R^P_4$ are hydroxy protecting groups. Selective deprotection at 4'-position is achieved by treating 12 with an acid such as acetic acid, propanoic acid or phenolic acid or the like in an organic solvent such as acetone, acetonitrile, methanol, ethanol or the like, or combinations thereof, at a temperature from about −20° C. to about 100° C. for about 1–24 hours, to provide 13. 13 can be further derivatized at the 4'-position to provide 14 by the methodologies of synthesizing 8, 9 and 10 from 7 at 4'-position as described above in scheme 1. Removal of protecting groups on 13 and 14 as described above for 6, provides 15 (of Formula I).

In yet another process of the invention for the preparation of the compounds of Formula I, 14a of Scheme 2 is obtained by alkylating 13 with allyl bromide or propargyl bromide, as described earlier in scheme 1. The propargyl group of 14a is reduced with a variety of borane or stannane reagents to give vinyl boronic acid 14b for further palladium catalyzed Suzuki or Stille coupling reactions to provide 14c (see (a) Suzuki, Chemical Reviews, 1995, 95, 2457; (b) Suzuki, Pure & Appl. Chem. 1991, 63, 419). 14a is treated with an

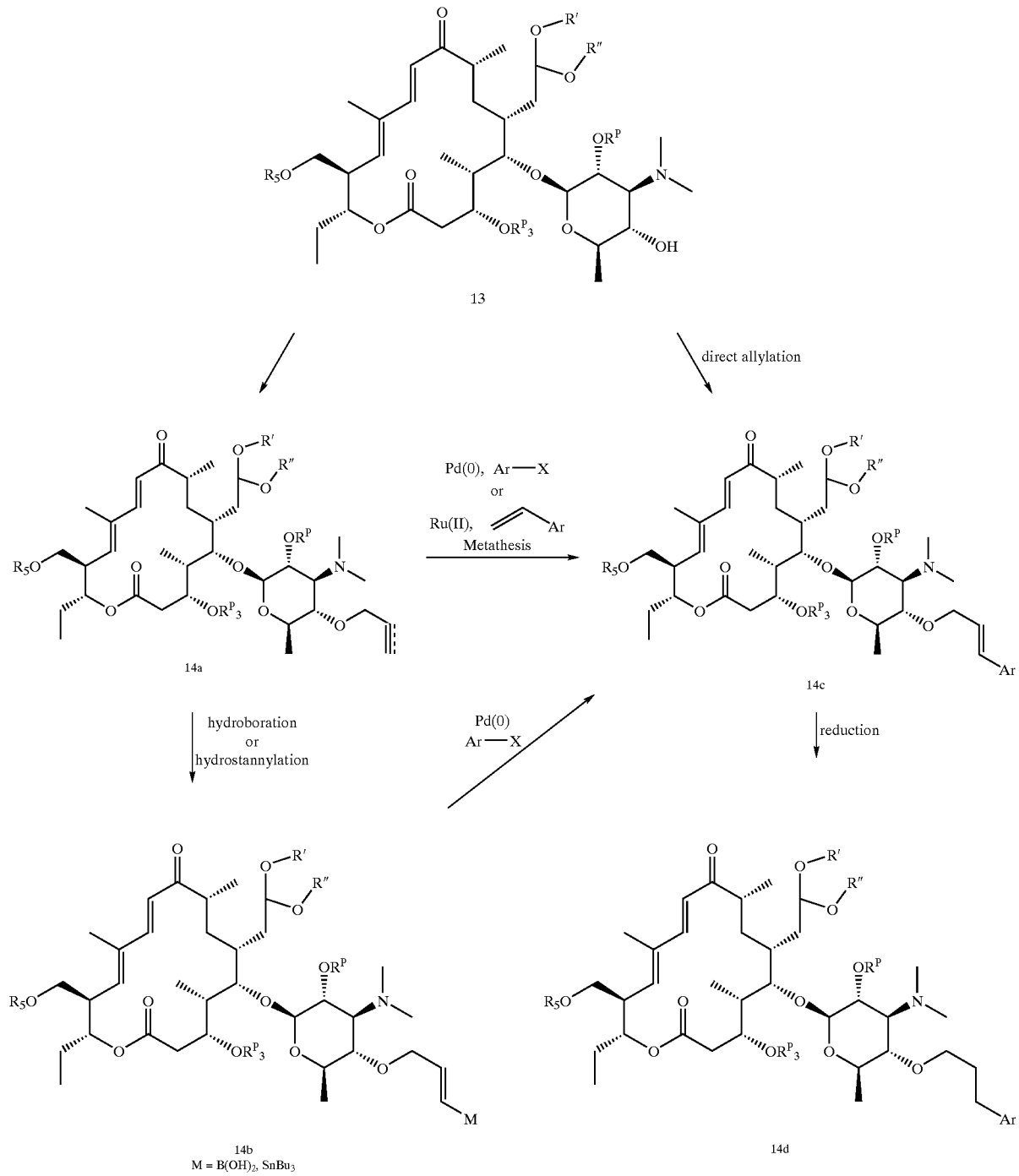

aryl halide or aryl triflate in the presence of a palladium catalyst [Pd(0) or Pd(II)] to provide 14c: (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, *Synthesis* 1977, 777). Under the Heck coupling conditions, regio isomers and steric isomers of the double bond are possible. Alternatively, 14a can undergo a cross metathesis reaction with vinylaromatic derivatives using ruthenium catalysts (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, $2^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Alternatively, 13 of scheme 2 is reacted with a tert-butyl allyl carbonate or an tert-butyl arylallyl carbonate catalyzed by a palladium catalyst [Pd(0) or Pd(II)] to provide 14c directly: (See (a) Trost, B. M. *Angew. Chem. Int. Ed. Eng.* 1989, 28, 1179. (b) Heck, Palladium Reagents in Organic Synthesis, Academic Press: New York, 1985, Chapter 1. (c) Tsuji Tetrahedron Lett. 1992, 33, 2987.). The multiple bonds conjugated with the aromatic ring at the 4'-position of 14c can be saturated with a reducing reagent such as hydrogen, cyclohexene, 1,3-cyclohexadiene, ammonium formate, tri-n-butyltin hydride, triethylsilane, borane, alane, trimethylphosphine, stannous chloride, or the like, optionally in the presence of a metallic catalyst such as Pd, Rh, Ir, Pt, Ru, Cu, Co, Fe, Ir, or the like, to provide 14d.

In yet another process of the invention for the preparation of the compounds of Formula I, 14 of Scheme 2 is treated with TBAF or hydrofluoric acid, to remove the 3-silyl protecting group to provide 16. 16 can be further derivatized at the 3-position by an alkylating agent such as an alkyl halide, alkyl sulphonate, alkynyl halide, alkenyl halide, arylallyl halide, heteroarylallyl halide, benzyl halide, or the like in an aprotic solvent such as methylene chloride, THF, DMSO, DMF, dioxane, acetonitrile, or the like or mixtures thereof, optionally containing water (1–90% in volume), at a temperature from about −20° C. to about 100° C., in the presence of a base such as lutidine, DBU, DMAP, sodium hydroxide, potassium hydroxide, sodium hydride, potassium hydride, potassium tert-butoxide, potassium hydroxide, KHMDS, or the like, and optionally adding a phase-transfer catalyst such as tetrabutylammonium iodide, benzyltriethylammonium chloride, n-cetyltrimethylammonium bromide, tetraphenylphosphonium bromide, 18-crown-6, or the like, to provide 17. Removal of protecting groups on 17, as described earlier for 6, provides 18 (of Formula I).

Scheme 4

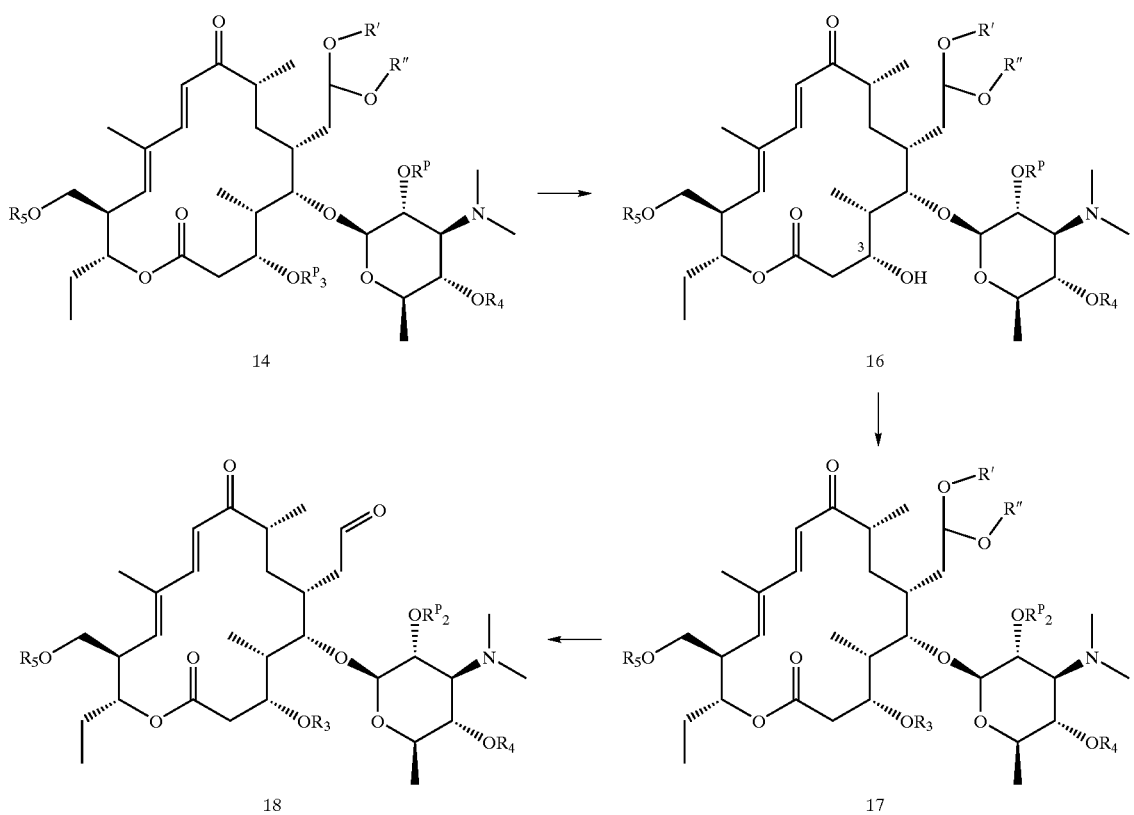

Scheme 5

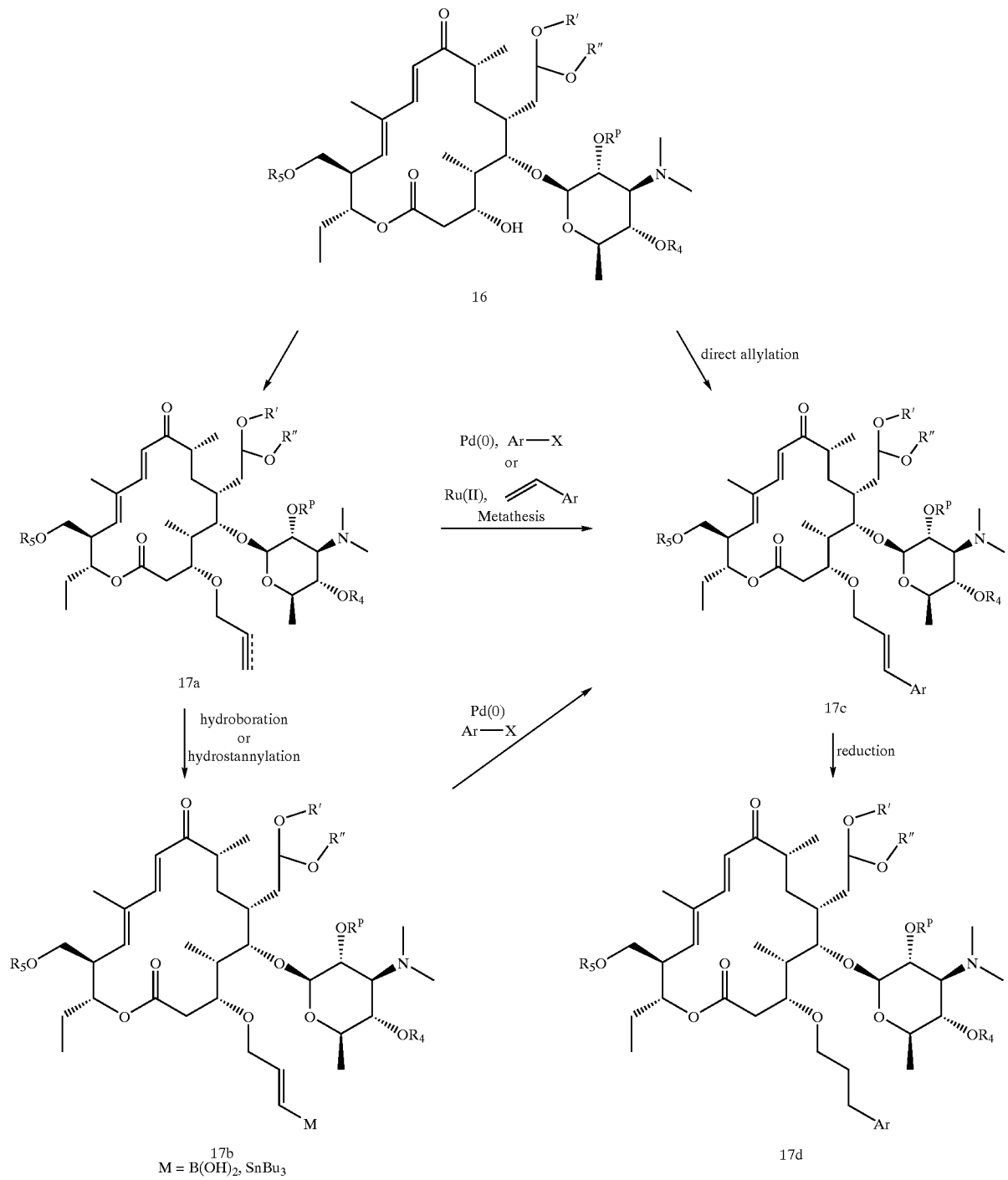

In yet another process of the invention for the preparation of the compounds of Formula I, 17a of Scheme 5 is obtained by alkylating 16 with allyl bromide or propargyl bromide, as described above in scheme 1. The propargyl group of 17a is reduced with a variety of borane or stannane reagents to give vinyl boronic acid 17b for further palladium catalyzed Suzuki or Stille coupling reactions to provide 17c (see (a) Suzuki, Chemical Reviews, 1995, 95, 2457; (b) Suzuki, Pure & Appl. Chem. 1991, 63, 419). 17a is treated with an aryl halide or aryl triflate in the presence of a palladium catalyst [Pd(0) or Pd(II)] to provide 17c: (See (a) Heck, Palladium Reagents in Organic Synthesis, Academic Press: New York, 1985, Chapter 1; (b) Sonogashira, Comprehensive Organic Synthesis, Volume 3, Chapters 2 and 4; (c) Sonogashira, Synthesis 1977, 777). Under the Heck coupling conditions, regio isomers and steric isomers of the double bond are possible. Alternatively, 17a can undergo a cross metathesis reaction with vinylaromatic derivatives using ruthenium catalysts (see (a) J. Org. Chem. 2000, 65, 2204–2207; (b) Reviews: Synlett. 1999, 2, 267; (c) Reviews:

Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Alternatively, 16 of scheme 2 is reacted with a tert-butyl allyl carbonate or an tert-butyl arylallyl carbonate catalyzed by a palladium catalyst [Pd(0) or Pd(II)] to provide 17c directly: (See (a) Trost, B. M. *Angew. Chem. Int. Ed. Eng.* 1989, 28, 1179. (b) Heck, Palladium Reagents in Organic Synthesis, Academic Press: New York, 1985, Chapter 1. (c) Tsuji Tetrahedron Lett. 1992, 33, 2987). The multiple bonds conjugated with the aromatic ring at the 4'-position of 17c can be saturated with a reducing reagent such as hydrogen, cyclohexene, 1,3-cyclohexadiene, ammonium formate, tri-n-butyltin hydride, triethylsilane, borane, alane, trimethylphosphine, stannous chloride, or the like, optionally in the presence of a metallic catalyst such as Pd, Rh, Ir, Pt, Ru, Cu, Co, Fe, Ir, or the like, to provide 17d.

halide, allyl halide, arylallyl halide, heteroarylallyl halide, benzyl halide or the like in the presence of a base such as sodium hydride, potassium hydride, potassium tert-butoxide, potassium hydroxide, KEMDS, or the like, in an aprotic solvent such as THF, DMSO, DMF, dioxane, or the like or mixtures thereof, from a temperature from about −20° C. to about 60° C. to provide 21. 19, 20 and 21 can be deprotected by stirring in methanol at a temperature, from about room temperature to about reflux, to remove the $R^P$ protecting group at the 2'-position where $OR^P$ is an ester, to provide compounds of Formula I.

The procedures described above for preparing the compounds of Formula I of the present invention will be better understood in connection with the following examples which are intended to be illustrative only, and not limiting of the scope of the invention. Various changes and modifications to the disclosed embodiments will be apparent to those skilled in the art. Such changes and modifications, including Scheme 6

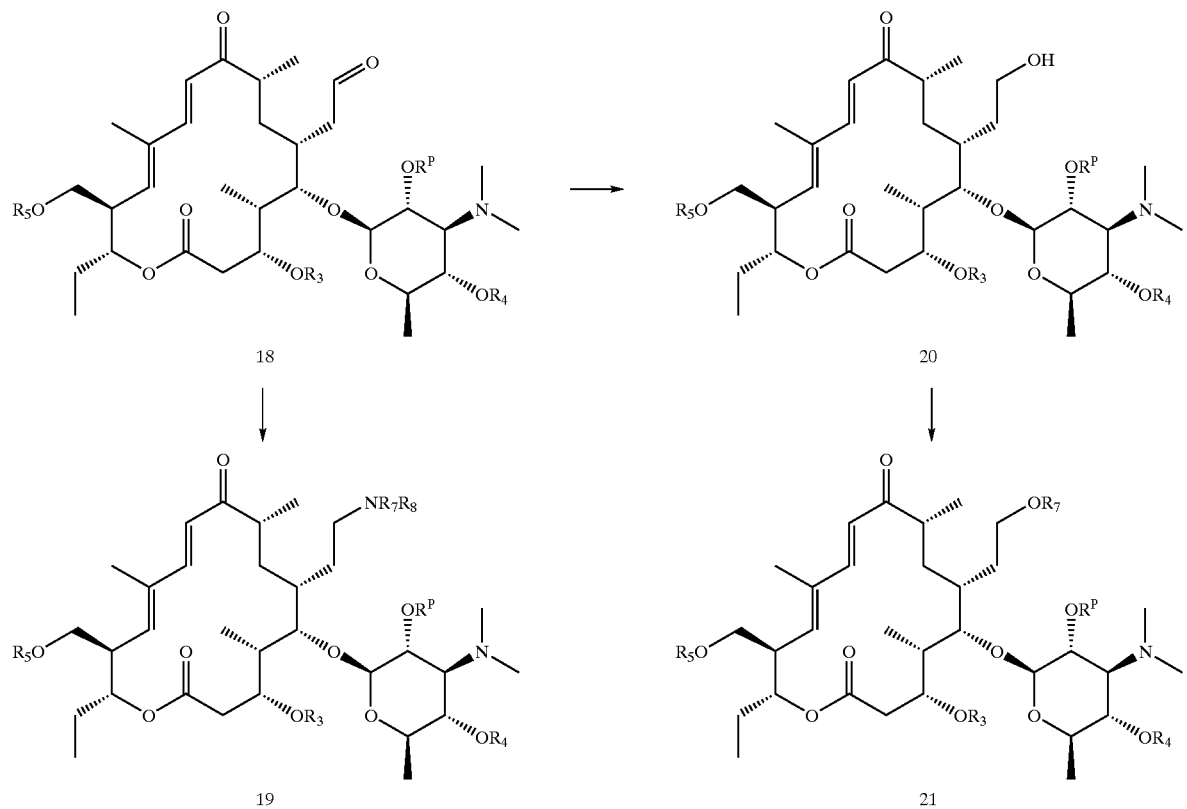

In yet another process of the invention for the preparation of the compounds of Formula I, 18 of scheme 6 can be derivatized to an amino derivative via reductive amination methods by treating with an amine compound in the presence of sodium borohydride, sodium cyanoborohydride, or the like, in an alcoholic solvent such as methanol, ethanol or isopropanol or in acetonitrile, or the like, at a pH from about 2 to about 6 to give 19. 18 can also be reduced to the corresponding alcohol with various hydride reducing agents such as sodium borohydrides, lithium borohydrides or the like, in an organic solvent such as methanol, ethanol, isopropanol, acetonitrile, THF, or the like, to provide 20. 20 can be converted to an ether compound of the invention by treatment with an alkyl halide, alkyl sulphonate, propargyl without limitation, those relating to the chemical structures, substituents, derivatives, syntheses, formulations and/or methods of the invention, may be made without departing from the spirit of the invention and the scope of the appended claims.

EXAMPLES

Example 1

Compound of Formula I: A=—CHO, $R_1$ and $R_2$ taken together=O, $R_3$=H, $R_4$=H, $R_5$=C(O)-3-quinolyl, and $R^P$=H Step 1a. 2 of Scheme 1: $R^P$=H and $R_4$=H;

A solution of tylosin (916 mg, 1.0 mmol) in aqueous TFA (0.50 M, 30 mL) was refluxed for 1.5 hours with stirring.

After being cooled to room temperature, the solution was basified with $NaHCO_3$. The mixture was extracted with methylene chloride. The combined extracts were dried ($Na_2SO_4$) and evaporated. The residue was chromatographed on silica (previously basified with triethylamine, $CH_2Cl_2$:MeOH/95:5) to give the title compound (OMT) (314 mg, 52.6%).

MS (ESI) m/z 598 (M+H)$^+$. $^{13}$C-NMR (100 MHz, CDCl$_3$): δ 203.4, 203.1, 173.7, 148.1, 142.5, 135.1, 118.2, 103.8, 80.7, 75.1, 73.1, 70.6, 70.5, 70.0, 67.2, 61.6, 46.9, 44.5, 43.5, 41.5, 40.3, 39.3, 32.4, 31.8, 25.3, 17.6, 17.2, 12.9, 9.5, 8.7.

Step 1b. 2 of Scheme 1: $R^P$=—COCH$_3$ and $R_4$=—COCH$_3$;

A mixture of the compound from step 1a (1.195 g, 2.0 mmol) and acetic anhydride (1.50 mL, 16.0 mmol) in acetone (10 mL) was stirred at room temperature for 2 hours and then evaporated. The residue was dissolved in toluene (5 mL) and evaporated (the process was repeated two more times), giving the title compound (1.355 g, 99.3%) after drying.

MS (ESI) m/z 682 (M+H)$^+$. $^{13}$C-NMR (100 MHz, CDCl$_3$): δ 203.7, 203.1, 173.7, 169.7, 169.2, 148.1, 142.2, 135.4, 118.0, 101.5, 80.5, 74.9, 71.2, 70.8, 70.3, 66.9, 66.5, 62.0, 46.9, 44.8, 43.3, 41.0, 40.6, 39.2, 31.5, 30.9, 25.2, 21.1, 21.0, 17.3, 17.0, 12.9, 9.5, 8.4.

Step 1c. Compound of Formula I: A=—CHO, $R_1$ and $R_2$ taken together=O, $R_3$=H and (i) $R_5=R^P=R_4$=Ac, (ii) $R_5$=OH, $R^P=R_4$=Ac, and (iii) $R_5=R_4$=OH, $R^P$=Ac;

The compound from step 1a (1.195 g, 2.0 mmol) was acetylated with acetic anhydride as described in step 1b for 2 hrs. The reaction mixture was partitioned between EtOAc and saturated $NaHCO_3$. The organic layer was treated with Et$_3$N (0.5 mL) for 45 minutes and then evaporated. Chromatography on silica ($CH_2Cl_2$:MeOH/99:1~92:8) afforded three products: 1) the title compound (98 mg, 6.8%); 2) the compound of step 1b (884 mg, 64.8%) and 3) a side-product (178 mg, 13.9%).

MS (ESI) m/z 724 (M+H)$^+$. $^{13}$C-NMR (100 MHz, CDCl$_3$): δ 203.1, 203.0, 173.6, 170.7, 169.7, 169.2, 147.5, 140.0, 135.6, 118.6, 101.6, 80.5, 74.4, 71.3, 70.9, 70.4, 67.0, 66.6, 63.3, 44.9, 43.6, 43.4, 41.1, 40.7, 39.2, 31.4, 31.0, 25.2, 21.2, 21.1, 20.6, 17.3, 17.0, 12.9, 9.4, 8.4.

The side-product (Compound of formula I: A=—CHO, $R_1$ and $R_2$ taken together=O, $R_3$=H, $R_4$=H, $R_5$=H and $R^P$=H)

MS (ESI) m/z 640 (M+H)$^+$. $^{13}$C-NMR (100 MHz, CDCl$_3$): δ 203.7, 203.1, 173.6, 169.1, 148.1, 142.3, 135.3, 118.0, 101.6, 80.0, 74.9, 72.7, 70.3, 70.1, 68.9, 66.4, 61.8, 46.9, 44.8, 43.3, 41.1, 40.6, 39.2, 31.4, 31.0, 25.1, 21.3, 17.6, 17.3, 12.9, 9.5, 8.4.

Step 1d. 4 of Scheme 1: $R^P_1$=H, $R^P_3$=H, $R^P_4$=—COCH$_3$, $R^P$=—COCH$_3$, and R'=R''=CH$_3$;

Into a solution of the compound from step 1b (1.738 g, 2.55 mmol) in dry MeCN (7.0 mL) and MeOH (7.0 mL) was added camphorsulfonic acid (651 mg, 2.80 mmol) at 0° C. The mixture was kept at 0° C. for 2 hours and Et$_3$N (0.40 mL, 2.87 mmol) was added. After evaporation, the residue was partitioned between EtOAc and saturated $NaHCO_3$. The organic layer was washed successively with saturated $NaHCO_3$, water and brine. The organic layer was dried ($Na_2SO_4$) and evaporated to give the title compound (1.826 g, 98.4%).

MS (ESI) m/z 728 (M+H)$^+$. $^{13}$C-NMR (100 MHz, CDCl$_3$): δ 204.0, 173.5, 169.7, 169.2, 147.5, 142.0, 135.3, 118.3, 102.3, 101.8, 80.9, 74.9, 71.3, 70.7, 70.4, 67.0, 66.6, 61.9, 53.4, 49.8, 46.9, 44.8, 41.2, 41.0, 39.6, 32.7, 32.5, 30.8, 25.1, 21.1, 21.0, 17.5, 17.0, 12.9, 9.5, 8.5.

Step 1e. Compound of Formula I: A=—CHO, $R_1$ and $R_2$ taken together=O, $R_3=R_4$=H, $R_5$=—COCH$_3$, and $R^P$=H;

A solution of the compound from step 1c (40.0 mg, 0.055 mmol) in MeOH (2.0 mL) was stirred at room temperature for 70 hours. The solution was evaporated to give the title compound (35.3 mg, 100%).

MS (ESI) m/z 640 (M+H)$^+$. $^{13}$C-NMR (100 MHz, CDCl$_3$): δ 203.1, 202.9, 173.8, 170.8, 147.6, 140.1, 135.6, 118.4, 103.9, 81.0, 74.5, 73.3, 70.9, 70.8, 70.1, 63.4, 47.1, 44.6, 43.7, 41.6, 39.4, 32.7, 31.9, 25.3, 20.7, 17.8, 17.3, 12.9, 9.5, 8.9.

Step 1f. Compound of Formula I: A=—CHO, $R_1$ and $R_2$ taken together=O, $R_3$=H, $R_4$=—C(O)CH$_3$, $R_5$=—C(O)-3-quinolyl, and $R^P$=—C(O)CH$_3$;

A mixture of the compound from step 1b (55.0 mg, 0.081 mmol), 3-quinolinecarboxylic acid (17.0 mg, 0.097 mmol), DMAP (12.2 mg, 0.10 mmol) and DCC (0.2 M in $CH_2Cl_2$, 0.48 mL, 0.96 mmol) was stirred at room temperature for 13 hours. The solution was chromatographed on silica ($CH_2Cl_2$:EtOAc/9 1~1:1) to give the title compound (65.1 mg, 96.4%).

MS (ESI) m/z 837 (M+H)$^+$. $^{13}$C-NMR (100 MHz, CDCl$_3$): δ 203.1, 202.9, 173.6, 169.7, 169.2, 165.8, 149.8, 149.1, 147.2, 139.6, 136.1, 133.9, 130.1, 129.8, 128.3, 125.3, 124.9, 122.2, 119.0, 101.7, 80.5, 74.2, 71.3, 71.0, 70.4, 67.0, 66.6, 64.6, 44.9, 43.9, 41.2, 40.8, 39.3, 31.5, 31.0, 25.4, 21.2, 21.1, 17.4, 17.2, 13.0, 9.5, 8.5.

Step 1g. Compound of Formula I: A=—CHO, $R_1$ and $R_2$ taken together=O, $R_3$=H, $R_4$=H, $R_5$=C(O)-3-quinolyl, and $R^P$=H;

The title compound (20.9 mg, 36.9%) was obtained using the procedure described in step 1e from the compound of step 1f (63.0 mg, 0.075 mmol) after chromatography on silica ($CH_2Cl_2$:MeOH/92.5:2.5~95:5).

MS (ESI) m/z 753 (M+H)$^+$. $^{13}$C-NMR (100 MHz, CDCl$_3$): δ 203.0, 202.8, 173.8, 165.8, 149.9, 149.1, 147.3, 139.7, 136.1, 134.0, 130.1, 129.8, 128.4, 125.3, 125.0, 122.2, 119.3, 104.0, 80.8, 74.3, 73.3, 71.0, 70.8, 70.0, 64.7, 44.6, 44.0, 43.7, 41.7, 39.4, 32.6, 32.0, 25.5, 17.8, 17.3, 13.0, 9.6, 9.0.

Example 2

Compound of Formula I: A=—CHO, $R_1$ and $R_2$ taken together=O, $R_3$=H, $R_4$=H, $R_5$=—C(O)CH$_2$-3-pyridyl and $R^P$=H.

Step 2a. Compound of Formula I: A=—CHO, $R_1$ and $R_2$ taken together=O, $R_3$=H, $R_4$=—C(O)CH$_3$, $R_5$=—C(O)CH$_2$-3-pyridyl and $R^P$=—C(O)CH$_3$;

The title compound (51.0 mg, 72.1%) was obtained from the compound of step 1b (60.2 mg, 0.088 mmol) using the procedure described in step 1f.

MS (ESI) m/z 801 (M+H)$^+$. $^{13}$C-NMR (100 MHz, CDCl$_3$): δ 203.4, 203.2, 173.8, 170.6, 170.0, 169.4, 150.4, 148.9, 147.5, 139.8, 137.0, 136.0, 129.5, 123.7, 119.1, 101.9, 80.8, 74.4, 71.6, 71.2, 70.7, 67.3, 66.9, 64.2, 45.2, 44.0, 43.7, 41.4, 41.0, 39.5, 38.6, 31.7, 31.2, 25.5, 21.5, 21.4, 17.6, 17.4, 13.1, 9.7, 8.7.

Step 2b. Compound of Formula I: A=—CHO, $R_1$ and $R_2$ taken together=O, $R_3$=H, $R_4$=H, $R_5$=—C(O)CH$_2$-3-pyridyl and $R^P$=H.

The title compound (37.2 mg, 81.6%) was obtained from the compound of step 2a (51.0 mg, 0.064 mmol) using the procedure described in step 1e after chromatography on silica ($CH_2Cl_2$:MeOH/92.5:2.5~90:10).

MS (ESI) m/z 717 (M+H)$^+$. $^{13}$C-NMR (100 MHz, CDCl$_3$): δ 203.1, 202.9, 173.7, 170.3, 150.2, 148.6, 147.4, 139.6, 136.9, 135.8, 129.3, 123.5, 119.3, 104.0, 80.9, 74.3, 73.3, 70.9, 70.8, 70.1, 64.1, 44.6, 43.8, 41.6, 39.4, 38.3, 25.4, 17.8, 17.3, 12.8, 9.5, 8.9.

Example 3

Compound of Formula I: A=—CHO, $R_1$ and $R_2$ taken together=O, $R_3$=H, $R_4$=H, $R_5$=—C(O)CH$_2$CH$_2$-3-pyridyl and $R^P$=H.

Step 3a. Compound of Formula I: A=—CHO, $R_1$ and $R_2$ taken together=O, $R_3$=H, $R_4$=—C(O)CH, $R_5$=—C(O)CH$_2$CH$_2$-3-pyridyl and $R^P$=—C(O)CH$_3$;

The title compound (37.7 mg, 70%) was obtained from the compound of step 1b (45.0 mg, 0.066 mmol) using the procedure described in step 1f.

MS (ESI) m/z 815 (M+H)$^+$. $^{13}$C-NMR (100 MHz, CDCl$_3$): δ 203.2, 203.0, 173.6, 172.1, 170.0, 169.2, 149.7, 147.9, 147.4, 139.8, 135.8, 135.7, 135.5, 123.4, 118.8, 101.7, 80.6, 74.3, 71.3, 71.0, 70.5, 67.1, 66.6, 63.5, 44.9, 43.7, 43.5, 41.2, 40.8, 39.3, 35.0, 31.5, 31.0, 27.9, 25.2, 21.3, 21.2, 17.4, 17.2, 13.0, 9.5, 8.5.

Step 3b. Compound of Formula I: A=—CHO, $R_1$ and $R_2$ taken together=O, $R_3$=H, $R_4$=H, $R_5$=—C(O)CH$_2$)CH$_2$-3-pyridyl and $R^P$=H.

The title compound (33.5 mg, 99.1%) was obtained from the compound of step 3a (37.7 mg, 0.046 mol) using the procedure described in step 1e.

MS (ESI) m/z 731 (M+H)$^+$. $^{13}$C-NMR (100 MHz, CDCl$_3$): δ 203.1, 202.8, 173.7, 172.1, 149.7, 147.8, 147.5, 139.8, 135.8, 135.7, 135.5, 123.4, 119.2, 104.0, 80.9, 74.3, 73.3, 70.9, 70.8, 70.1, 63.6, 44.6, 43.7, 41.7, 39.4, 35.0, 27.9, 25.3, 17.8, 17.3, 12.9, 9.5, 8.9.

Example 4

Compound of Formula I: A=—CHO, $R_1$ and $R_2$ taken together=O, $R_3$=H, $R_4$=H, $R_5$=—C(O)CH=CH-3-pyridyl and $R^P$=H.

Step 4a. Compound of Formula I: A=—CHO, $R_1$ and $R_2$ taken together=O, $R_3$=H, $R_4$=—C(O)CH, $R_5$=C(O)CH=CH-3-pyridyl and $R^P$=—C(O)CH$_3$;

The title compound (39.9 mg, 74.4%) was obtained from the compound of step 1b (45.0 mg, 0.066 mmol) using the procedure described in step 1f.

MS (ESI) m/z 813 (M+H)$^+$. $^{13}$C-NMR (100 MHz, CDCl$_3$): δ 203.2, 203.0, 173.7, 169.7, 169.2, 166.0, 151.2, 149.8, 147.5, 141.9, 139.9, 135.8, 134.3, 130.0, 123.7, 119.4, 118.8, 101.7, 80.6, 74.4, 71.3, 71.0, 70.4, 67.1, 66.7, 63.7, 45.0, 43.8, 43.5, 41.2, 40.8, 39.3, 31.5, 31.0, 25.3, 21.3, 21.2, 17.4, 17.2, 13.1, 9.6, 8.5.

Step 4b. Compound of Formula I: A=—CHO, $R_1$ and $R_2$ taken together=O, $R_3$=H, $R_4$=H, $R_5$=—C(O)CH=CH-3-pyridyl and $R^P$=H.

The title compound (35.0 mg, 97.8%) was obtained from the compound of step 4a (39.9 mg, 0.049 mmol) using the procedure described in step 1e.

MS (ESI) m/z 729 (M+H)$^+$. $^{13}$C-NMR (100 MHz, CDCl$_3$): δ 203.1, 202.8, 173.8, 166.0, 151.2, 149.8, 147.5, 141.9, 139.9, 135.8, 134.3, 129.9, 123.7, 119.4, 103.9, 74.5, 73.3, 70.9, 70.8, 70.1, 63.7, 44.6, 43.8, 43.7, 41.7, 39.4, 25.4, 17.8, 17.3, 13.0, 9.6, 8.9.

Example 5

Compound of Formula I: A=—CHO, $R_1$ and $R_2$ taken together=O, $R_3$=H, $R_4$=H, $R_5$=—C(O)NH$_2$ and $R^P$=H.

Step 5a. Compound of Formula I: A=—CHO, $R_1$ and $R_2$ taken together=O, $R_3$=H, $R_4$=—C(O)CH, $R_5$=—C(O)NH and $R^P$=—C(O)CH$_3$;

A mixture of the compound from step 1b (200.0 mg, 0.293 mmol) and 1,1'-carbonyldiimidazole (95.0 mg, 0.586 mmol) in anhydrous acetonitrile (5.0 mL) was stirred at room temperature for 6 hours before aqueous ammonia (28 wt %, 2.0 mL) was added. Stirring was continued for 0.5 hour. The solution was concentrated and the residue was partitioned between EtOAc and water. The organic layer was washed with water and brine, dried and evaporated. The title compound (180.0 mg, 84.7%) was obtained by chromatography on silica (CH$_2$Cl$_2$:MeOH/99:1~96:4).

MS (ESI) m/z 725 (M+H)$^+$. $^{13}$C-NMR (100 MHz, CDCl$_3$): δ 203.1, 203.0, 173.6, 169.7, 169.1, 156.4, 147.6, 140.3, 135.4, 118.5, 101.6, 80.4, 74.4, 71.2, 70.9, 70.3, 66.9, 66.5, 63.8, 44.8, 43.9, 43.4, 41.1, 40.6, 39.2, 31.4, 30.9, 25.1, 21.1, 21.0, 17.3, 17.1, 12.9, 9.5, 8.4.

Step 5b. Compound of Formula I: A=CHO, $R_1$ and $R_2$ taken together=O, $R_3$=H, $R_4$=H, $R_5$=C(O)NH$_2$ and $R^P$=H.

The title compound (50.0 mg, 99.2%) was obtained from the compound of step 5a (57.0 mg, 0.079 mmol) using the procedure described in step 1e.

MS (ESI) m/z 641 (M+H)$^+$. $^{13}$C-NMR (100 MHz, CDCl$_3$): δ 203.1, 202.9, 173.8, 156.4, 147.7, 140.3, 135.6, 118.9, 104.0, 81.0, 74.6, 73.3, 70.9, 70.8, 70.0, 67.7, 64.0, 44.6, 44.0, 43.7, 41.6, 40.4, 39.4, 32.6, 31.6, 25.3, 17.8, 17.3, 12.9, 9.6, 8.9.

Example 6

Compound of Formula I: A=—CHO, $R_1$ and $R_2$ taken together=O, $R_3$=H, $R_4$=H, $R_5$=—C(O)NH-Phenyl and $R^P$=H.

Step 6a. Compound of Formula I: A=—CHO, $R_1$ and $R_2$ taken together=O, $R_3$=H, $R_4$=—C(O)CH, $R_5$=—C(O)NH-Phenyl and $R^P$=—C(O)CH$_3$;

To a mixture of the compound of step 1b (42.0 mg, 0.062 mmol) and phenylisocyanate (10.0 μL, 0.092 mmol) in methylene chloride (0.50 mL) was added Et$_3$N (34.3 μL, 0.25 mmol). The mixture was stirred at room temperature for 22 hours and then chromatographed on silica (CH$_2$Cl$_2$:MeOH/99.5:0.5~98.5:1.5) to give the title compound (34.0 mg, 69%).

MS (ESI) m/z 801 (M+H)$^+$. $^{13}$C-NMR (100 MHz, CDCl$_3$): δ 203.2, 203.0, 173.7, 169.8, 169.2, 153.0, 147.5, 140.1, 137.5, 135.7, 129.0, 123.6, 118.8, 101.7, 80.6, 74.4, 71.4, 71.0, 70.5, 67.1, 66.7, 64.1, 45.0, 44.0, 43.5, 41.2, 40.8, 39.3, 31.5, 31.0, 25.3, 21.3, 21.2, 17.4, 17.2, 13.1, 9.6, 8.5.

Step 6b. Compound of Formula I: A=—CHO, $R_1$ and $R_2$ taken together=O, $R_3$=H, $R_4$=H, $R_5$=—C(O)NH-Phenyl and $R^P$=H.

The title compound (30.3 mg, 99.7%) was obtained from the compound of step 6a (34.0 mg, 0.042 mmol) using the procedure described in step 1e.

MS (ESI) m/z 717 (M+H)$^+$. $^{13}$C-NMR (100 MHz, CDCl$_3$): δ 203.1, 202.9, 173.9, 153.0, 147.6, 140.2, 137.5, 135.7, 129.1, 123.6, 118.7, 104.0, 74.5, 73.3, 71.0, 70.8, 70.1, 64.1, 44.6, 44.0, 43.7, 41.7, 39.4, 32.0, 25.4, 17.8, 17.3, 13.0, 9.6, 9.0.

Example 7

Compound of Formula I: A=—CHO, $R_1$ and $R_2$ taken together=O, $R_3$=H, $R_4$=H, $R_5$=—C(O)NH-p-tolyl and $R^P$=H.

Step 7a. Compound of Formula I: A=—CHO, $R_1$ and $R_2$ taken together=O, $R_3$=H, $R_4$=—C(O)CH$_3$, $R_5$=—C(O)NH-p-tolyl and $R^P$=C(O)CH$_3$;

To a solution of the compound from step 1b (100 mg, 0.15 mmol) in CH$_2$Cl$_2$ (2 mL), Et$_3$N (82 μL, 0.59 mmol, 4 eq) was added at 0° C. followed by the addition of p-tolyl isocyanate (37 μL, 0.3 mmol, 2 eq). The reaction mixture was warmed up to room temperature under N$_2$. The reaction was completed in 20 minutes. It was treated with water and the resulting mixture was stirred for 5–10 minutes at room temperature and diluted with CH$_2$Cl$_2$ (50 mL). The organic phase was washed with saturated NaHCO$_3$ (2×30 mL), brine (1×30 mL), dried (Na$_2$SO$_4$) and concentrated under reduced pressure. Purification of the crude mixture by flash chromatography (CH$_2$Cl$_2$:MeOH/50:1) gave 100 mg (84%) of the title compound.

MS (ESI) m/z 815 (M+H)$^+$.

Step 7b. Compound of Formula I: A=—CHO, R$_1$ and R$_2$ taken together=O, R$_3$=H, R$_4$=H, R$_5$=—C(O)NH-p-tolyl and R$^P$=H.

A solution of the compound from step 7a (100 mg) in MeOH (3 mL) was stirred at room temperature for 15 hours. The solvent was evaporated and the residue was purified on a silica gel column (CH$_2$Cl$_2$:MeOH/20: 1) giving 60 mg (67%) of the title compound as a white solid.

MS (ESI) m/z 731 (M+H)$^+$. $^{13}$C NMR (100 MHz, (CD$_3$)$_2$CO): δ 203.0, 202.4, 174.0, 153.8, 147.2, 140.5, 136.9, 136.0, 132.0, 129.4, 120.0, 118.5, 104.5, 81.0, 78.5, 74.7, 73.4, 71.2, 70.9, 70.7, 67.5, 64.0, 45.0, 44.3, 43.8, 41.4, 40.9, 39.5, 32.0, 25.2, 20.0, 17.5, 16.8, 12.5, 9.3, 8.6.

Example 8

Compound of Formula I: A=—CHO, R$_1$ and R$_2$ taken together=O, R$_3$=H, R$_4$=H, R$_5$=—C(O)NH-4-methylthiophenyl and R$^P$=H.

Step 8a. Compound of Formula I: A=—CHO, R$_1$ and R$_2$ taken together=O, R$_3$=H, R$_4$=—C(O)CH$_3$, R$_5$=—C(O)NH-4-methylthiophenyl and R$^P$=C(O)CH$_3$;

To a solution of the compound from step 1b (150 mg, 0.22 mmol) in CH$_2$Cl$_2$ (2 mL), Et$_3$N (123 μL, 0.88 mmol, 4 eq) was added at 0° C. followed by the addition of 4-(methylthio)phenyl isocyanate (62 μL, 0.44 mmol, 2 eq). The reaction mixture was warmed up to room temperature under N$_2$. The reaction was completed in 1 hour. It was treated with water and the resulting mixture was stirred for 5–10 minutes at room temperature and diluted with CHCl$_3$ (50 mL). The organic phase was washed with saturated NaHCO$_3$ (30 mL) and brine (30 mL), dried (Na$_2$SO$_4$) and concentrated under reduced pressure giving 290 mg of the crude title compound that was used in the next step without further purification.

Step 8b. Compound of Formula I: A=—CHO, R$_1$ and R$_2$ taken together=O, R$_3$=H, R$_4$=H, R$_5$=—C(O)NH-4-methylthiophenyl and R$^P$=H.

A solution of the crude title compound of step 8a (290 mg) in MeOH (10 mL) was stirred at room temperature for 15 hours. The solvent was evaporated and the residue was purified on a silica gel column (acetone) giving 137 mg (82%) of the title compound as a white solid.

MS (ESI) m/z 763 (M+H)$^+$.

Example 9

Compound of Formula I: A=—CHO, R$_1$ and R$_2$ taken together=O, R$_3$=H, R$_4$=H, R$_5$=—C(O)NH-4-methoxyphenyl and R$^P$=H.

Step 9a. Compound of Formula I: A=—CHO, R$_1$ and R$_2$ taken together=O, R$_3$=H, R$_4$=—C(O)CH$_3$, R$_5$=—C(O)NH-4-methoxyphenyl and R$^P$=C(O)CH$_3$;

The title compound (120 mg, 66%) was obtained from the compound of step 1b (150 mg, 0.22 mmol) and 4-methoxyphenyl isocyanate (123 uL, 0.88 mmol) using the procedure described in step 8a after chromatography (silica, CH$_2$Cl$_2$:MeOH/40:1)

MS (ESI) m/z 831 (M+H)$^+$.

Step 9b. Compound of Formula I: A=—CHO, R$_1$ and R$_2$ taken together=O, R$_3$=H, R$_4$=H, R$_5$=—C(O)NH-4-methoxyphenyl and R$^P$=H.

A solution of the title compound from step 9a (120 mg) in MeOH (10 mL) was stirred at room temperature for 15 hours. Removal of the solvent under reduced pressure gave 100 mg (92%) of the title compound as a white solid.

MS (ESI) m/z 747 (M+H)$^+$. $^{13}$C NMR (100 MHz, CDCl$_3$): δ 203.4, 203.3, 174.1, 156.2, 153.7, 147.9, 140.5, 135.8, 130.9, 120.9, 114.4, 104.2, 74.7, 73.5, 71.1, 71.06, 70.3, 55.7, 44.9, 44.2, 43.9, 41.9, 39.6, 25.5, 18.0, 17.5, 13.2, 9.8, 9.2.

Example 10

Compound of Formula I: A=—CHO, R$_1$ and R$_2$ taken together=O, R$_3$=H R$_4$=H, R$_5$=—C(O)NH-4-dimethylaminophenyl and R$^P$=H.

Step 10a. Compound of Formula I: A=—CHO, R$_1$ and R$_2$ taken together=O, R$_3$=H, R$_4$=—C(O)CH$_3$, R$_5$=—C(O)NH-4-dimethylaminophenyl and R$^P$=—C(O)CH$_3$;

The crude title compound was obtained from the compound of step 1b (150 mg, 0.22 mmol) and 4-(dimethylamino)phenyl isocyanate (71 mg, 0.44 mmol) using the procedure described in step 8a.

Step 10b. Compound of Formula I: A=—CHO, R$_1$ and R$_2$ taken together=O, R$_3$=H, R$_4$=H, R$_5$=—C(O)NH-4-dimethylaminophenyl and R$^P$=H.

A solution of the crude compound of step 10a in MeOH (10 mL) was stirred at room temperature for 15 hours. The solvent was evaporated and the residue was purified on a silica gel column (CH$_2$Cl$_2$:MeOH/25:1) giving 110 mg (70%) of the title compound as a solid.

MS (ESI) m/z 760 (M+H)$^+$. $^3$C NMR (100 MHz, CDCl$_3$): δ 203.3, 203.2, 174.1, 153.8, 147.9, 140.6, 136.9, 135.8, 132.0, 127.5, 121.2, 118.5, 113.5, 104.2, 81.3, 77.5, 74.8, 73.5, 71.14, 71.05, 70.3, 64.2, 44.8, 44.3, 43.9, 41.9, 41.2, 39.6, 25.6, 18.0, 17.5, 13.2, 9.8, 9.1.

Example 11

Compound of Formula I: A=—CHO, R$_1$ and R$_2$ taken together=O, R$_3$=H, R$_4$=H, R$_5$=—C(O)NH-4-phenoxyphenyl and R$^P$=H.

Step 11a. Compound of Formula I: A=—CHO, R$_1$ and R$_2$ taken together=O, R$_3$=H, R$_4$=—C(O)CH$_3$, R$_5$=—C(O)NH-4-phenoxyphenyl and R$^P$=C(O)CH$_3$;

The crude title compound was obtained from the compound of step 1b (200 mg, 0.3 mmol) and 4-phenoxyphenyl isocyanate (106 uL, 0.59 mmol) using the procedure described in step 8a.

Step 11b. Compound of Formula I: A=—CHO, R$_1$ and R$_2$ taken together=O, R$_3$=H, R$_4$=H, R$_5$=—C(O)NH-4-phenoxyphenyl and R$^P$=H.

A solution of the crude title compound of step 11a in MeOH (10 mL) was stirred at room temperature for 1.5 days. The solvent was evaporated and the residue was purified on a silica gel column (CH$_2$Cl$_2$:MeOH/97:3) to give 100 mg (42%) of the title compound as a white solid.

MS (ESI) m/z 809 (M+H)$^+$. $^{13}$C NMR (100 MHz, CDCl$_3$): δ 203.5, 203.3, 174.1, 157.8, 153.6, 153.1, 147.9, 140.5, 135.9, 133.5, 129.9, 123.2, 120.7, 120.0, 118.5, 104.1, 81.0, 77.5, 74.7, 73.5, 71.13, 71.08, 70.3, 64.3, 44.9, 44.2, 43.9, 41.9, 39.7, 25.6, 18.0, 17.6, 13.2, 9.8, 9.2.

Example 12

Compound of Formula I: A=—CHO, R$_1$ and R$_2$ taken together=O, R$_3$=H, R$_4$=H, R$_5$=—C(O)NH-4-cyanophenyl and R$^P$=H.

Into a solution of the compound from step 1b (150 mg, 0.22 mmol) in dichloromethane (2 mL), 4-cyanophenyl isocyanate (48 mg, 0.33 mmol) and triethylamine (44 mg, 0.44 mmol) were added dropwise at 0° C. The reaction mixture was stirred for 10 minutes at 0° C., then warmed to room temperature and stirred for another one and a half hours. The mixture was purified by flash chromatography (dichloromethane methanol:98 2) to give 157 mg (87%) of a white solid. A mixture of the resulting white solid and methanol (3 mL) was stirred at room temperature overnight and concentrated under reduced pressure. The residue was purified by flash chromatography ($CH_2Cl_2$:MeOH/98:2) to give 41 mg (35%) of pure title compound.

MS (ESI) m/z 742 (M+H)$^+$. $^{13}$C-NMR (100 MHz, $CDCl_3$): δ 203.2, 173.8, 152.7, 147.6, 142.1, 139.7, 135.8, 133.3, 118.9, 118.4, 106.2, 77.2, 74.3, 73.3, 70.9, 70.8, 70.1, 64.4, 50.7, 44.8, 43.8, 43.7, 41.6, 39.4, 32.4, 25.3, 20.7, 17.8, 17.4, 13.0, 9.6, 8.9

Example 13

Compound of Formula I: A=—CHO, $R_1$ and $R_2$ taken together=O, $R_3$=H, $R_4$=H, $R_5$=—C(O)NH-4-nitrophenyl and $R^P$=H.

Into a solution of the compound from step 1b (200 mg, 0.29 mmol) in dichloromethane (2 mL), 4-nitrophenyl isocyanate (58 mg, 0.35 mmol) and triethylamine (89 mg, 0.87 mmol) were added dropwise at 0° C. The reaction mixture was stirred for 2 hours at 0° C., then warmed to room temperature and stirred for another hour. Additional 4-nitrophenyl isocyanate (11 mg, 0.06 mmol) was added to the reaction mixture. The reaction mixture was stirred for another three hours, concentrated under reduced pressure and purified by flash chromatography ($CH_2Cl_2$:MeOH/98:2) to give 142 mg (58%) of a yellow solid. A mixture of the resulting yellow solid and methanol (5 mL) was stirred at room temperature overnight, refluxed for half an hour and concentrated under reduced pressure. The residue was purified by flash chromatography ($CH_2Cl_2$:MeOH/96:4) to give pure title compound (99 mg, 78%).

MS (ESI) m/z 762 (M+H)$^+$. $^{13}$C-NMR (100 MHz, $CDCl_3$): δ 203.2, 173.8, 152.6, 147.6, 144.0, 143.9, 143.0, 139.7, 135.8, 125.2, 117.9, 103.9, 77.2, 74.2, 73.3, 70.9, 70.8, 70.1, 64.6, 53.9, 50.8, 44.8, 43.8, 43.7, 41.7, 39.4, 25.3, 20.7, 17.8, 17.4, 13.0, 9.6, 9.0

Example 14

Compound of Formula I: A=—CHO, $R_1$ and $R_2$ taken together=O, $R_3$=H, $R_4$=H, $R_5$=—C(O)NH-α,α,α-trifluoro-p-tolyl and $R^P$=H.

Into a solution of the compound from step 1b (150 mg, 0.22 mmol) in dichloromethane (2 mL) was added α,α,α-trifluoro-p-tolyl isocyanate (62 mg, 0.33 mmol) and triethylamine (44 mg, 0.44 mmol) dropwise at 0° C. The reaction mixture was stirred for 10 minutes at 0° C., warmed to room temperature, stirred for another one and a half hours, quenched by addition of water (10 mL) and extracted with chloroform. The extract was dried ($Na_2SO_4$), filtered and concentrated under reduced pressure. A mixture of the crude compound and methanol (3 mL) was stirred at room temperature over three nights and concentrated under reduced pressure. The residue was purified by flash chromatography ($CH_2Cl_2$:MeOH/98:2) to give pure title compound (87 mg, 51%).

MS (ESI) m/z 785 (M+H)$^+$. $^{13}$C-NMR (100 MHz, $CDCl_3$): δ 203.2, 203.0, 173.8, 152.8, 147.6, 140.9, 135.8, 126.3, 125.5, 125.4, 125.2, 124.8, 122.7, 118.2, 103.9, 77.2, 74.3, 73.3, 71.0, 70.8, 70.1, 64.4, 53.4, 44.7, 43.9, 43.7, 41.7, 39.4, 25.4, 17.8, 17.3, 13.0, 9.6, 8.9

Example 15

Compound of Formula I: A=—CHO, $R_1$ and $R_2$ taken together=O, $R_3$=H, $R_4$=H, $R_5$=—C(O)NH-4-fluoro-3-nitrophenyl and $R^P$=H.

Into a solution of the compound of step 1b (150 mg, 0.22 mmol) in dichloromethane (2 mL) was added 4-fluoro-3-nitrophenyl isocyanate (60 mg, 0.33 mmol) and triethylamine (44 mg, 0.44 mmol) dropwise at 0° C. The reaction mixture was stirred for 10 minutes at 0° C., warmed to room temperature and stirred for another hour. The mixture was purified by flash chromatography ($CH_2Cl_2$:MeOH/98:2) to give 126 mg (66%) of a white solid. A mixture of the crude compound and methanol (3 mL) was stirred at room temperature over three nights and concentrated under reduced pressure to give pure title compound (117 mg, 100%).

MS (ESI) m/z 780 (M+H)$^+$. $^{13}$C-NMR (100 MHz, $CDCl_3$): δ 203.4, 203.3, 173.9, 153.1, 152.6, 150.0, 147.7, 139.9, 137.2, 137.1, 135.8, 134.7, 125.3, 118.9, 118.7, 115.6, 103.8, 77.2, 74.3, 73.3, 70.9, 70.8, 70.1, 64.3, 44.8, 43.8, 43.7, 41.7, 39.5, 34.6, 31.5, 25.3, 22.6, 20.6, 17.8, 17.3, 14.0, 13.0, 9.6, 8.9

Example 16

Compound of Formula I: A=—CHO, $R_1$ and $R_2$ taken together=O, $R_3$=H, $R_4$=H, $R_5$=—C(O)NH-3,4-difluorophenyl and $R^P$=H.

Into a solution of the compound of step 1b (150 mg, 0.22 mmol) in dichloromethane (2 mL) was added 3,4-difluorophenyl isocyanate (68 mg, 0.44 mmol) and triethylamine (44 mg, 0.44 mmol) dropwise at 0° C. The reaction mixture was stirred for 10 minutes at 0° C., warmed to room temperature, stirred for another 20 minutes, quenched by addition of water (10 mL) and extracted with chloroform. The extract was dried ($Na_2SO_4$), filtered and concentrated under reduced pressure. A mixture of the crude compound and methanol (3 mL) was stirred at room temperature overnight and concentrated under reduced pressure. The residue was purified by flash chromatography ($CH_2Cl_2$:MeOH/98:2) to give pure title compound (95 mg, 58%).

MS (ESI) m/z 753 (M+H)$^+$. $^{13}$C-NMR (100 MHz, $CDCl_3$): δ 203.1, 203.0, 173.8, 153.0, 151.5, 151.3, 149.0, 148.9, 147.6, 145.4, 140.0, 135.8, 134.2, 117.3, 117.2, 114.2, 103.9, 77.2, 74.3, 73.3, 70.9, 70.8, 70.1, 64.3, 44.7, 43.9, 43.7, 41.6, 39.4, 25.3, 17.8, 17.3, 13.0, 9.6, 8.9

Example 17

Compound of Formula I: A=—CHO, $R_1$ and $R_2$ taken together=O, $R_3$=H, $R_4$=H, $R_5$=—C(O)NH-3,5-difluorophenyl and $R^P$=H.

The compound of step 1b (200 mg, 0.29 mmol) was reacted with 3,5-difluorophenyl isocyanate using the procedure described in Example 16 to give the title compound (115 mg, 70%).

MS (ESI) m/z 753 (M+H)$^+$. $^{13}$C-NMR (100 MHz, $CDCl_3$): δ 203.2, 203.0, 173.8, 164.6, 164.4, 162.1, 162.0, 152.7, 147.5, 140.1, 140.0, 135.9, 103.9, 101.8, 101.5, 98.6, 77.2, 74.3, 73.3, 71.0, 70.9, 70.1, 64.5, 44.7, 43.9, 43.7, 41.7, 39.5, 25.4, 17.8, 17.3, 13.0, 9.6, 8.9

Example 18

Compound of Formula I: A=—CHO, $R_1$ and $R_2$ taken together=O, $R_3$=H, $R_4$=H, $R_5$=—C(O)NH-4-acetylphenyl and $R^P$=H.

The compound of step 1b (200 mg, 0.29 mmol) was reacted with 4-acetylphenyl isocyanate using the procedure described in Example 16 to give the title compound (114 mg, 69%).

MS (ESI) m/z 759 (M+H)$^+$. $^{13}$C-NMR (100 MHz, $CDCl_3$): δ 203.2, 203.1, 173.8, 152.8, 147.6, 142.4, 139.9, 135.7, 132.1, 129.8, 117.7, 103.8, 77.2, 74.3, 73.2, 70.8, 70.0, 64.2, 44.7, 43.8, 43.7, 41.6, 39.4, 26.3, 25.2, 17.7, 17.3, 13.0, 9.6, 8.9

Example 19

Compound of formula I: A=—CHO, $R_1$ and $R_2$ taken together=O, $R_3$=H, $R_4$=H, $R_5$=—C(O)NH-(4-fluoro)phenyl and $R^P$=H.

Step 19a. Compound of Formula I: A=—CHO, $R_1$ and $R_2$ taken together=O, $R_3$=H, $R_4$=—C(O)$CH_3$, $R_5$=—C(O)NH-(4-fluoro)phenyl and $R^P$=—C(O)$CH_3$;

Into a solution of the compound of step 1b (136.3 mg, 0.20 mmol) and triethyl amine (68 mg, 0.6 mmol) in dichloromethane (1.5 mL) was added 4-fluorophenyl isocyanate (41.1 mL, 0.3 mmol). The mixture was stirred for 5 hours at room temperature, diluted with dichloromethane, washed with saturated aqueous $NaHCO_3$, and dried over anhydrous $Na_2SO_4$. The solvent was evaporated and the residue was purified on a silica gel column (eluting with acetone:hexane/1:5) to give the title compound (101 mg, 62%)

MS (ESI) m/z 819 (M+H)$^+$.

Step 19b. Compound of Formula I: A=—CHO, $R_1$ and $R_2$ taken together=O, $R_3$=H, $R_4$=H, $R_5$=—C(O)NH-(4-fluoro)phenyl and $R^P$=H.

A solution of the compound of step 19a (101 mg) in methanol (5 mL) was stirred at room temperature for 16 hours. The solvent was evaporated under vacuum to give the title compound (90 mg, 100%).

MS (ESI) m/z 735 (M+H)$^+$. $^{13}$C-NMR (100 MHz, $CDCl_3$): δ 203.3, 203.1, 174.1, 160.5, 153.5, 147.8, 140.3, 135.9, 133.7, 120.7, 116.0, 115.8, 104.2, 74.6, 73,5, 71.2, 71.0, 70.3, 64.4, 60.6, 53.9, 44.9, 44.2, 43.9, 41.9, 39.6, 31.9, 29.4, 25.6, 21.2, 18.0, 17.5, 14.4, 132, 9.8, 9.1.

Example 20

Compound of Formula I: A=—CHO, $R_1$ and $R_2$ taken together=O, $R_3$=H, $R_4$=H, $R_5$=—C(O)NH-(4-chloro)phenyl and $R^P$=H.

The compound of step 1b was processed as described in steps 19a and 19b of Example 19, substituting 4-chlorophenyl isocyanate for 4-fluorophenyl isocyanate to provide the title compound (100 mg, 67%) as a white solid.

MS (ESI) m/z 751 (M+H)$^+$. $^{13}$C-NMR (100 MHz, $CDCl_3$): δ 203.4, 203.2, 174.1, 153.2, 147.8, 140.2, 136.5, 135.9, 129.2, 128.7, 120.1, 104.1, 74.6, 73.5, 71.1, 71.0, 70.3, 64.4, 50.9, 44.8, 44.1, 43.9, 41.9, 39.7, 29.1, 25.5, 21.2, 17.9, 17.5, 13.3, 9.8, 9.1.

Example 21

Compound of Formula I: A=—CHO, $R_1$ and $R_2$ taken together=O, $R_3$=H, $R_4$=H, $R_5$=—C(O)NH-(4-bromo)phenyl and $R^P$=H.

The compound of step 1b was processed as described in steps 19a and 19b of Example 19, substituting 4-bromophenyl isocyanate for 4-fluorophenyl isocyanate to provide the title compound (93 mg, 58%) as a white solid.

MS (ESI) m/z 796 (M+H)$^+$. $^{13}$C-NMR (100 MHz, $CDCl_3$): δ 203.3, 203.2, 174.1, 153.2, 147.8, 140.2, 137.0, 135.9, 132.2, 120.5, 116.2, 74.6, 73.5, 71.1, 71.0, 70.3, 60.6, 44.9, 44.1, 43.9, 41.9, 39.7, 29.8, 29.4, 25.5, 21.2, 18.0, 17.5, 14.4, 13.2, 9.8, 9.2.

Example 22

Compound of Formula I: A=—CHO, $R_1$ and $R_2$ taken together=O, $R_3$=H, $R_4$=H, $R_5$=—C(O)NHCH$_2$Phenyl and $R^P$=H.

Step 22a. Compound of Formula I: A=—CHO, $R_1$ and $R_2$ taken together=O, $R_3$=H, $R_4$=—C(O)CH$_3$, $R_5$=—C(O)NHCH$_2$Phenyl and $R^P$=—C(O)CH$_3$;

The title compound (47.7 mg, 93%) was obtained from the compound of step 1b (42.9 mg, 0.063 mmol) using the procedure described in step 6a for 5 hours.

MS (ESI) m/z 815 (M+H)$^+$. $^{13}$C-NMR (100 MHz, $CDCl_3$): δ 203.2, 203.0, 173.7, 169.7, 169.2, 156.0, 147.6, 140.4, 138.1, 135.5, 128.7, 127.5, 127.4, 118.6, 101.7, 80.6, 74.5, 71.4, 71.0, 70.5, 67.1, 66.7, 63.9, 45.1, 44.9, 44.1, 43.5, 41.2, 40.8, 39.3, 31.5, 31.0, 25.3, 21.3, 21.2, 17.4, 17.2, 13.0, 9.6, 8.5.

Step 22b. Compound of Formula I: A=—CHO, $R_1$ and $R_2$ taken together=O, $R_3$=H, $R_4$=H, $R_5$=—C(O)NHCH$_2$Phenyl and $R^P$=H.

The title compound (41.9 mg, 98.0%) was obtained from the compound of step 22a (47.7 mg, 0.058 mmol) using the procedure described in step 1e.

MS (ESI) m/z 731 (M+H)$^+$. $^{13}$C-NMR (100 MHz, $CDCl_3$): δ 203.1, 202.8, 173.9, 156.0, 147.6, 140.4, 138.1, 135.5, 128.7, 127.5, 127.4, 119.0, 104.0, 81.1, 74.6, 73.3, 70.9, 70.8, 70.1, 64.0, 45.1, 44.1, 43.7, 41.7, 39.4, 25.4, 17.8, 17.3, 12.9, 9.6, 8.9.

Example 23

Compound of Formula I: A=—CHO, $R_1$ and $R_2$ taken together=O, $R_3$=H, $R_4$=H, $R_5$=—C(O)NHCH$_2$CH$_2$Phenyl and $R^P$=H.

Step 23a. Compound of Formula 1: A=—CHO, $R_1$ and $R_2$ taken together=O, $R_3$=H, $R_4$=—C(O)CH$_3$, $R_5$=—C(O)NHCH$_2$CH$_2$Phenyl and $R^P$=—C(O)CH$_3$;

The title compound (45.8 mg, 94.0%) was obtained from the compound of step 1b (40.1 mg, 0.059 mmol) using the procedure described in step 6a for 27 hours.

MS (ESI) m/z 829 (M+H)$^+$. $^{13}$C-NMR (100 MHz, $CDCl_3$): δ 203.1, 203.0, 173.7, 169.8, 169.2, 155.9, 147.6, 140.4, 138.5, 135.5, 128.7, 128.6, 126.5, 118.6, 101.7, 80.6, 74.5, 71.4, 71.0, 70.5, 67.1, 66.7, 63.9, 45.0, 44.1, 43.5, 42.2, 41.2, 40.8, 39.3, 36.0, 31.5, 31.0, 25.2, 21.3, 21.2, 17.4, 17.2, 13.0, 9.6, 8.5.

Step 23b. Compound of Formula I: A=—CHO, $R_1$ and $R_2$ taken together=O, $R_3$=H, $R_4$=H, $R_5$=—C(O)NHCH$_2$CH$_2$Phenyl and $R^P$=H.

The title compound (40.7 mg, 99.0%) was obtained from the compound of step 23a (45.8 mg, 0.055 mmol) using the procedure described in step 1e.

MS (ESI) m/z 745 (M+H)$^+$. $^{13}$C-NMR (100 MHz, $CDCl_3$): δ 203.1, 202.9, 173.9, 155.9, 147.7, 140.5, 138.5, 135.5, 128.7, 128.6, 126.5, 119.0, 104.0, 81.0, 74.6, 73.3, 71.0, 70.8, 70.1, 63.8, 44.1, 43.7, 42.2, 41.6, 39.4, 36.0, 25.3, 17.8, 17.3, 13.0, 9.6, 8.9.

Example 24

Compound of Formula I: A=—CHO, $R_1$ and $R_2$ taken together=O, $R_3$=H, $R_4$=H, $R_5$=—C(O)NHCH$_2$CHCH$_2$ and $R^P$=H.

Step 24a. Compound of Formula I: A=CH(OCH$_3$)$_2$, $R_1$ and $R_2$ taken together=O, $R_3$=H, $R_4$=C(O)CH, $R_5$=C(O)CH$_2$CHCH$_2$ and $R^P$=—C(O)CH$_3$;

The title compound (533.6 mg, 94%) was obtained from the compound of step 1d (509.5 mg, 0.70 mmol), allyl isocyanate (123.8 μL, 1.40 mmol) and triethylamine (390 μL, 2.80 mmol) in CH$_2$Cl$_2$ (5.0 mL) using the procedure described in step 6a for 2 hours.

MS (ESI) m/z 811 (M+H)$^+$. $^{13}$C-NMR (100 MHz, $CDCl_3$): δ 203.8, 173.6, 169.7, 169.2, 155.9, 147.1, 140.3, 135.5, 135.4, 118.9, 115.4, 102.4, 102.1, 81.3, 74.5, 71.5, 70.9, 70.6, 67.2, 66.8, 63.8, 53.5, 49.9, 44.9, 44.1, 43.4, 42.8, 41.2, 39.6, 32.9, 32.6, 30.9, 25.1, 21.3, 21.2, 17.6, 17.1, 12.9, 9.5, 8.6.

Step 24b. Compound of Formula I: A=—CHO, $R_1$ and $R_2$ taken together=O, $R_3$=H, $R_4$=—C(O)CH$_3$, $R_5$=—C(O)CH$_2$CHCH$_2$ and $R^P$=—C(O)CH$_3$;

To a solution of the compound of step 24a (32 mg) in CH$_3$CN (1 mL) was added 0.3 N HCl aqueous solution (1 mL). The mixture was stirred for 1 hour at room temperature, neutralized with saturated aqueous $NaHCO_3$ and extracted with dichloromethane. The organic solution was dried over anhydrous $Na_2SO_4$ and evaporated to give the title compound (28 mg, 93%).

MS (ESI) m/z 765 (M+H)$^+$.

Step 24c. Compound of Formula I: A=—CHO, $R_1$ and $R_2$ taken together=O, $R_3$=H, $R_4$=H, $R_5$=—C(O)NHCH$_2$CHCH$_2$ and $R^P$=H.

A solution of the compound from step 24b (28 mg) in methanol (5 mL) was stirred at room temperature for 16 hours. The solvent was evaporated under vacuum to give the title compound (24 mg, 100%).

MS (ESI) m/z 861 (M+H)$^+$.

Example 25

Compound of Formula I: A=—CHO, $R_1$ and $R_2$ taken together=O, $R_3$=H, $R_4$=H, $R_5$=—C(O)NHCH$_2$CH$_2$Br and $R^P$=H.

Step 25a. Compound of Formula I: A=—CHO, $R_1$ and $R_2$ taken together =O, $R_3$=H, $R_4$=—C(O)CH$_3$, $R_5$=—C(O)NHCH$_2$CH$_2$Br and $R^P$=—C(O)CH$_3$;

The title compound (57.5 mg, 65.5%) was obtained from the compound of step 1b (72.8 mg, 0.10 mmol) using the procedure described in step 6a for 10 hrs.

MS (ESI) m/z 877 (M+H)$^+$. $^{13}$C-NMR (100 MHz, CDCl$_3$): δ 203.7, 173.6, 169.7, 169.2, 155.8, 147.1, 140.1, 135.5, 119.0, 102.4, 102.1, 81.2, 74.4, 71.5, 70.9, 70.5, 67.2, 66.8, 64.1, 53.5, 49.8, 45.8, 45.5, 44.9, 44.1, 42.7, 41.2, 39.7, 32.9, 32.6, 32.0, 25.1, 21.3, 21.2, 17.7, 17.2, 13.0, 9.5, 8.6.

Step 25b. Compound of Formula I: A=CHO, $R_1$ and $R_2$ taken together=O, $R_3$=H, $R_4$=H, $R_5$=—C(O)NHCH$_2$CH$_2$Br and $R^P$=H.

The title compound is obtained from the compound of Step 25a using the procedures described in Step 24b and Step 1e.

Example 26

Compound of Formula I: A=—CHO, $R_1$ and $R_2$ taken together=O, $R_3$=H, $R_4$=H, $R_5$=—C(O)NHCH$_2$CHCH-3-quinolyl and $R^P$=H.

Step 26a. Compound of Formula I: A=CHO, $R_1$ and $R_2$ taken together=O, $R_3$=H, $R_4$=C(O)CH$_3$, $R_5$=—C(O)CH$_2$CHCH-3-quinolyl and $R^P$=—C(O)CH$_3$;

A solution of the compound of step 24a (162 mg, 0.2 mmol), 3-bromopyridine (63.2 mg, 0.4 mmol), tri-o-tolylphosphine (18.3 mg, 0.06 mmol), triethyl amine (50.6 mg, 0.50 mmol), and palladium (II) acetate (6.7 mg, 0.03 mmol) in degassed acetonitrile (1.2 mL) was heated at 80° C. for 16 hours and concentrated. Purification on a silica gel column (eluting with acetone:hexane/1:3) gave the title compound (84 mg, 47%).

MS (ESI) m/z 866 (M–Na)$^+$.

Step 26b. Compound of Formula I: A=—CHO, $R_1$ and $R_2$ taken together=O, $R_3$=H, $R_4$=—C(O)CH$_3$, $R_5$=—C(O)NHCH$_2$CHCH-3-quinolyl and $R^P$=—C(O)CH$_3$;

To a solution of the compound from step 26a (84 mg) in CH$_3$CN (2 mL) was added 0.3 N HCl aqueous solution (2 mL). The mixture was stirred for 1 hour at room temperature, neutralized with saturated aqueous NaHCO$_3$ and extracted with dichloromethane. The organic solution was dried over anhydrous Na$_2$SO$_4$ and evaporated to give the title compound (78 mg, 98%).

MS (ESI) m/z 842(M+H)$^+$.

Step 26c. Compound of Formula I: A=—CHO, $R_1$ and $R_2$ taken together=O, $R_3$=H, $R_4$=H, $R_5$=—C(O)NHCH$_2$CHCH-3-quinolyl and $R^P$=H.

A solution of the compound from step 26b (78 mg) in methanol (5 mL) was stirred at room temperature for 16 hours. The solvent was evaporated under vacuum to give the title compound (62 mg, 100%).

MS (ESI) m/z 758 (M+H)$^+$.

Example 27

Compound of Formula I: A=—CHO, $R_1$ and $R_2$ taken together=O, $R_3$=H, $R_4$=H, $R_5$=—CH$_2$OCH$_3$ and $R^P$=H.

Step 27a. Compound of Formula I: A=—CHO, $R_1$ and $R_2$ taken together=O, $R_3$=H, $R_4$=—C(O)CH$_3$, $R_5$=—CH$_2$OCH$_3$ and $R^P$=—C(O)CH$_3$;

Into a solution of the compound of step 1b (48.0 mg, 70.4 μmol) and diisopropylethylamine (55.2 μL, 0.32 mmol) in methylene chloride (0.50 mL) was added MOMCl (18.0 μL, 0.24 mmol). The mixture was stirred at room temperature 7 hrs and partitioned (EtOAc/saturated aqueous NaHCO$_3$). The organic layer was washed with water and brine, dried (Na$_2$SO$_4$) and evaporated. The residue was chromatographed (silica, hexanes:EtOAc/4:1~2:3) to give the title compound (21.6 mg, 42.3%).

MS (ESI) m/z 726 (M+H)$^+$.

Step 27b. Compound of Formula I: A=—CHO, $R_1$ and $R_2$ taken together=O, $R_3$=H, $R_4$=H, $R_5$=—CH$_2$CH$_3$ and $R^P$=H.

The title compound (19.0 mg, 99.5%) was obtained by methanolysis of the compound of step 27a at from room temperature to 50° C. for 30 hours.

MS (ESI) m/z 642 (M+H)$^+$. $^{13}$C-NMR (100 MHz, CDCl$_3$): δ 203.1, 202.9, 174.0, 147.9, 141.8, 135.0, 119.0, 104.0, 96.6, 81.2, 75.1, 73.3, 71.0, 70.8, 70.1, 67.2, 55.4, 44.8, 43.7, 41.7, 39.4, 29.7, 25.4, 17.8, 17.4, 13.0, 9.7, 8.9.

Example 28

Compound of Formula I: A=—CHO, $R_1$ and $R_2$ taken together=O, $R_3$=H, $R_4$=H, $R_5$=—CH$_2$OCH$_2$Phenyl and $R^P$=H.

Step 28a. Compound of Formula I: A=—CH(OCH$_3$)$_2$, $R_1$ and $R_2$ taken together=O, $R_3$=H, $R_4$=—C(O)CH$_3$, $R_5$=—CH$_2$OCH$_2$Phenyl and $R^P$=—C(O)CH$_3$;

The title compounds (58.3 mg, 77%) and a side product (13.8 mg, 16%) were prepared from the compound of step 1d (65.0 mg, 89.3 μmol), diisopropylethylamine (78.0 μL, 0.446 mmol) and BOMCl (43.3 μL, 0.28 mmol) in methylene chloride (0.50 mL) for 15 hours according to step 27a.

MS (ESI) m/z 848 (M+H)$^+$. $^{13}$C-NMR (100 MHz, CDCl$_3$): δ 203.7, 173.7, 169.7, 169.2, 147.4, 141.4, 137.6, 134.9, 128.4, 127.7, 118.7, 102.4, 102.1, 94.9, 81.4, 75.0, 71.5, 70.9, 70.6, 69.7, 67.4, 67.2, 53.5, 50.0, 44.7, 41.2, 39.7, 32.6, 31.0, 25.1, 21.3, 21.2, 17.7, 17.2, 13.0, 9.6, 8.7.

The side-product (Compound of Formula I: A=—CH(OCH$_3$)$_2$, $R_1$ and $R_2$ taken together=O, $R_3$=—CH$_2$OCH$_2$Phenyl, $R_4$=—C(O)CH$_3$, $R_5$=—CH$_2$OCH$_2$Phenyl and $R^P$=—C(O)CH$_3$;

MS (ESI) m/z 968 (M+H)$^+$. $^{13}$C-NMR (100 MHz, CDCl$_3$): δ 203.9, 171.5, 169.7, 169.2, 147.6, 142.0, 138.2, 137.6, 134.3, 128.5, 128.3, 127.8, 127.7, 127.6, 127.5, 118.9, 101.9, 101.3, 96.6, 94.9, 79.4, 75.8, 75.1, 71.5, 70.7, 70.5, 70.1, 69.7, 67.5, 67.2, 53.6, 49.3, 44.8, 43.7, 41.2, 40.4, 36.0, 32.7, 31.2, 29.7, 25.1, 21.4, 21.2, 17.8, 17.2, 12.9, 9.6, 9.5.

Step 28b. Compound of Formula I: A=—CHO, $R_1$ and $R_2$ taken together=O, $R_3$=H, $R_4$=—C(O)CH$_3$, $R_5$=—CH$_2$OCH$_2$Phenyl and $R^P$=—C(O)CH$_3$;

A mixture of the compound of step 28a (27.2 mg, 32.1 μmol) and hydrochloric acid (0.2 M, 2.0 mL, 2.0 mmol) in acetonitrile (2.0 mL) was stirred at room temperature for 1 hour and then partitioned (EtOAc/saturated NaHCO$_3$). The organic layer was washed with water and brine, dried (Na$_2$SO$_4$) and evaporated to give the crude title compound.

MS (ESI) m/z 802 (M+H)$^+$.

Step 28c. Compound of Formula I: A=—CHO, $R_1$ and $R_2$ taken together=O, $R_3$=H, $R_4$=H, $R_5$=—CH$_2$OCH$_2$Phenyl and $R^P$=H.

The title compound (22.1 mg, 96% two steps) was obtained from the crude compound of step 28b using the procedure described in step 1e.

MS (ESI) m/z 718 (M+H)$^+$. $^{13}$C-NMR (100 MHz, CDCl$_3$): δ 203.3, 203.1, 174.2, 148.1, 141.9, 137.8, 135.2, 128.7, 128.0, 119.0, 104.2, 95.1, 75.3, 73.6, 71.2, 71.0, 70.4, 69.9, 67.7, 45.0, 44.0, 41.9, 39.6, 29.9, 25.6, 18.0, 17.5, 13.2, 9.9, 9.2.

Example 29

Compound of Formula I: A=—CHO, $R_1$ and $R_2$ taken together=O, $R_3$=—$CH_2OCH_2$Phenyl, $R_4$=H, $R_5$=—$CH_2OCH_2$Phenyl and $R^P$=H.

Step 29a. Compound of Formula I: A=—CHO, $R_1$ and $R_2$ taken together=O, $R_3$=—$CH_2OCH_2$Phenyl, $R_4$=—C(O)$CH_3$, $R_5$=—$CH_2OCH_2$Phenyl and $R^P$=—C(O)$CH_3$;

The crude title compound was obtained from the side product of step 28a (13.8 mg, 14.2 μmol) using the procedure described in step 28b.

MS (ESI) m/z 922 (M+H)$^+$.

Step 29b. Compound of Formula I: A=—CHO, $R_1$ and $R_2$ taken together=O, $R_3$=—$CH_2OCH_2$Phenyl, $R_4$=H, $R_5$=—$CH_2OCH_2$Phenyl and $R^P$=H.

The title compound (11.3 mg, 95% two steps) was obtained from the crude product of step 29a using the procedure described in step 1e.

MS (ESI) m/z 838 (M+H)$^+$. $^{13}$C-NMR (100 MHz, CDCl$_3$): δ 203.2, 202.2, 171.3, 148.3, 142.6, 137.9, 137.6, 134.1, 128.5, 128.3, 127.8, 127.7, 127.6, 127.5, 118.6, 103.3, 96.1, 94.9, 80.2, 75.8, 75.0, 73.1, 71.1, 70.6, 70.4, 70.0, 69.7, 67.6, 44.8, 44.6, 44.4, 43.0, 41.7, 39.8, 34.8, 32.4, 31.9, 29.7, 25.3, 22.7, 17.8, 17.5, 12.8, 9.8, 9.6.

Example 30

Compound of Formula I: A=—CHO, $R_1$ and $R_2$ taken together=O, $R_3$=H, $R_4$=H, $R_5$=—$CH_3$ and $R^P$=H.

Step 30a. Compound of Formula I: A=—CH(OCH$_3$)$_2$, $R_1$ and $R_2$ taken together=O, $R_3$=H, $R_4$=—C(O)$CH_3$, $R_5$=$CH_3$ and $R^P$=—C(O)$CH_3$;

A mixture of the compound of step 1d (100.0 mg, 0.137 mmol), tetrabutylammonium iodide (25.4 mg, 0.069 mmol) and methyl iodide (85.5 μL, 1.37 mmol) in methylene chloride (0.30 mL) and NaOH (50%, 0.8 mL) was stirred at room temperature for 1 hour and then partitioned (EtOAc/water). The organic layer was washed with water and brine, dried (Na$_2$SO$_4$) and evaporated. The title compound (90.2 mg, 88.5%) was obtained by chromatography (silica, hexanes:EtOAc/4:1~1:1).

MS (ESI) m/z 742 (M+H)$^+$. $^{13}$C-NMR (100 MHz, CDCl$_3$): δ 203.6, 173.7, 169.7, 169.2, 147.4, 141.6, 134.7, 118.5, 102.4, 102.1, 81.3, 75.2, 72.3, 71.5, 70.9, 70.5, 67.2, 66.8, 59.1, 53.4, 53.3, 49.9, 44.9, 41.1, 39.6, 32.9, 32.7, 31.0, 25.3, 21.3, 21.1, 17.7, 17.1, 13.0, 9.6, 8.6.

Step 30b. Compound of Formula I: A=—CHO, $R_1$ and $R_2$ taken together=O, $R_3$=H, $R_4$=—C(O)$CH_3$, $R_5$=—$CH_3$ and $R^P$=—C(O)$CH_3$;

The crude title compound was obtained from the compound of step 30a (33.7 mg, 45.4 μmol) using the procedure described in step 28b.

MS (ESI) m/z 696 (M+H)$^+$.

Step 30c. Compound of Formula I: A=—CHO, $R_1$ and $R_2$ taken together=O, $R_3$=H, $R_4$=H, $R_5$=—$CH_3$ and $R^P$=H.

The title compound (27.1 mg, 97.5% two steps) was obtained from the crude compound of step 30b using the procedure described in step 1e.

MS (ESI) m/z 612 (M+H)$^+$. $^{13}$C-NMR (100 MHz, CDCl$_3$): δ 203.1, 202.9, 174.0, 148.0, 141.9, 134.9, 118.8, 104.0, 81.3, 75.4, 73.3, 72.6, 71.0, 70.8, 70.1, 59.2, 45.0, 44.5, 43.8, 41.7, 39.4, 32.7, 31.9, 29.6, 25.6, 17.8, 17.3, 13.0, 9.7, 8.9.

Example 31

Compound of Formula I: A=—CHO, $R_1$ and $R_2$ taken together=O, $R_3$=H, $R_4$=H, $R_5$=—$CH_2CCH$ and $R^P$=H.

Step 31a. Compound of Formula I: A=—CH(OCH$_3$)$_2$, $R_1$ and $R_2$ taken together=O, $R_3$=H, $R_4$=—C(O)$CH_3$, $R_5$=—$CH_2CCH$, and $R^P$=—C(O)$CH_3$;

The title compound (62.3 mg, 59.2%) was obtained using the procedure described in step 30a from the compound of step 1d (100.0 mg, 0.137 mmol), propargyl bromide (80 wt % in toluene, 204.3 mg, 1.37 mmol) and tetrabutylammonium iodide (25.4 mg, 0.069 mmol) in methylene chloride (0.3 mL) and NaOH (50%, 0.8 mL) for 1 hour at room temperature.

MS (ESI) m/z 766 (M+H)$^+$. $^{13}$C-NMR (100 MHz, CDCl$_3$): δ 203.7, 173.7, 169.7, 169.2, 147.4, 141.3, 134.8, 118.7, 102.4, 102.1, 81.3, 79.2, 75.1, 74.8, 71.5, 70.9, 70.6, 69.1, 67.2, 66.8, 58.4, 53.5, 50.0, 44.9, 44.7, 41.2, 39.7, 32.9, 32.6, 31.0, 29.6, 25.2, 21.3, 21.2, 17.7, 17.1, 13.0, 9.6, 8.7.

Step 31b. Compound of Formula I: A=—CHO, $R_1$ and $R_2$ taken together=O, $R_3$=H, $R_4$=—C(O)$CH_3$, $R_5$=—$CH_2CCH$ and $R^P$=—C(O)$CH_3$;

The crude title compound was obtained from the compound of step 31a (17.2 mg, 22.4 μmol) using the procedure described in step 28b.

MS (ESI) m/z 720 (M+H)$^+$.

Step 31c. Compound of Formula I: A=—CHO, $R_1$ and $R_2$ taken together=O, $R_3$=H, $R_4$=H, $R_5$=—$CH_2CCH$ and $R^P$=H.

The title compound (14.0 mg, 97.9% two steps) was obtained from the crude compound of step 31b using the procedure described in step 1e.

MS (ESI) m/z 636 (M+H)$^+$. $^{13}$C-NMR (100 MHz, CDCl$_3$): δ 203.1, 202.8, 174.0, 148.0, 141.6, 135.0, 119.1, 104.0, 79.2, 75.3, 74.9, 73.4, 71.0, 70.8, 70.2, 69.4, 60.4, 58.5, 45.0, 44.8, 43.8, 41.7, 39.4, 29.7, 25.6, 17.8, 17.4, 13.0, 9.7, 8.9.

Example 32

Compound of Formula I: A=—CHO, $R_1$ and $R_2$ taken together=O, $R_3$=H, $R_4$=H, $R_5$=—(CH$_3$)$_2$Br and $R^P$=H.

Step 32a. Compound of Formula I: A=—CH(OCH$_3$)$_2$, $R_1$ and $R_2$ taken together=O, $R_3$=H, $R_4$=—C(O)$CH_3$, $R_5$=—(CH$_3$)$_2$Br and $R^P$=—C(O)$CH_3$;

The title compound (38.5 mg, 32.5%) was obtained from the compound of step 1d (100.0 mg, 0.137 mmol), 1,4-dibromobutane (164.1 μL, 1.37 mmol) and tetrabutylammonium iodide (25.4 mg, 0.069 mmol) in methylene chloride (0.3 mL) and NaOH (50%, 0.8 mL) using the procedure described in step 30a for 1 hour at room temperature.

MS (ESI) m/z 864/862 (M+H)$^+$. $^{13}$C-NMR (100 MHz, CDCl$_3$): δ 203.8, 173.7, 169.7, 169.2, 147.4, 141.7, 134.6, 118.6, 102.4, 102.1, 81.4, 75.4, 71.5, 70.9, 70.6, 70.4, 70.3, 67.2, 66.9, 53.4, 50.0, 44.9, 41.2, 39.7, 33.7, 32.9, 32.6, 31.0, 29.6, 29.5, 28.0, 25.3, 21.3, 21.2, 17.7, 17.2, 13.0, 9.7, 8.7.

Step 32b. Compound of Formula I: A=—CHO, $R_1$ and $R_2$ taken together=O, $R_3$=H, $R_4$=—C(O)$CH_3$, $R_5$=—(CH$_3$)$_2$Br and $R^P$=—C(O)$CH_3$;

The title compound is obtained from the compound of step 32a using the procedure described in step 28b.

Step 32c. Compound of Formula I: A=—CHO, $R_1$ and $R_2$ taken together=O, $R_3$=H, $R_4$=H, $R_5$=—(CH$_3$)$_2$Br and $R^P$=H.

The title compound is obtained from the compound of step 32b using the procedure described in step 1e.

Example 33

Compound of Formula I: A=—CHO, $R_1$ and $R_2$ taken together=O, $R_3$=H, $R_4$=H, $R_5$=—$CH_2CHCHCH_2Cl$ and $R^P$=H.

Step 33a. Compound of Formula I: A=—CH(OCH$_3$)$_2$, $R_1$ and $R_2$ taken together=O, $R_3$=H, $R_4$=—C(O)$CH_3$, $R_5$=-(trans-$CH_2CHCHCH_2Cl$) and $R^P$=—C(O)$CH_3$;

The title compound (17.6 mg, 15.7%) was obtained from the compound of step 1d (100.0 mg, 0.137 mmol), trans-1,4-dichloro-2-butene (145.2 μL, 1.37 mmol) and tetrabutylammonium iodide (25.4 mg, 0.069 mmol) in methylene chloride (0.3 mL) and NaOH (50%, 0.8 mL) using the procedure described in step 30a for 1 hour at room temperature.

MS (ESI) m/z 818/816 (M+H)$^+$. $^{13}$C-NMR (100 MHz, CDCl$_3$): δ 203.8, 173.7, 169.7, 169.3, 147.4, 141.6, 134.8, 130.8, 128.4, 118.7, 102.5, 102.1, 81.4, 75.3, 71.5, 71.0, 70.7, 70.6, 69.9, 67.3, 66.9, 53.5, 50.0, 45.0, 44.2, 41.2, 39.7, 33.9, 32.9, 32.6, 31.0, 29.7, 25.3, 21.3, 21.2, 17.8, 17.2, 13.0, 9.7, 8.7.

Step 33b. Compound of formula I: A=—CHO, R$_1$ and R$_2$ taken together=O, R$_3$=H, R$_4$=C(O)CH$_3$, R$_5$=-(trans-CH$_2$CHCHCH$_2$Cl) and R$^P$=—C(O)CH$_3$;

The title compound is obtained from the compound of step 33a using the procedure described in step 28b.

Step 33c. Compound of Formula I: A=—CHO, R$_1$ and R$_2$ taken together=O, R$_3$=H, R$_4$=H, R$_5$=-(trans-CH$_2$CHCHCH$_2$Cl) and R$^P$=H.

The title compound is obtained from the compound of step 33b using the procedure described in step 1e.

Example 34

Compound of formula I: A=—CHO, R$_1$ and R$_2$ taken together=O, R$_3$=H, R$_4$=H, R$_5$=—CH$_2$Phenyl and R$^P$=H.

Step 34a. Compound of Formula I: A=—CH(OCH$_3$)$_2$, R$_1$ and R$_2$ taken together=O, R$_3$=H, R$_4$=—C(O)CH$_3$, R$_5$=—CH$_2$-phenyl and R$^P$=—C(O)CH$_3$;

The title compound (58.6 mg, 71.6%) was obtained from the compound of step 1d (72.8 mg, 0.10 mmol), benzyl bromide (121.9 μL, 1.00 mmol) and tetrabutylammonium iodide (8.5 mg, 0.050 mmol) in methylene chloride (0.3 mL) and NaOH (50%, 0.8 mL) using the procedure described in step 29a for 2 hours at room temperature.

MS (ESI) m/z 818 (M+H)$^+$. $^{13}$C-NMR (100 MHz, CDCl$_3$): δ 203.8, 173.7, 169.7, 169.2, 147.5, 141.7, 137.8, 134.7, 128.4, 127.7, 127.5, 118.6, 102.4, 102.1, 81.4, 75.3, 73.3, 71.5, 70.9, 70.6, 69.5, 67.2, 66.8, 53.4, 50.0, 44.9, 41.2, 39.7, 32.9, 32.7, 31.0, 29.6, 25.2, 21.3, 21.2, 17.7, 17.2, 13.0, 9.6, 8.7.

Step 34b. Compound of Formula I: A=—CHO, R$_1$ and R$_2$ taken together=O, R$_3$=H, R$_4$=—C(O)CH$_3$, R$_5$=—CH$_2$-Phenyl and R$^P$=—C(O)CH$_3$;

The crude title compound was obtained from the compound of step 34a (17.2 mg, 22.4 μmol) using the procedure described in step 28b.

MS (ESI) m/z 772 (M+H)$^+$.

Step 34c. Compound of Formula I: A=—CHO, R$_1$ and R$_2$ taken together=O, R$_3$=H, R$_4$=H, R$_5$=—CH$_2$-Phenyl and R$^P$=H.

The title compound (14.0 mg, 97.9 % two steps) was obtained from the crude compound of step 34b using the procedure described in step 1e.

MS (ESI) m/z 688 (M+H)$^+$. $^{13}$C-NMR (100 MHz, CDCl$_3$): δ 203.2, 202.9, 174.0, 148.0, 142.0, 137.8, 134.9, 128.4, 127.7, 127.5, 118.7, 104.1, 81.1, 75.5, 73.4, 71.0, 70.8, 70.2, 69.7, 45.0, 44.6, 43.8, 41.7, 39.4, 32.7, 31.9, 29.6, 25.5, 17.8, 17.4, 13.0, 9.7, 8.9.

Example 35

Compound of Formula I: A=—CHO, R$_1$ and R$_2$ taken together=O, R$_3$=H, R$_4$=H, R$_5$=—CH$_2$CHCH$_2$ and R$^P$=H.

Step 35a Compound of Formula I; A=—CH(OCH$_3$)$_2$, R$_1$ and R$_2$ taken together=O, R$_3$=H, R$_4$=—C(O)CH$_3$, R$_5$=—CH$_2$CHCH$_2$ and R$^P$=—C(O)CH$_3$;

Method A: The title compound (54.2 mg, 51.4 %) was obtained from the compound of step 1d (100 mg, 0.14 mmol), 1,3-diiodopropane (157.8 μL, 1.37 mmol) and tetrabutylammonium iodide (25.4 mg, 0.069 mmol) in methylene chloride (0.3 mL) and NaOH (50%, 0.8 mL) using the procedure described in step 29a for 2 hours at room temperature.

MS (ESI) m/z 768 (M+H)$^+$. $^{13}$C-NMR (100 MHz, CDCl$_3$): δ 203.7, 173.7, 169.7, 169.2, 147.5, 141.8, 134.7, 134.3, 118.6, 117.2, 102.4, 102.1, 81.3, 75.4, 72.2, 71.5, 70.9, 70.6, 69.6, 67.2, 66.8, 60.3, 53.4, 50.0, 44.9, 41.2, 39.7, 32.9, 32.6, 31.0, 25.3, 21.3, 21.2, 17.7, 17.1, 13.0, 9.6, 8.7.

Method B: The title compound was obtained using the procedure described in step 29a from the compound of step Id (4.1 mg, 0.006 mmol), 1,3-dibromopropane (15 μL, 0.15 mmol) and tetrabutylammonium iodide (1.8 mg, 0.005 mmol) in methylene chloride (0.1 mL) and NaOH (50%, 0.1 mL) for 1 hour at room temperature.

MS (ESI) m/z 768 (M+H)$^+$.

Method C: A solution of the compound of step 1d (265 mg, 0.36 mmol), t-butyl allyl carbonate (115 mg, 0.73 mmol), 1,4-bis(diphenylphosphino)butane (31.0 mg, 0.072 mmol) and tris(dibenzylideneacetone)dipalladium (33.3 mg, 0.036 mmol) in degassed THF (5 mL) was heated at 68° C. for 45 minutes before evaporation. The residue was purified (silica, hexanes:ethyl acetate/4:1~1:1.5) to give the title compound (171.4 mg, 61.3%, its MS (ESI) and NMR ($^1$H, $^{13}$C) are identical to the compound obtained in step 35a Method A) and a side product (74.3 mg, 25.2%).

The side product (Compound of Formula I; A=—CH (OCH$_3$)$_2$, R$_1$ and R$_2$ taken together=O, R$_3$=—CH$_2$CHCH$_2$, R$_4$=—C(O)CH$_3$, R$_5$=—CH$_2$CHCH$_2$ and R$^P$=—C(O)CH$_3$;

MS (ESI) m/z 808 (M+H)$^+$. $^{13}$C-NMR (100 MHz, CDCl$_3$): δ 204.0, 171.8, 169.7, 169.2, 147.4, 142.1, 135.7, 134.3, 134.0, 119.0, 117.1, 115.0, 102.0, 100.7, 78.6, 75.5, 75.3, 72.2, 71.6, 71.4, 70.8, 70.4, 69.7, 67.2, 60.3, 53.6, 49.4, 44.9, 43.9, 41.2, 39.3, 36.5, 32.8, 31.5, 29.6, 25.3, 21.3, 21.2, 17.7, 17.2, 12.8, 9.6, 9.0.

Step 35b. Compound of Formula I: A=—CHO, R$_1$ and R$_2$ taken together=O, R$_3$=H, R$_4$=—C(O)CH$_3$, R$_5$=—CH$_2$CHCH$_2$ and R$^P$=—C(O)CH$_3$;

The crude title compound was obtained from the compound of step 35a (30.0 mg, 39 μmol) using the procedure described in step 28b.

Step 35c. Compound of Formula I: A=—CHO, R$_1$ and R$_2$ taken together=O, R$_3$=H, R$_4$=H, R$_5$=—CH$_2$CHCH$_2$ and R$^P$=H.

The title compound (24.9 mg, 100% two steps) was obtained from the crude compound of step 35b using the procedure described in step 1e.

MS (ESI) m/z 638 (M+H)$^+$. $^{13}$C-NMR (100 MHz, CDCl$_3$): δ 203.2, 202.9, 174.0, 148.0, 142.0, 134.8, 134.3, 118.7, 117.2, 104.0, 81.2, 75.5, 73.3, 72.2, 70.9, 70.7, 70.2, 69.8, 67.1, 45.0, 44.5, 43.7, 41.7, 39.4, 32.8, 31.9, 29.6, 25.6, 17.8, 17.5, 13.0, 9.7, 8.9.

Example 36

Compound of Formula I: A=—CHO, R$_1$ and R$_2$ taken together=O, R$_3$=—CH$_2$CHCH$_2$, R$_4$=H, R$_5$=—CH$_2$CHCH$_2$ and R$^P$=H.

Step 36a. Compound of Formula I: A=—CHO, R$_1$ and R$_2$ taken together=O, R$_3$=—CH$_2$CHCH$_2$, R$_4$=—C(O)CH$_3$, R$_5$=—CH$_2$CHCH$_2$ and R$^P$=—C(O)CH$_3$;

The crude title compound was obtained from a side product of step 35a Method C (30.0 mg, 37 μmol) using the procedure described in step 28b.

Step 36b. Compound of Formula I: A=—CHO, R$_1$ and R$_2$ taken together=O, R$_3$=—CH$_2$CHCH$_2$, R$_4$=H, R$_5$=—CH$_2$CHCH$_2$ and R$^P$=H.

The title compound (24.9 mg, 99% two steps) was obtained from the crude compound of step 36a using the procedure described in step 1e.

MS (ESI) m/z 678 (M+H)$^+$. $^{13}$C-NMR (100 MHz, CDCl$_3$): δ 203.4, 201.8, 171.7, 148.2, 142.7, 135.3, 134.3, 134.0, 118.6, 117.1, 115.8, 102.9, 79.2, 75.9, 75.3, 72.2, 72.2, 71.7, 71.1, 70.7, 70.3, 69.8, 44.9, 44.8, 44.1, 43.4, 41.7, 39.0, 35.1, 32.2, 29.6, 25.4, 17.8, 17.5, 12.8, 9.6, 9.5.

Example 37

Compound of Formula I: A=—CHO, $R_1$ and $R_2$ taken together=O, $R_3$=H, $R_4$ =H, $R_5$=-(trans-$CH_2CHCH$)-(3-quinolyl) and $R^P$=H.

Step 37a. Compound of formula I: A=—CH(OCH$_3$)$_2$, $R_1$ and $R_2$ taken together=O, $R_3$=H, $R_4$=—C(O)CH$_3$, $R_5$=-(trans-CH$_2$CHCH)-(3-quinolyl) and $R^P$=—C(O)CH$_3$;

The title compound (46.8 mg, 37.6%) was obtained as an inseparable 1:1 mixture with (E)-3-(3-quinolinyl)-2-propen-1-ol using the procedure described in step 35a (Method C) from a mixture of the compound of step 1d (101.3 mg, 0.14 mmol), 3-(t-butoxycarboxy)-3-(3-quinolinyl)-1-propene (54.6 mg, 0.19 mmol), 1,4-bis(diphenylphosphino)butane (11.9 mg, 0.028 mmol) and tris(dibenzylideneacetone) dipalladium (12.7 mg, 0.014 mmol) in degassed THF (5 mL). The mixture was heated at 68° C. for 1.5 hours after chromatography (silica, CH$_2$Cl$_2$:MeOH/99.5:0.5~98.5:1.5).

MS (ESI) m/z 863 (M–MeOH+H)$^+$, 574 (M–5-O-mycaminosyl-2',4'-diacetate-protection at C20)$^+$.

Step 37b. Compound of Formula I: A=—CHO, $R_1$ and $R_2$ taken together=O, $R_3$=H, $R_4$=—C(O)CH$_3$, $R_5$=-(trans-CH$_2$CHCH)-(3-quinolyl) and $R^P$=—C(O)CH$_3$;

The crude title compound was obtained from the compound of step 37a (46.8 mg 52.3 μmol) using the procedure described in step 28b.

MS (ESI) m/z 849 (M+H)$^+$, 574 (M–5-O-mycaminosyl-2',4'-diacetate)$^+$.

Step 37c. Compound of Formula I: A=—CHO, $R_1$ and $R_2$ taken together=O, $R_3$=H, $R_4$=H, $R_5$=-(trans-CH$_2$CHCH)-(3-quinolyl) and $R^P$=H.

The title compound (32.7 mg, 30.7% three steps) was obtained from the crude compound of step 37b using the procedure described in step 1e.

MS (ESI) m/z 765 (M+H)$^+$, 574 (M–5-O-mycaminosyl)$^+$. $^{13}$C-NMR (100 MHz, CDCl$_3$): δ 203.1, 202.9, 174.9, 149.2, 147.9, 141.8, 135.0, 132.7, 129.4, 129.3, 129.2, 128.9, 128.2, 128.0, 127.9, 127.0, 119.0, 104.1, 81.4, 75.4, 73.4, 71.8, 71.0, 70.8, 70.3, 70.1, 45.1, 44.5, 43.8, 41.7, 40.3, 39.4, 32.6, 31.9, 29.6, 25.6, 17.8, 17.3, 13.0, 9.7, 8.9.

Example 38

Compound of Formula I: A=—CHO, R1 and R2 taken together=O, R3=H, R4=-(trans-CH$_2$CHCH)-(3-quinolyl), $R_5$=CH$_3$, and $R^P$=H.

Step 38a. 10 of Scheme 1: $R_5$=CH$_3$, $R_4$=Ac, Rp$_3$=trimethylsilyl, $R^P$=Ac, and R' and R"=CH$_3$;

Into a solution of the crude compound of step 30a (1.6 g) in dichloromethane (4 mL) was added 1,1,1,3,3,3-hexamethyldisilazane (323 mg, 2 mmol) and 1-methylimidazole (246 mg, 3 mmol) at room temperature. It was stirred for 3 hours before additional 1,1,1,3,3,3-hexamethyldisilazane (323 mg, 2 mmol) and one drop of TMSCl were added. The mixture was stirred over night, quenched by saturated NaHCO$_3$ aqueous solution (200 mL) and extracted with ethyl acetate. The extract was washed with brine, dried (Na$_2$SO$_4$) and concentrated. Pure title compound (900 mg) was obtained by chromatography (silica, EtOAc:Hexanes/3:7).

MS (ESI) m/z 814 (M+H)$^+$.

Step 38b. 10 of Scheme 1: $R_5$=CH$_3$, $R_4$=H, Rp$_3$=trimethylsilyl, $R^P$=H, and R' and R"=CH$_3$.

The title compound (700 mg) was obtained from the compound of step 38a (800 mg, 0.98 mmol) in methanol (20 mL) at room temperature overnight using the procedure according to step 1e.

MS (ESI) m/z 730 (M+H)$^+$.

Step 38c. 10 of Scheme 1: $R_5$=CH$_3$, $R_4$=-(trans-CH$_2$CHCH)-(3-quinolyl), Rp$_3$=trimethylsilyl, $R^P$=H, and R' and R"=CH$_3$;

The title compound (53 mg) was obtained using the procedure described in step 35a (Method C) from a mixture of the compound of step 38b (235 mg, 0.32 mmol), 3-(t-butoxycarboxy)-3-(3-quinolinyl)-1-propene (110 mg, 0.40 mmol), 1,4-bis(diphenylphosphino)butane (32 mg, 0.07 mmol) and tris(dibenzylideneacetone)dipalladium (37 mg, 0.04 mmol) in degassed THF (4 mL) at 65° C. for 16 hours after chromatography.

MS (ESI) m/z 897 (M+H)$^+$.

Step 38d. Compound of Formula I: A=—CHO, $R_1$ and $R_2$ taken together=O, $R_3$=H, $R_4$=-(trans-CH$_2$CHCH)-(3-quinolyl) and $R^P$=H.

The title compound (9 mg) was obtained from the compound of step 38c using the procedure described in step 28b with HCl (1N, 1 mL) in acetonitrile (1 mL) after chromatography (silica, acetone:hexanes/2:8).

MS (ESI) m/z 779 (M+H)$^+$. $^{13}$C-NMR(100 MHz, CDCl$_3$): δ 203.4, 203.2,174.0, 149.2, 148.1, 147.6, 142.1, 134.9, 132.7, 129.4, 129.2, 128.8, 128.0, 127.9, 127.8, 127.0, 118.3, 103.6, 81.5, 79.7, 75.3, 73.0, 72.5, 71.7, 70.3, 69.8, 67.1, 59.2, 45.0(2), 43.8, 41.7, 40.8, 39.4, 32.5, 31.3, 29.7, 25.5, 18.2, 17.5, 13.0, 9.7, 8.8

Example 39

Compound of Formula I: A=—CHO, $R_1$ and $R_2$ taken together=O, $R_3$=H, $R_4$=-(trans-CH$_2$CHCH)-(3-quinolyl), $R_5$=CH$_2$-phenyl, and $R^P$=H.

Step 39a. 10 of Scheme 1: $R_5$=—CH$_2$-phenyl, $R_4$=Ac, Rp$_3$=trimethylsilyl, $R^P$=Ac, and R' and R"=CH$_3$;

A mixture of the compound of step 34a (0.8 g, 0.98 mmol), 1,1,1,3,3,3-hexamethyldisilazane (0.31 mL, 1.47 mmol), 1-methylimidazole (0.16 mL, 1.96 mmol) in dichloromethane (1.5 mL) was stirred for 6 hours at room temperature before partition (ethyl acetate/water). The organic was washed with water and brine and dried (Na$_2$SO$_4$). After concentration, the residue was chromatographed (silica, acetone:hexane/1:4) to give the title compound (0.27 g, 31%).

MS (ESI) m/z 890 (M+H)$^+$.

Step 39b. 10 of Scheme 1: $R_5$=—CH$_2$-phenyl, $R_4$=H, Rp$_3$=trimethylsilyl, $R^P$=H, and R' and R"=CH$_3$.

The title compound (240 mg, 100%) was obtained from the compound of step 39a (270 mg) in methanol (4 mL) at room temperature for 16 hrs using the procedure according to step 1e.

MS (ESI) m/z 806 (M+H)$^+$.

Step 39c. 10 of Scheme 1: $R_5$=—CH$_2$-phenyl, R4=-(trans-CH$_2$CHCH)-(3-quinolyl), Rp$_3$=trimethylsilyl, $R^P$=H, and R' and R"=CH$_3$;

The title compound (38 mg, 13%) was obtained using the procedure described in step 35a (Method C) from a mixture of the compound of step 39b (240 mg, 0.30 mmol), 3-(t-butoxycarboxy)-3-(3-quinolinyl)-1-propene (127.4 mg, 0.45 mmol), 1,4-bis(diphenylphosphino)butane (27.3 mg, 0.03 mmol) and tris(dibenzylideneacetone)dipalladium (25.4 mg, 0.06 mmol) in degassed THF (2 mL) at 68° C. for 3 hours after chromatography (silica, Acetone:Hexane/1:2).

MS (ESI) m/z 973 (M+H)$^+$.

Step 39d. Compound of Formula I: A=—CHO, $R_1$ and $R_2$ taken together=O, $R_3$=H, $R_4$=-(trans-CH$_2$CHCH)-(3-quinolyl), $R_5$=CH$_2$-phenyl and $R^P$=H.

The title compound (20 mg, 60%) was obtained from the compound of step 39c using the procedure described in step 28b with HCl (1N, 1 mL) in acetonitrile (1 mL) for 20 min after chromatography (silica, MeOH:CH$_2$Cl$_2$/50:1).

MS (ESI) m/z 854 (M+H)$^+$. $^{13}$C-NMR (100 MHz, CDCl$_3$): δ 203.4, 203.2, 174.0, 149.2, 148.2, 147.6, 142.2, 137.8, 134.8, 132.7, 129.4, 129.3, 129.2, 128.8, 128.4, 128.1, 127.9, 127.8, 127.7, 127.5, 127.0, 118.3, 103.6, 81.5, 79.7, 75.3, 73.4, 73.1, 71.7, 70.2, 69.8, 69.6, 45.0, 44.9, 43.8, 41,7, 40.8, 39.4, 32.4, 31.3, 29.7, 25.4, 18.2, 17.5, 13.0, 9.7, 8.8.

Example 40

Compound of Formula I: A=—CHO, R$_1$ and R$_2$ taken together=O, R$_3$=H, R$_4$=—CH$_2$CHCH$_2$, R$_5$=H and R$^P$=H.

Step 40a. Compound 1 of Scheme 1: R$_3$=H, R$^P$=Bz;

A mixture of tylosin (91.61 g, 0.10 mol) and benzoic anhydride (24.88 g, 0.11 mol) in acetone (210 mL) was stirred at room temperature for 15 hours before concentration. The residue was partitioned between ethyl acetate (700 mL) containing triethylamine (14.0 mL, 0.10 mol) and water (500 mL). The organic was washed with water and brine before drying (Na$_2$SO$_4$). Evaporation gave the title compound (103.90 g).

MS (ESI) m/z 1020 (M+H)$^+$.

Step 40b. Compound of Formula I: A=—CHO, R$_1$ and R$_2$ taken together=O, R$_3$=H, R$_4$=H, R$_5$=H and R$^P$=Bz;

A mixture of compound from step 40a (51.01 g, 50 mmol) and p-toluenesulfonic acid monohydrate (28.53 g, 150 mmol) in acetonitrile (200 mL) and water (50 mL) was refluxed for 6.5 hours before being cooled to room temperature. After concentration the residue was partitioned between methylene chloride (500 mL) and water (380 mL) containing sodium bicarbonate (16.80 g, 0.20 mol). The aqueous layer was washed with methylene chloride (200 mL). The combined organics were evaporated and chromatographed (silica, hexanes:acetone/9:1~1.5:1) to give the title compound (14.88 g, 42.4%).

MS (ESI) m/z 702 (M+H)$^+$. $^{13}$C-NMR (100 MHz, CDCl$_3$): δ 203.7, 203.1, 173.7, 164.6, 148.0, 141.9, 135.6, 133.1, 129.8, 129.7, 128.4, 118.2, 102.0, 100.9, 80.2, 74.8, 73.0, 70.5, 70.4, 69.4, 66.5, 62.1, 47.0, 44.9, 43.4, 41.2, 40.6, 39.2, 31.4, 31.1, 25.3, 17.8, 17.3, 13.0, 9.5, 8.6.

Step 40c. 10 of Scheme 1: Rp$_3$=H, R$_4$=H, R$_5$=H and R$^P$=Bz, R' and R"=CH$_3$;

To a solution of the compound of step 40b (3.64 g, 5.1 mmol) in methanol (30 mL) was added acetic chloride (0.44 mL, 6.1 mmol) at 0 ° C. The mixture was stirred for 1 hour and neutralized with triethylamine (0.5 mL) and concentrated. The residue was partitioned (ethyl acetate and saturated aqueous NaHCO$_3$). The organic was washed with water and brine, dried (Na$_2$SO$_4$). Evaporation provided the title compound (3.60 g, 95%).

MS (ESI) m/z 748 (M+H)$^+$. $^{13}$C-NMR (100 MHz, CDCl$_3$): δ 204.0, 173.6, 164.6, 147.3, 141.5, 135.8, 133.1, 129.9, 129.7, 128.4, 118.6, 102.3, 102.2, 80.5, 74.8, 72.9, 70.7, 70.5, 69.6, 66.7, 62.2, 53.6, 49.6, 47.1, 47.0, 44.9, 41.2, 39.6, 32.6, 30.8, 25.2, 17.8, 17.7, 13.0, 9.6, 8.8.

Step 40d. 10 of Scheme 1: Rp$_3$=H, R$_4$=H, R$_5$=OTBDPS and R$^P$=Bz, R' and R"=CH$_3$;

A mixture of the compound of step 40c (3.6 g, 4.811 mmol), imidazole (0.49 g, 7.2 mmol), TBDPSCl (1.1 mL, 6.3 mmol) in DMF (10 mL) was stirred at room temperature for 16 hours before partition (ethyl acetate and saturated aqueous NaHCO$_3$). The organics were washed with water and brine, dried (Na$_2$SO$_4$) and concentrated. Chromatography (silica, acetone:hexane/1:3) gave the title compound (1.50 g, 50%).

MS (ESI) m/z 986 (M+H)$^+$. $^{13}$C-NMR (100 MHz, CDCl$_3$): δ 203.8, 173.5, 164.6, 147.5, 141.9, 135.5, 135.4, 133.1, 133.0, 130.0, 129.8, 129.7, 128.4, 127.7, 118.5, 102.4, 80.7, 74.9, 73.0, 70.7, 70.5, 69.7, 66.8, 63.2, 53.4, 49.9, 46.9, 44.9, 41.2, 39.6, 32.7, 30.9, 26.7, 25.0, 19.1, 17.8, 12.9, 9.6, 8.8.

Step 40e. 10 of Scheme 1: Rp$_3$=H, R$_4$=—CH$_2$CHCH$_2$, R$_5$=TBDPSO and R$^P$=Bz, R' and R"=CH$_3$;

A solution of the compound of step 40d (0.9 g, 0.9 mmol), t-butyl allylcarbonate (217 mg, 1.4mmol), 1,4-bis (diphenylphosphino)butane (77.9 mg, 0.18 mmol), tris (dibenzylideneacetone)dipalladium (83.6 mg, 0.09 mmol) in degassed THF (5 mL) was heated at 68° C. for 4 hours before concentration. Chromatography (silica, ethyl acetate: hexane/:1:4) gave the title compound (450 mg, 49%) as a white solid.

MS (ESI) m/z 1026 (M+H)$^+$.

Step 40f. 10 of Scheme 1: Rp$_3$=H, R$_4$=CH$_2$CHCH$_2$, R$_5$=H and R$^P$=Bz, R' and R"=CH$_3$;

A mixture of the compound of step 40e (450 mg, 0.44 mmol), TBAF (1.0 M in THF, 0.88 mL, 0.88 mmol) in THF (2 mL) was stirred for 2 hours at room temperature before partition (ethyl acetate and saturated NaHCO$_3$). The organic was washed with water and brine, dried (Na$_2$SO$_4$) and evaporated to give the title compound (460 mg, 100%).

MS (ESI) m/z 788(M+H)$^+$.

Step 40g. Compound of Formula I: A=—CHO, R$_1$ and R$_2$ taken together=O, R$_3$=H, R$_4$=—CH$_2$CHCH$_2$, R$_5$=H and R$^P$=Bz, A solution of the compound from step 40f (460 mg) in CH$_3$CN (2 mL) was treated with HCl (0.3 N, 8 mL) for 1 hour at room temperature before partition (saturated NaHCO$_3$ and dichloromethane). The organic was dried (Na$_2$SO$_4$) and concentrated. Chromatography (silica, acetone:hexane/1:4) gave the title compound (174 mg, 54%).

MS (ESI) m/z 742 (M+H)$^+$. $^{13}$C-NMR (100 MHz, CDCl$_3$): δ 204.1, 203.6, 174.0, 165.1, 148.4, 142.4, 135.8, 135.2, 133.1, 130.5, 129.9, 128.5, 117.0, 102.0, 80.7, 79.4, 75.1, 73.3, 72.7, 71.3, 69.3, 66.8, 62.3, 47.3, 45.2, 43.7, 41.6, 40.8, 39.5, 34.8, 31.7, 25.5, 22.8, 18.2, 17.7, 14.3, 13.2, 9.8, 8.9.

Step 40h. Compound of Formula I: A=—CHO, R$_1$ and R$_2$ taken together=O, R$_3$=H, R$_4$=—CH$_2$CHCH$_2$, R$_5$=H and R$^P$=H.

A solution of the compound from step 40 g (25 mg) in MeOH (4 mL) was refluxed for 16 hours and concentrated. Chromatography (silica, acetone:hexane/1:3) gave the title compound (15 mg, 70%).

MS (ESI) m/z 638 (M+H)$^+$. $^{13}$C-NMR (100 m/z, CDCl$_3$): δ 203.6, 174.1, 148.1, 141.7, 136.4, 134.5, 117.3, 103.8, 81.6, 79.8, 75.0, 73.3, 72.6, 70.3, 69.9, 62.7, 47.5, 45.1, 43.9, 41.7, 41.1, 39.7, 32.5, 31.4, 31.1, 29.9, 29.4, 25.7, 18.3, 17.7, 13.3, 9.9, 8.9.

Example 41

Compound of Formula I: A=—CHO, R$_1$ and R$_2$ taken together=O, R$_3$=H, R$_4$=-(trans-CHCHCH$_2$)-(3-quinolyl), R$_5$=H and R$^P$=H.

Step 41a. Compound of Formula I: A=—CHO, R$_1$ and R$_2$ taken together=O, R$_3$=H, R$_4$=-(trans-CHCHCH$_2$)-(3-quinolyl), R$_5$=H and R$_p$=Bz;

A solution of the compound of step 40 g (150 mg, 0.2 mmol), 3-bromoquinoline (84 mg, 0.4 mmol), tri-o-tolyphosphine (18.5 mg, 0.06 mmol), triethyl amine (51.1 mg, 0.51 mmol), palladium (II) acetate (6.82 mg, 0.03 mmol) in degassed acetonitrile (1.2 mL) was heated at 80° C. for 16 hours and concentrated. Chromatography (silica, acetone:hexane/1:2) gave the title compound (138 mg, 80%).

MS (ESI) m/z 869 (M+H)$^+$.

Step 41b. Compound of Formula I: A=—CHO, R$_1$ and R$_2$ taken together=O, R$_3$=H, R$_4$=-(trans-CHCHCH$_2$)-(3-quinolyl), R$_5$=H and R$^P$=H.

A solution of the compound of step 41a (138 mg) in methanol (5 mL) was refluxed for 16 hours before evaporation. Chromatography (silica, acetone:hexane/1:1) gave the title compound (100 mg, 82%).

MS (ESI) m/z 765 (M+H)$^+$. $^{13}$C-NMR (100 MHz, CDCl$_3$): δ 203.3, 173.9, 151.9, 147.9, 146.7, 146.4, 141.6, 136.2, 133.9, 129.1, 128.6, 128.1, 127.2, 126.6, 118.5, 103.6, 82.3, 81.6, 74.8, 72.4, 69.6, 69.4, 62.5, 47.3, 44.9, 41.5, 40.9, 39.5, 30.9, 29.2, 27.7, 25.5, 17.5, 17.4, 13.1, 9.7, 8.7.

Example 42

Compound of Formula I: A=—CHO, R$_1$ and R$_2$ taken together=O, R$_3$=H, R$_4$=-(trans-CHCHCH$_2$)-(3-quinolyl), R$_5$=—C(O)NH-Phenyl and R$^P$=H.

Step 42a. Compound of Formula I: A=—CHO, R$_1$ and R$_2$ taken together=O, R$_3$=H, R$_4$=-(trans-CHCHCH$_2$)-(3-quinolyl), R$_5$=H and R$^P$=Ac;

A solution of the compound of step 41b (23.1 mg, 0.030 mmol) in acetone (4.0 mL) was treated with acetic anhydride (0.50 mL, 5.30 mmol) at room temperature for 2.5 hours before evaporation and partition (EtOAc and saturated NaHCO$_3$). The organic was washed with water and brine, dried (Na$_2$SO$_4$), and evaporated to give the crude title compound (24.4 mg, 100%).

MS (ESI) m/z 807 (M+H)$^+$.

Step 42b. Compound of Formula I: A=—CHO, R$_1$ and R$_2$ taken together=O, R$_3$=H, R$_4$=-(trans-CHCHCH$_2$)-(3-quinolyl), R$_5$=—C(O)NH-Phenyl and R$^P$=Ac;

A solution of the compound of step 42a (24.4 mg, 0.030 mmol) and triethylamine (21.1 μL, 0.15 mmol) in methylene chloride (2.0 mL) was treated with phenyl isocyanate (6.6 μL, 0.06 mmol) at room temperature for 1 hour before preparative thin-layer chromatography (silica, hexanes:EtOAc/1:1, three developments) to provide the title compound (4.2 mg, 15%).

MS (ESI) m/z 926 (M+H)$^+$.

Step 42c. Compound of Formula I: A=—CHO, R$_1$ and R$_2$ taken together=O, R$_3$=H, R$_4$=-(trans-CHCHCH$_2$)-(3-quinolyl), R$_5$=—C(O)NH-Phenyl and R$^P$=H.

A solution of the compound of step 42b (4.2 mg, 0.0045 mmol) in MeOH was kept at 50° C. for 18 hours before evaporation to provide the title compound (4.0 mg, 100%).

MS (ESI) m/z 884 (M+H)$^+$. $^{13}$C-NMR (100 MHz, CDCl$_3$): δ 203.2, 173.9, 153.0, 151.8, 147.7, 146.8, 146.1, 140.3, 137.5, 135.7, 133.9, 129.1, 128.7, 128.1, 127.2, 126.7, 118.5, 103.4, 82.0, 81.6, 74.4, 72.2, 69.5, 67.1, 45.0, 44.0, 43.8, 41.5, 40.9, 39.5, 32.3, 31.3, 29.7, 27.7, 25.3, 17.5, 13.0, 9.6, 8.7.

Example 43

Compound of Formula I: A=—CHO, R$_1$ and R$_2$ taken together=O, R$_3$=H, R$_4$=CH$_3$, R$_5$=H and R$^P$=H.

Step 43a. 10 of Scheme 1: Rp$_3$=H, R$_4$=H, R$_5$=TBS, R$^P$=Bz and R' R"=CH$_3$;

A solution of the compound from step 40c (8.678 g, 11.60 mmol), imidazole (1.185 g, 17.40 mmol) in DMF (35.0 mL) was treated with TBSCl (2.310 g, 15.32 mmol) at room temperature for 3 hours before partition (EtOAc and water). The organic was washed with water and brine, dried (Na$_2$SO$_4$), and evaporated. The title compound (7.010 g, 70%) was obtained by chromatography (silica, acetone:hexane/1:9~1:4).

MS (ESI) m/z 862 (M+H)$^+$. $^{13}$C-NMR (100 MHz, CDCl$_3$): δ 203.7, 173.4, 164.4, 147.4, 141.8, 134.3, 132.9, 129.8, 129.6, 128.2, 118.3, 102.2, 102.1, 80.4, 75.0, 72.8, 70.5, 70.4, 69.5, 66.5, 62.2, 53.2, 49.6, 46.5, 44.8, 41.1, 39.5, 32.6, 30.7, 30.6, 25.5, 24.9, 17.9, 17.6, 12.8, 9.5, 8.7, −5.7, −5.8.

Step 43b. Compound 10 of Scheme 1: Rp$_3$=TMS, R$_4$=TMS, R$_5$=TBS, R$^P$=Bz and R' and R"=CH$_3$;

A mixture of the compound of step 43a (7.00 g, 8.12 mmol), HMDS (2.57 mL, 12.18 mmol), 1-methylimidazole (1.30 mL, 16.31 mmol) in methylene chloride (30 mL) was stirred at room temperature for 14 hours before chromatography (silica, hexanes:EtOAc/95:5~85:15) to provide the title compound (6.161 g, 75.4%).

MS (ESI) m/z 1006 (M+H)$^+$. $^{13}$C-NMR (100 MHz, CDCl$_3$): δ 204.0, 171.2, 164.4, 147.3, 142.1, 133.9, 132.7, 130.4, 129.6, 128.2, 118.8, 101.6, 100.5, 77.7, 75.0, 73.7, 73.4, 71.1, 69.8, 68.2, 62.6, 53.6, 48.8, 46.8, 44.9, 44.6, 41.6, 36.7, 32.5, 31.8, 25.6, 25.0, 18.0, 17.9, 17.7, 12.7, 9.5, 8.6, 0.5, 0.2, −5.6, −5.7.

Step 43c. 10 of Scheme 1: Rp$_3$=TMS, R$_4$=H, R$_5$=TBS, R$^P$=Bz and R' and R"=CH$_3$;

A solution of the compound of step 43b (6.16 g, 6.12 mmol) in acetonitrile (27 mL) was treated with acetic acid (3.0 mL, 52.40 mmol) at room temperature for 2 hours. It was diluted with toluene and evaporated. The residual acetic acid was washed with more toluene and concentrated to give the title compound (5.890 g).

MS (ESI) m/z 934 (M+H)$^+$. $^{13}$C-NMR (100 MHz, CDCl$_3$): δ 203.6, 171.0, 164.2, 147.1, 141.9, 133.7, 132.8, 129.9, 129.5, 128.1, 118.8, 101.5, 100.4, 77.6, 74.8, 72.7, 70.3, 69.4, 68.3, 62.4, 53.4, 48.6, 46.6, 44.5, 41.2, 41.0, 36.8, 32.3, 31.7, 25.5, 24.9, 17.8, 17.6, 17.5, 12.5, 9.4, 8.5, 0.1, −5.8, −5.9.

Step 43d. 10 of Scheme 1: Rp$_3$=TMS, R$_4$=CH$_3$, R$_5$=TBS, R$^P$=Bz and R' and R"=CH$_3$;

A solution of the compound of step 43c (93.4 mg, 0.10 mmol) in THF (1.0 mL) was treated with sodium hydride (60 wt % in mineral oil, 12.8 mg, 0.32 mmol) at room temperature for 1 hour before methyl iodide (0.10 mL, 1.61 mmol) was added. The mixture was stirred at room temperature for 2.5 hours before partition (EtOAc and water). The organic was washed with water and brine, dried (Na$_2$SO$_4$) and evaporated. Chromatography (silica, hexane:EtOAc/9:1~4:1) afforded the title compound (63.4 mg, 66.9%).

MS (ESI) m/z 948 (M+H)$^+$. $^{13}$C-NMR (100 MHz, CDCl$_3$): δ 204.2, 171.3, 164.8, 147.4, 142.2, 134.0, 132.7, 130.6, 129.8, 128.2, 119.0, 101.8, 100.3, 81.4, 78.1, 75.2, 72.3, 71.0, 68.9, 68.5, 62.8, 59.8, 53.8, 49.2, 46.9, 44.7, 41.5, 37.0, 32.7, 32.0, 25.7, 25.2, 18.1, 17.9, 17.8, 12.8, 9.6, 8.8, 0.3, −5.5, −5.6.

Step 43e. Compound of Formula I: A=—CHO, R$_1$ and R$_2$ taken together=O, R$_3$=H, R$_4$=CH$_3$, R$_5$=H and R$^P$=H.

A solution of the compound from step 43d (63.4 mg, 0.067 mmol) in acetonitrile (1.2 mL) was treated with HCl (1.0 M, 0.80 mL, 0.80 mmol) at room temperature for 2 hours before partition (EtOAc and saturated NaHCO$_3$). The organic was washed with water and brine, dried (Na$_2$SO$_4$) and evaporated. MS (ESI) m/z 716 (M+H)$^+$.

The crude intermediate obtained above was treated with MeOH at room temperature for 100 hours before evaporation. Chromatography (silica, CH$_2$Cl$_2$:MeOH/99:1~98:2) afforded the title compound (35.8 mg, 87.5%).

MS (ESI) m/z 612 (M+H)$^+$. $^{13}$C-NMR (125 MHz, CDCl$_3$): δ 203.5, 203.4, 173.9, 148.0, 141.8, 136.0, 118.4, 103.5, 81.3, 74.8, 73.0, 69.9, 69.6, 68.1, 67.0, 62.4, 58.7, 47.2, 44.9, 43.7, 41.5, 40.9, 39.5, 32.4, 31.2, 25.4, 17.8, 17.5, 13.0, 9.6, 8.7.

Example 44

Compound of Formula I: A=—CHO, R$_1$ and R$_2$ taken together=O, R$_3$=—CH$_2$-phenyl, R$_5$=H and R$^P$=H.

Step 44a. 10 of Scheme 1: Rp$_3$=TMS, R$_4$=—CH$_2$-phenyl, R$_5$=TBS, R$^P$=Bz, and R' and R"=CH$_3$;

A solution of the compound of step 43c (93.4 mg, 0.10 mmol) in THF (1.0 mL) was treated with sodium hydride (60 wt % in mineral oil, 13.2 mg, 0.33 mmol) at room temperature for 1 hour before benzyl bromide (0.10 mL, 0.84 mmol) was added. The mixture was stirred at room temperature for 70 hours before partition (EtOAc and water). The organic was washed with water and brine, dried ($Na_2SO_4$) and evaporated. Chromatography (silica, hexane:EtOAc/95:5~85:15) afforded the title compound (38.5 mg, 37.6%).

MS (ESI) m/z 1024 $(M+H)^+$. $^{13}$C-NMR (100 MHz, $CDCl_3$): δ 204.3, 171.4, 164.7, 147.4, 142.3, 138.4, 134.1, 130.6, 129.8, 128.3, 128.2, 128.1, 127.7, 119.0, 101.8, 100.4, 79.4, 78.1, 75.2, 74.5, 72.3, 71.0, 69.4, 68.4, 62.8, 53.7, 49.1, 47.0, 44.7, 41.5, 36.9, 32.7, 32.0, 25.8, 25.2, 18.2, 18.1, 17.8, 12.8, 9.6, 8.8, 0.4, −5.5, −5.6.

Step 44b. Compound of Formula I: A=—CHO, $R_1$ and $R_2$ taken together=O, $R_3$=H, $R_4$=—$CH_2$-phenyl, $R_5$=H and $R^P$=H.

A solution of the compound of step 44a (38.5 mg, 0.037 mmol) in acetonitrile (1.2 mL) was treated with HCl (1.0 M, 0.80 mL, 0.80 mmol) at room temperature for 2.5 hours before partition (EtOAc and saturated $NaHCO_3$). The organic was washed with water and brine, dried ($Na_2SO_4$) and evaporated. MS (ESI) m/z 792 $(M+H)^+$.

The crude intermediate obtained above was treated with MeOH at room temperature for 76 hours before evaporation. Chromatography (silica, $CH_2Cl_2$:MeOH/99:1~98:2) afforded the title compound (19.0 mg, 73.6%).

MS (ESI) m/z 688 $(M+H)^+$. $^{13}$C-NMR (125 MHz, $CDCl_3$): δ 203.4, 203.3, 173.9, 147.9, 141.5, 136.2, 128.4, 128.3, 127.8, 127.7, 118.6, 103.6, 81.4, 79.5, 74.8, 73.2, 73.1, 70.1, 69.8, 67.1, 62.5, 47.3, 44.9, 43.8, 41.6, 40.9, 39.5, 32.4, 31.3, 29.7, 25.5, 18.1, 17.5, 13.1, 9.7, 8.7.

Example 45

Compound of Formula I: A=—CHO, $R_1$ and $R_2$ taken together=O, $R_3$=H, $R_4$=—$CH_2CCH$, $R_5$=H and $R^P$=H.

Step 45a. 10 of Scheme 1: $Rp_3$=TMS, $R_4$=—$CH_2CCH$, $R_5$=TBS, $R^P$=Bz and R' and R"=$CH_3$;

A solution of the compound of step 43c (467 mg, 0.50 mmol) in THF (3.0 mL) was treated with sodium hydride (60 wt % in mineral oil, 53.2 mg, 1.33 mmol) at room temperature for 1 hour before propargyl bromide (80 wt % in toluene, 0.40 mL, 3.60 mmol) was added. The mixture was stirred at room temperature for 5.5 hours before partition (EtOAc and water). The organic was washed with water and brine, dried ($Na_2SO_4$) and evaporated. Chromatography (silica, hexane:EtOAc/95:5~85:15) afforded the title compound (301 mg, 61.7%).

MS (ESI) m/z 972 $(M+H)^+$. $^{13}$C-NMR (100 MHz, $CDCl_3$): δ 204.1, 171.2, 164.6, 147.3, 142.2, 134.0, 132.8, 130.4, 129.8, 128.2, 119.0, 101.7, 100.3, 80.3, 77.9, 75.1, 74.4, 71.9, 70.8, 69.5, 68.5, 62.7, 60.2, 59.3, 53.7, 49.1, 46.9, 44.7, 41.5, 41.3, 37.0, 32.6, 32.0, 25.7, 25.1, 18.1, 18.0, 17.8, 12.8, 9.6, 8.7, 0.3, −5.5, −5.6.

Step 45b. Compound of Formula I: A=—CHO, $R_1$ and $R_2$ taken together=O, $R_3$=H, $R_4$=—$CH_2CCH$, $R_5$=H and $R^P$=H.

The compound of step 45a is deprotected using the procedure described in step 43e to provide the title compound.

Example 46

Compound of Formula I: A=—CHO, $R_1$ and $R_2$ taken together=O, $R_3$=H, $R_4$=—$CH_2CCH$, $R_5$=$CH_3$ and $R^P$=H.

Step 46a. 10 of Scheme 1: $Rp_3$=H, $R_4$=—$CH_2CCH$, $R_5$=H, $R^P$=Bz and R' and R"=$CH_3$;

A solution of the compound of step 45a (1.120 g, 1.15 mmol) in THF (10.0 mL) was treated with TBAF (1.0 M in THF, 3.0 mL, 3.00 mmol) at room temperature for 1 hour before partition (EtOAc and water). The organic was washed with water and brine, dried ($Na_2SO_4$) and evaporated to provide the crude title compound.

MS (ESI) m/z 786 $(M+H)^+$.

Step 46b. 10 of Scheme 1: $Rp_3$=H, $R_4$=—$CH_2CCH$, $R_5$=$CH_3$, $R^P$=Bz and R' and R"=$CH_3$;

A mixture of the crude compound of step 46a, tetra(n-butyl)ammonium iodide (213 mg, 0.58 mmol), methyl iodide (1.43 mL, 23.03 mmol) in methylene chloride (5.0 mL) and NaOH (50 wt %, 5.0 mL) was stirred at room temperature for 2 hours before partition (EtOAc and water). The organic was washed with water and brine, dried ($Na_2SO_4$) and evaporated. Chromatography (silica, hexane:EtOAc/95:5~85:15) afforded the title compound (650 mg, 70.5% for two steps).

MS (ESI) m/z 800 $(M+H)^+$. $^{13}$C-NMR (125 MHz, $CDCl_3$): δ 203.7, 173.6, 164.7, 147.4, 141.5, 134.8, 132.9, 130.3, 129.7, 128.3, 118.6, 102.3, 102.1, 80.9, 80.3, 77.6, 75.1, 74.4, 72.3, 72.0, 71.0, 69.6, 66.8, 59.2, 59.1, 53.6, 49.7, 44.9, 41.3, 39.6, 32.8, 32.6, 30.9, 25.3, 17.9, 17.7, 13.0, 9.6, 8.8.

Step 46c. Compound of Formula I: A=—CHO, $R_1$ and $R_2$ taken together=O, $R_3$=H, $R_4$=—$CH_2CCH$, $R_5$=$CH_3$ and $R^P$=H.

The compound of step 46b is deprotected using the procedure described in step 43e to provide the title compound.

Example 47

Compound of Formula I: A=—CHO, $R_1$ and $R_2$ taken together=O, $R_3$=H, $R_4$=2-fluoro-3-nitrobenzyl, $R_5$=CH, and $R^P$=H.

Step 47a. 10 of Scheme 1: $Rp_3$=H, $R_4$=$CH_3$, $R^P$=Bz and R' and R"=$CH_3$;

A mixture of the compound of step 40c (30.00 g, 40.1 mmol), tetra(n-butyl)ammonium iodide (1.48 g, 4.0 mmol), methyl iodide (20.0 mL, 0.32 mol) in methylene chloride (100 mL) and NaOH (50 wt %, 100 mL) was stirred at room temperature for 2 hours before evaporation. The residue was partitioned (EtOAc and water). The organic was washed with water and brine, dried ($Na_2SO_4$) and evaporated. Chromatography (silica, hexanes:acetone/9:1~3:1) provided the title compound (13.80 g, 45.1%).

MS (ESI) m/z 762 $(M+H)^+$. $^{13}$C-NMR (125 MHz, $CDCl_3$): δ 203.6, 173.5, 164.6, 147.3, 141.5, 134.7, 133.0, 129.9, 129.7, 128.3, 118.5, 102.3, 102.2, 80.5, 75.0, 72.9, 72.2, 70.6, 70.5, 69.6, 66.7, 59.0, 53.5, 49.5, 44.8, 41.4, 41.2, 39.5, 32.7, 30.7, 25.2, 25.1, 17.7, 12.9, 9.5, 8.7.

Step 47b. 10 of Scheme 1: $Rp_3$=TMS, $R_4$=TMS, $R_5$=$CH_3$, $R^P$=Bz and R' and R"=$CH_3$;

A mixture of the compound of step 47a (13.80 g, 18.11 mmol), HMDS (19.60 mL, 92.70 mmol), 1-methylimidazole (3.0 mL, 37.64 mmol), chlorotrimethylsilane (1.0 M in methylene chloride, 2.00 mL, 2.00 mmol) in methylene chloride (25 mL) was stirred at room temperature for 99 hours before evaporation. The residue was partitioned (hexanes:EtOAc/1:1 and water). The organic was washed with water and brine, dried ($Na_2SO_4$) and evaporated to give the crude title compound.

MS (ESI) m/z 906 $(M+H)^+$.

Step 47c. 10 of Scheme 1: $Rp_3$=TMS, $R_4$=H, $R_5$=$CH_3$, $R^P$=Bz and R' and R"=$CH_3$;

A solution of the crude compound of step 47c (18.11 mmol at most) in acetonitrile (90.0 mL) was treated with acetic acid (10.0 mL) at room temperature for 2 hours. It was diluted with toluene and evaporated. The residue acetic acid was chased by adding toluene and evaporation. Chromatography (silica, hexanes:acetone/95:5~85:15) provided the title compound (9.68 g, 45.1%).

MS (ESI) m/z 834 (M+H)$^+$.

Step 47d. 10 of Scheme 1: $Rp_3$=TMS, $R_4$=2-fluoro-4-nitrobenzyl, $R_5$=$CH_3$, $R^P$=Bz and R' and R"=$CH_3$;

Into a solution of the compound of step 47c (700 mg, 0.84 mmol) in THF (4 mL) at room temperature were added NaH (160 mg, 4.0 mmol) and 3,4-difluoronitrobenzene (636 mg, 4 mmol). The mixture was heated to 55° C. overnight before cooling to room temperature, poured over ice, extracted with ethyl acetate. The extract was washed with brine, dried ($Na_2SO_4$), filtered and evaporated. The residue was purified (silica, EtOAc:Hexane/3:7) to provide the title compound (613 mg, 75%).

MS (ESI) m/z 973 (M+H)$^+$. $^{13}$C-NMR(100 MHz, CDCl$_3$): δ 203.9, 171.5, 164.5, 153.0 (d), 150.9, 147.4, 142.0, 141.0 (d), 134.2, 130.1, 129.8, 128.4, 120.5 (d), 116.0, 112.6, 112.4, 101.8, 100.6, 80.2, 78.5, 75.1, 72.4, 71.3, 70.7, 68.6, 68.2, 59.1, 53.8, 45.0, 41.7, 41.1, 36.5, 32.7, 32.2, 25.3, 17.9, 17.8, 12.8, 9.6, 8.8, 0.4.

Step 47e. 10 of Scheme 1: $Rp_3$=TMS, $R_4$=2-fluoro-4-nitrobenzyl, $R_5$=$CH_3$, $R^P$=H and R' and R"=$CH_3$;

A solution of the compound of step 47d (40 mg) in methanol (2 mL) was heated at 55 ° C. for 4 days. Methanol was removed under reduced pressure to give the crude title compound (41 mg).

MS (ESI) m/z 869 (M+H)$^+$.

Step 47f. Compound of Formula I: A=—CHO, $R_1$ and $R_2$ taken together=O, $R_3$=H, $R_4$=2-fluoro-3-nitrobenzyl, $R_5$=$CH_3$ and $R^P$=H.

A solution of the crude compound of step 47e (41 mg) in THF (1 mL) was treated with 1N HCl (1 mL) at room temperature for 2 hours. It was quenched by saturated NaHCO$_3$. THF was removed under reduced pressure. The residue was extracted with chloroform. The extract was dried (Na$_2$SO$_4$) and concentrated. The residue was purified on silica gel (EtOAc:hexane/1:1) to give title compound (12 mg, 39% for two steps).

MS (ESI) m/z 751 (M+H)$^+$. $^{13}$C-NMR(100 MHz, CDCl$_3$): δ 203.1, 203.0, 174.0, 152.4, 151.7 (d), 150.4, 148.2, 142.1, 141.0 (d), 134.9, 120.7 (d), 118.3, 114.0, 113.1, 112.9, 103.6, 81.8, 78.2, 75.4, 72.5, 71.2, 69.9, 69.7, 59.2, 45.0, 41.7, 41.4, 39.4, 32.5, 31.4, 25.5, 17.7, 17.5, 13.0, 9.7, 8.8.

Example 48

Compound of Formula I: A=—CHO, $R_1$ and $R_2$ taken together=O, $R_3$=H, $R_4$=—CH$_2$CC-(2-thiophenyl)-(2-pyridyl), $R_5$=CH$_3$ and $R^P$=H.

Step 48a. 10 of Scheme 1: $Rp_3$=H, $R_4$=—CH$_2$CC-(2-thiophenyl)-(2-pyridyl), $R_5$=CH$_3$, $R^P$=Bz and R' and R"=CH$_3$;

A mixture of the compound from step 46b (60.0 mg, 0.075 mmol), dichlorobis(triphenylphosphine)palladium(II) (5.3 mg, 0.0075 mmol), copper(I) iodide (0.7 mg, 0.0038 mmol) in a degassed mixture of acetonitrile and triethylamine (4:1 v/v, 2.0 mL) was heated to 60° C. under nitrogen. It was stirred at 60° C. for 2 hours before evaporation. Chromatography (silica, EtOAc:hexane/4:1~1:1) provided the title compound (45.0 mg, 62.6%).

MS (ESI) m/z 959 (M+H)$^+$.

Step 48b. Compound of Formula I: A=—CHO, $R_1$ and $R_2$ taken together=O, $R_3$=H, $R_4$=—CH$_2$CC-(2-thiophenyl)-(2-pyridyl), $R_5$=CH$_3$ and $R^P$=Bz;

A solution of the compound of step 48a (45.0 mg, 0.047 mmol) in acetonitrile (1.0 mL) was treated with HCl (1 M, 1.0 mL) at room temperature for 1 hour before partition (EtOAc and water). The organic was washed with water and brine, dried (Na$_2$SO$_4$) and evaporated. The crude title compound (42.8 mg, 100%) was used directly for step 48c.

MS (ESI) m/z 913 (M+H)$^+$.

Step 48c. Compound of Formula I: A=—CHO, $R_1$ and $R_2$ taken together=O, $R_3$=H, $R_4$=—CH$_2$CC-(2-thiophenyl)-(2-pyridyl), $R_5$=CH$_3$ and $R^P$=H.

A solution of the crude product of step 48b (42.8 mg, 0.047 mmol) in MeOH was stirred at room temperature for 140 hours before evaporation. Chromatography (silica, CH$_2$Cl$_2$:MeOH/99:1~97:3) provided the title compound (11.2 mg, 29.6%).

MS (ESI) m/z 809 (M+H)$^+$. $^{13}$C-NMR (125 MHz, CDCl$_3$): δ 203.3, 203.2, 173.9, 151.8, 149.7, 148.1, 146.4, 142.1, 136.7, 134.9, 133.4, 128.3, 124.1, 123.9, 122.4, 118.8, 118.3, 103.6, 90.4, 81.4, 80.5, 78.8, 75.3, 72.9, 72.5, 70.2, 69.9, 67.2, 59.5, 59.2, 45.0, 44.9, 43.8, 41.5, 40.8, 39.4, 32.4, 31.3, 29.7, 25.5, 18.3, 17.5, 13.0, 9.7, 8.8.

Example 49

Compound of Formula I: A=—CHO, $R_1$ and $R_2$ taken together=O, $R_3$=H, $R_4$=—CH$_2$CC-(3-quinolyl), $R_5$=CH$_3$ and $R^P$=H.

Step 49a. 10 of Scheme 1: $Rp_3$=H, $R_4$=—CH$_2$CC-(3-quinolyl). $R_5$=CH$_3$, $R^P$=Bz and R' and R"=CH$_3$;

A solution of the compound of step 46b (50 mg, 0.06 mmol), 3-bromoquinoline (19.5 mg, 0.09 mmol), dichlorobis(triphenyl-phosphine)palladium (II) (4.2 mg, 0.006 mmol), copper iodide (0.6 mg, 0.003 mmol) in degassed acetonitrile (1.2 mL) and triethylamine (0.3 mL) was heated at 60° C. for 2 hours and concentrated. Chromatography (silica, acetone:hexane/1:5) gave the title compound (31 mg, 53%)

MS (ESI) m/z 927 (M+H)$^+$.

Step 49b. Compound of Formula I: A=—CHO, $R_1$ and $R_2$ taken together=O, $R_3$=H, $R_4$=—CH$_2$CC-(3-quinolyl) $R_5$=CH$_3$ and $R^P$=Bz;

A solution of the compound of step 49a (31 mg) in CH$_3$CN (1 mL) was treated with 1 N HCl aqueous solution (1 mL). The mixture was stirred for 20 minues at room temperature, neutralized with saturated aqueous NaHCO$_3$ and extracted with ethyl acetate. The organic solution was dried over anhydrous Na$_2$SO$_4$ and concentrated under vacuum to give the title compound (31 mg, 98%)

MS (ESI) m/z 881(M+H)$^+$.

Step 49c. Compound of Formula I: A=—CHO, $R_1$ and $R_2$ taken together=O, $R_3$=H, $R_4$=—CH$_2$CC-(3-quinolyl), $R_5$=CH$_3$ and $R^P$=H.

A solution of the compound of step 49b (31 mg) in methanol (3 mL) was stirred at room temperature for 5 days. The solvent was evaporated under vacuum. Purification on silica gel column (eluting with acetone:hexane/1:4) gave the title compound (18 mg, 66%).

MS (ESI) m/z 777 (M+H)$^+$. $^{13}$C-NMR (100 MHz, CDCl$_3$): δ 203.5, 203.4, 174.2, 152.2, 148.4, 147.3, 142.3, 138.9, 135.2, 131.1, 130.6, 129.7, 129.1, 127.9, 127.7, 127.3, 118.6, 116.7, 103.8, 81.8, 79.5, 75.6, 73.0, 72.8, 70.2, 66.4, 59.7, 59.4, 45.3, 45.2, 44.0, 41.8, 41.0, 39.7, 32.7, 30.0, 29.9, 25.8, 18.6, 17.7, 14.6, 13.3, 9.9, 9.0.

Example 50

Compound of Formula I: A=—CHO, $R_1$ and $R_2$ taken together=O, $R_3$=H, $R_4$=—CH$_2$CC-(5-pyrimidyl), $R_5$=CH$_3$ and $R^P$=H.

The compound from step 46b (50 mg) was processed as described in steps 49a, 49b and 49c of Example 49, substituting 5-bromopyrimidine for 3-bromoquinoline to provide the title compound (4.4 mg, 13% for three steps) as a white solid.

MS (ESI) m/z 728 (M+H)⁺. ¹³C-NMR (100 MHz, CDCl₃): δ 203.5, 203.3, 174.2, 159.1, 157.4, 148.4, 142.3, 139.5, 135.1, 118.6, 103.9, 81.8, 79.8, 75.6, 72.9, 72.8, 70.2, 67.6, 59.5, 59.4, 45.3, 45.1, 44.0, 41.8, 39.7, 39.1, 32.1, 31.8, 31.1, 29.9, 25.8, 22.9, 18.5, 17.7, 14.3, 13.2, 9.9, 9.1.

Example 51

Compound of Formula I: A=—CHO, R₁ and R₂ taken together=O, R₃=H, R₄=—CH₂CC-(3-pyridinyl), R₅=CH, and Rᴾ=H.

The compound from step 46b (50 mg) was processed as described in steps 49a, 49c and 49b of Example 49, substituting 3-bromopyridine for 3-bromoquinoline to provide the title compound (9.8 mg, 21% for three steps) as a white solid.

MS (ESI) m/z 727(M+H)⁺. ¹³C-NMR (100 MHz, CDCl₃): δ 202.3, 202.1, 173.0, 151.3, 147.9, 147.1, 141.1, 137.6, 133.9, 122.1, 117.3, 102.6, 87.6, 82.3, 80.5, 78.2, 75.5, 75.3, 74.3, 71.8, 71.5, 69.1, 68.9, 66.2, 58.3, 58.2, 44.0, 43.9, 42.7, 40.5, 39.7, 38.4, 31.5, 28.7, 28.6, 24.5, 21.7, 17.2, 16.5, 13.1, 12.0, 8.7, 7.8.

Example 52

Compound of Formula I: A=—CHO, R₁ and R₂ taken together=O, R₃=H, R₄=-(cis-CH₂CHCH)-(5-pyrimidinyl), R₅=CH₃ and Rᴾ=H.

Step 52a. 10 of Scheme 1: Rp₃=H, R₄=-(cis-CH₂CHCH)-(5-pyrimidyl), R₅=CH₃, Rᴾ=Bz and R' and R"=CH₃;

A mixture of the compound of step 50a (79.0 mg, 0.090 mmol), Lindlar catalyst (5 wt % Pd/CaCO₃, poisoned with lead, 38.0 mg, 0.018 mmol) and 6-methylquinoline (11.7 μL, 0.087 mmol) in EtOAc (5.0 mL) was equipped with a hydrogen balloon and stirred at room temperature for 5 hours before filtration and washing with more EtOAc. The conbined organic was evaporated. The residue was chromatographed (silica, hexanes:acetone/4:1) to provide the title compound (75.7 mg, 95.6%).

MS (ESI) m/z 880 (M+H)⁺. ¹³C-NMR (125 MHz, CDCl₃): δ 203.6, 173.6, 164.7, 157.0, 156.2, 147.3, 141.5, 134.8, 133.2, 132.9, 130.2, 130.1, 129.7, 128.3, 124.5, 118.5, 102.3, 102.1, 80.9, 79.9, 75.1, 72.3, 72.1, 71.0, 69.3, 68.3, 66.8, 59.1, 53.6, 49.7, 44.9, 41.3, 41.1, 39.5, 32.8, 32.6, 30.9, 25.3, 18.0, 17.7, 13.0, 9.6, 8.8.

Step 52b. 10 of Scheme 1: Rp₃=H, R₄=-(cis-CH₂CHCH)-(5-pyrimidyl), R₅=CH₃, Rᴾ=H and R' and R"=CH₃;

A solution of the compound of step 52a (75.7 mg, 0.086 mmol) in MeOH (3.0 mL) was heated at 66° C. for 70 hours before evaporation. The residue was chromatographed (silica, hexanes:acetone/1.5:1) to provide the title compound (58.4 mg, 87.6%).

MS (ESI) m/z 776 (M+H)⁺.

Step 52c. Compound of Formula I: A=—CHO, R₁ and R₂ taken together=O, R₃=H, R₄=-(cis-CH₂CHCH)-(5-pyrimidyl), R₅=CH₃ and Rᴾ=H.

A solution of the compound of step 52b (28.0 mg, 0.036 mmol) in MeCN (1.40 mL) was treated with HCl (1.0 M, 0.60 mL) at room temperature for 1 hour before partition (EtOAc and water). The organic was washed with water and brine, dried (Na₂SO₄) and evaporated to provide the title compound (26.2 mg, 99.6%).

MS (ESI) m/z 730 (M+H)⁺. ¹³C-NMR (125 MHz, CDCl₃): δ 203.2, 203.1, 173.9, 157.1, 156.1, 148.1, 142.0, 134.9, 133.3, 130.1, 123.9, 118.3, 103.5, 81.4, 80.2, 75.3, 72.7, 72.5, 70.1, 69.9, 67.9, 67.2, 59.2, 45.0, 44.9, 43.7, 41.6, 40.7, 39.4, 32.4, 31.3, 29.6, 25.5, 18.1, 17.7, 13.0, 9.7, 8.8.

Example 53

Compound of Formula I: A=—CHO, R₁ and R₂ taken together=O, R₃=H, R₄=—CH₂CH₂CH₂-(5-pyrimidyl), R₅=CH₃ and Rᴾ=H.

Step 53a. 10 of Scheme 1: Rp₃=H, R₄=—CH₂CH₂CH₂-(5-pyrimidyl), R₅=CH₃, Rᴾ=Bz and R' and R"=CH₃;

A solution of the compound of step 50a (40mg), Lindlar catalyst (5 wt % Pd/CaCO₃, poisoned with lead, 40 mg) in ethyl acetate (2 mL) was equipped with a hydrogen balloon and stirred at room temperature for 16 hours before filtration and washing with more EtOAc. The conbined organic was evaporated to provide the title compound (40 mg).

MS (ESI) m/z 882 (M+H)⁺.

Step 53b. 10 of Scheme 1: Rp₃=H, R₄=—CH₂CH₂CH₂-(5-pyrimidyl), R₅=CH₃, Rᴾ=H and R' and R"=CH₃;

A solution of the compound of step 53a (40 mg) in methanol (3 mL) was stirred at 60° C. for 48 hours. The solvent was evaporated to provide the title compound (40 mg).

MS (ESI) m/z 778 (M+H)⁺.

Step 53c. Compound of Formula I: A=—CHO, R₁ and R₂ taken together=O, R₃=H, R₄=—CH₂CH₂CH₂-(5-pyrimidinyl), R₅=CH₃ and Rᴾ=H.

A solution of the compound of step 53b (40 mg) in CH₃CN (4 mL) was added 1 N HCl aqueous solution (1 mL). The mixture was stirred for 1 hour at room temperature, neutralized with saturated aqueous NaHCO₃ and extracted with ethyl acetate. The organic was dried over anhydrous Na₂SO₄ and evaporated. Purification on silica gel (acetone:hexane/1:3) gave the title compound (19 mg, 57%).

MS (ESI) m/z 732 (M+H)⁺. ¹³C-NMR (100 MHz, CDCl₃): δ 203.6, 203.4, 174.2, 157.1, 156.9, 148.4, 142.3, 134.9, 131.1, 129.0, 103.8, 81.7, 80.2, 75.5, 73.3, 72.7, 70.4, 70.3, 70.0, 59.5, 45.3, 45.2, 43.9, 41.9, 41.1, 39.7, 31.7, 29.9, 27.4, 25.8, 18.4, 17.8, 13.2, 9.9, 9.0.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the Formula:

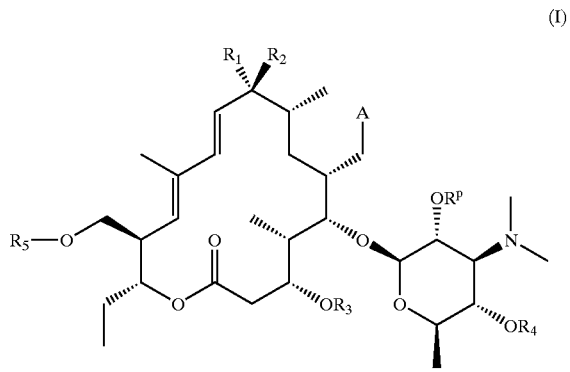

(I)

wherein
A is selected from the group consisting of:
(1) —CHO or a protected aldehyde;
(2) —CN;
(3) —CH=N—NR₆R₇, wherein R₆ and R₇ are each independently selected from the group consisting of:
(a) hydrogen;
(b) C₁–C₆-alkyl, optionally substituted with one or more substituents selected from the group consisting of: halogen, aryl, substituted aryl, heterocyclic, and substituted heterocyclic;
(c) C₂–C₆-alkenyl, optionally substituted with one or more substituents selected from the group consisting of: halogen, aryl, substituted aryl, heterocyclic, and substituted heterocyclic;
(d) $C_2$–$C_6$-alkynyl, optionally substituted with one or more substituents selected from the group consisting of: halogen, aryl, substituted aryl, heterocyclic, and substituted heterocyclic; and
(e) $R_6$ and $R_7$, taken together with the nitrogen atom to which they are connected, form a 3- to 7-membered ring which may optionally contain a hetero-function selected from the group consisting of: —O—, —NH—, —N($C_1$–$C_6$-alkyl)-, —N(aryl)-, —N(heteroaryl)-, —S—, —S(O)—, and —S(O)2—;
(4) —CH=N—$OR_6$;
(5) —$CH_2$X, wherein X is selected from the group consisting of:
 (a) hydroxy or protected hydroxy;
 (b) halogen;
 (c) —$NR_6R_7$;
 (d) —$NR_6$C(O)—$R_8$, $R_8$ is selected from the group consisting of:
  i. hydrogen;
  ii. $C_1$–$C_6$-alkyl, optionally substituted with one or more substituents selected from the group consisting of: halogen, aryl, substituted aryl, heterocyclic, and substituted heterocyclic;
  iii. $C_2$–$C_6$-alkenyl, optionally substituted with one or more substituents selected from the group consisting of: halogen, aryl, substituted aryl, heterocyclic, and substituted heterocyclic;
  iv. $C_2$–$C_6$-alkynyl, optionally substituted with one or more substituents selected from the group consisting of: halogen, aryl, substituted aryl, heterocyclic, and substituted heterocyclic;
  v. aryl;
  vi. substituted aryl;
  vii. heterocyclic; and
  viii. substituted heterocyclic;
 (e) —$NR_6$C(O)—$NR_7R_8$;
 (f) —$NR_6$—$NR_7R_8$;
 (g) —$NR_6$—$NR_7$C(O)—$R_8$;
 (h) —S(O)$_n$—$R_9$, where $R_9$ is selected from the group consisting of: aryl, substituted aryl, heterocyclic, and substituted heterocyclic, where n=0, 1 or 2;
 (i) —S(O)$_n$—($C_1$–$C_6$-alkyl), optionally substituted with one or more substituents selected from the group consisting of: aryl, substituted aryl, heterocyclic, and substituted heterocyclic;
 (j) —S(O)$_n$—($C_2$–$C_6$-alkenyl), optionally substituted with one or more substituents selected from the group consisting of: aryl, substituted aryl, heterocyclic, and substituted heterocyclic;
 (k) —S(O)$_n$—($C_2$–$C_6$-alkynyl), optionally substituted with one or more substituents selected from the group consisting of: aryl, substituted aryl, heterocyclic, and substituted heterocyclic; and
 (l) —O—M—Y, where M is:
  i. absent,
  ii. —C(O)—,
  iii. —C(O)N($R_6$),
  iv. $C_1$–$C_6$-alkyl-N($R_6$),
  v. $C_2$–$C_6$-alkenyl-N($R_6$)—, or
  vi. $C_2$–$C_6$-alkynyl-N($R_6$)—,
 and where Y is:
  i. hydrogen,
  ii. $C_1$–$C_6$-alkyl, optionally substituted with one or more substituents selected from the group consisting of: halogen, —$OR_6$, aryl, substituted aryl, heterocyclic, and substituted heterocyclic,
  iii. $C_2$–$C_6$-alkenyl, optionally substituted with one or more substituents selected from the group consisting of: halogen, —$OR_6$, aryl, substituted aryl, heterocyclic, and substituted heterocyclic,
  iv. $C_2$–$C_6$-alkynyl, optionally substituted with one or more substituents selected from the group consisting of: halogen, —$OR_6$, aryl, substituted aryl, heterocyclic, and substituted heterocyclic,
  v. aryl,
  vi. substituted aryl,
  vii. heterocyclic, or
  viii. substituted heterocyclic; and
 (6) heterocyclic or substituted heterocyclic;
$R_1$ and $R_2$ are each independently selected from the group consisting of:
 (1) hydrogen;
 (2) hydroxy;
 (3) protected hydroxy;
 (4) —OC(O)—$C_1$–$C_{12}$-alkyl, optionally substituted with one or more substituents selected from the group consisting of: halogen, aryl, substituted aryl, heterocyclic, substituted heterocyclic, —$OR_6$, and —$NR_6R_7$;
 (5) —$OR_6$;
 (6) halogen;
 (7) —$NR_6R_7$; and
 (8) $R_1$ and $R_2$ taken together are oxo;
$R_3$ is selected from the group consisting of:
 (1) hydrogen;
 (2) a hydroxy protecting group;
 (3) —C(O)—$C_1$–$C_{12}$-alkyl, optionally substituted with one or more substituents selected from the group consisting of: halogen, aryl, substituted aryl, heterocyclic, substituted heterocyclic, —$OR_6$, and —$NR_6R_7$;
 (4) $C_1$–$C_6$-alkyl, optionally substituted with one or more substituents selected from the group consisting of: halogen, aryl, substituted aryl, heterocyclic, substituted heterocyclic, —$OR_6$, and —$NR_6R_7$;
 (5) $C_2$–$C_6$-alkenyl, optionally substituted with one or more substituents selected from the group consisting of: halogen, aryl, substituted aryl, heterocyclic, substituted heterocyclic, —$OR_6$, and —$NR_6R_7$; and
 (6) $C_2$–$C_6$-alkynyl, optionally substituted with one or more substitutents selected from the group consisting of: halogen, aryl, substituted aryl, heterocyclic, substituted heterocyclic, —$OR_6$, and —$NR_6R_7$;
$R_4$ is —M—Y; provided that when M is absent Y can not be mycarosyl or substituted mycarosyl
$R_5$ is —M—Y; provided that at least one of $R_3$, $R_4$ and $R_5$ can not be hydrogen or an ester when the remaining of $R_3$, $R_4$ and $R_5$ are hydrogen; and
$R^p$ is hydrogen or a hydroxy protecting group.
2. A compound according to claim 1 wherein in Formula I, $R_3$ is selected from the group consisting of:
 (1) $C_1$–$C_6$-alkyl, optionally substituted with one or more substituents selected from the group consisting of: halogen, aryl, substituted aryl, heterocyclic, substituted heterocyclic, —O—$R_6$ and —$NR_6R_7$;

(2) $C_2$–$C_6$-alkenyl, optionally substituted with one or more substituents selected from the group consisting of: halogen, aryl, substituted aryl, heterocyclic, substituted heterocyclic, —O—$R_6$ and —$NR_6R_7$; and (3) $C_2$–$C_6$-alkynyl, optionally substituted with one or more substituents selected from the group consisting of: halogen, aryl, substituted aryl, heterocyclic, substituted heterocyclic, —O—$R_6$ and —$NR_6R_7$.

3. A compound according to claim 2 wherein in Formula I, $R_1$ and $R_2$ taken together are=O.

4. A compound according to claim 3 wherein in Formula I, $R_4$ is hydrogen.

5. A compound according to claim 1 wherein in Formula I, $R_4$ is selected from the group consisting of:

(1) $C_1$–$C_6$-alkyl, optionally substituted with one or more substituents selected from the group consisting of: halogen, aryl, substituted aryl, heterocyclic, substituted heterocyclic, —O—$R_6$ and —$NR_6R_7$;

(2) $C_2$–$C_6$-alkenyl, optionally substituted with one or more substituents selected from the group consisting of halogen, aryl, substituted aryl, heterocyclic, substituted heterocyclic, —O—$R_6$ and —$NR_6R_7$; and (3) $C_2$–$C_6$-alkynyl, optionally substituted with one or more substituents selected from the group consisting of halogen, aryl, substituted aryl, heterocyclic, substituted heterocyclic, —O—$R_6$ and —$NR_6R_7$.

6. A compound according to claim 5 wherein in Formula I, $R_1$ and $R_2$ taken together are=O.

7. A compound according to claim 6 wherein in Formula I, $R_3$ is hydrogen.

8. A compound according to claim 1 wherein in Formula I, $R_5$ is selected from the group consisting of:

(1) $C_1$–$C_6$-alkyl, optionally substituted with one or more substituents selected from the group consisting of: halogen, aryl, substituted aryl, heterocyclic, substituted heterocyclic, —O—$R_6$ and —$NR_6R_7$;

(2) $C_2$–$C_6$-alkenyl, optionally substituted with one or more substituents selected from the group consisting of halogen, aryl, substituted aryl, heterocyclic, substituted heterocyclic, —O—$R_6$ and —$NR_6R_7$; and (3) $C_2$–$C_6$-alkynyl, optionally substituted with one or more substituents selected from the group consisting of halogen, aryl, substituted aryl, heterocyclic, substituted heterocyclic, —O—$R_6$ and —$NR_6R_7$, wherein $R_6$ and $R_7$ are as previously defined.

9. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

10. A method for treating bacterial infections comprising administering to an animal in need of such treatment a pharmaceutical composition containing a therapeutically-effective amount of a compound of claim 1 or a pharmaceutically acceptable salt, ester or prodrug thereof.

11. A process for the preparation of a compound represented by Formula I as defined in claim 1 comprising:

(1) reacting a compound represented by the formula:

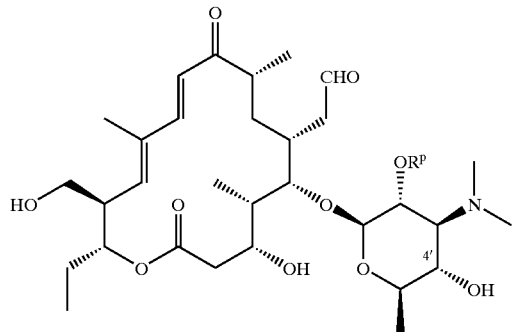

wherein $R^P$ is a hydroxy protecting group, with:
 i. an acetalating agent at a pH between 1 to 4 in an alcoholic solvent; and
 ii. treating with one or more silylating agent(s), optionally with the addition of a catalyst in an aprotic solvent at a temperature between 0° C. and 50° C. for 1 to 48 hours;

to provide a compound represented by the formula:

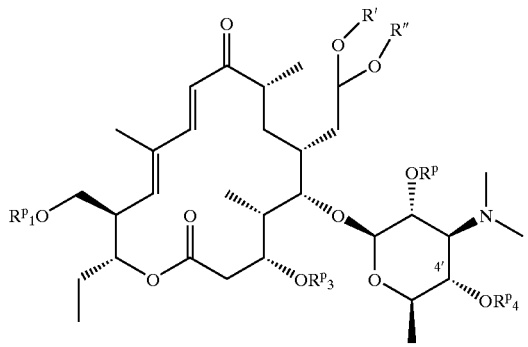

wherein $R^P_1$, $R^P_3$ and $R^P_4$ are each a hydroxy protecting group, and R' and R" are each $C_1$–$C_6$-alkyl or when taken together are —$CH_2CH_2$— or —$CH_2CH_2CH_2$—;

(2) treating the compound from step (1) with an acid in an organic solvent at a temperature between 0° C. and 50° C. for 1 to 24 hours to provide a compound represented by the formula:

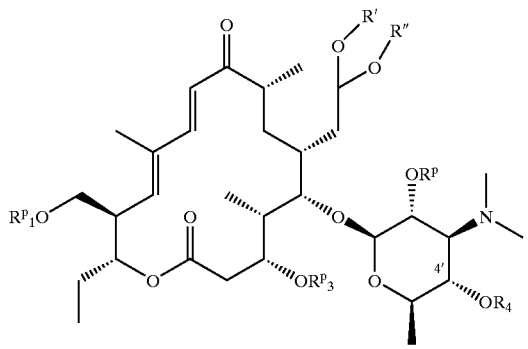

(3) reacting the compound from step (2) with an alkylating agent represented by the formula $R_4X$, wherein X is a halogen or sulphonyl group and $R_4$ is as defined in claim 1, in the presence of a base in an aprotic solvent at a temperature between −20° C. and 60° C., and then treating with an acid in an organic solvent at a temperature between room temperature and 100° C. for 1 to 48 hours to provide a compound represented by the formula:

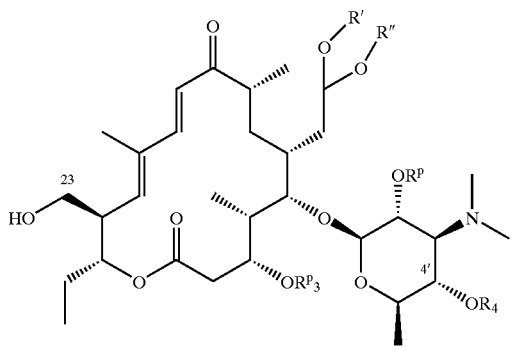

and (4) reacting the compound from step (3) with an alkylating agent in an aprotic solvent at a temperature between −20° C. and 100° C. in the presence of a base, optionally in the presence of water and a phase transfer catalyst, to provide a compound represented by the formula:

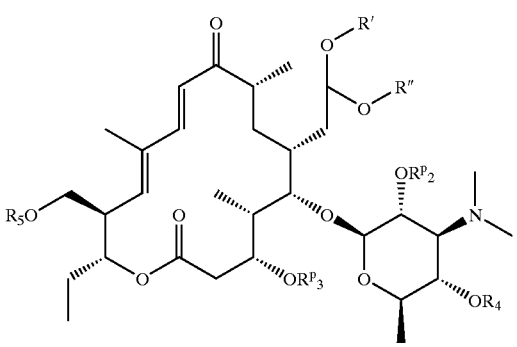

optionally deprotecting the compound from step (4) by:
i. treating with an aqueous acid in an organic solvent at a temperature from 0° C. to 100° C. for 1 to 24 hours; and
ii. stirring in methanol at a temperature between room temperature and reflux temperature for 4 to 24 hours;
to provide a compound represented by Formula I where A is —CHO, $R_1$ and $R_2$ taken together are=O, $R_3$ is hydrogen and $R_4$, $R_5$.

12. A process for the preparation of a compound represented by Formula I as defined in claim 1 comprising:
(1) reacting a compound represented by the formula:

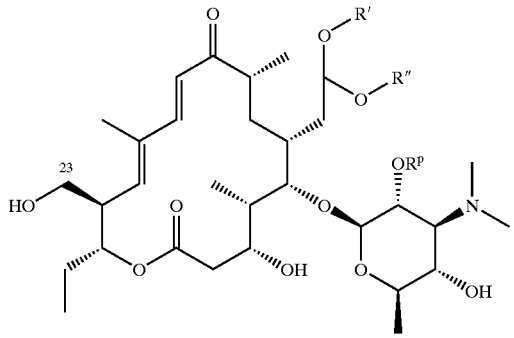

wherein $R^P$ is a hydroxy protecting group and R' and R" are each $C_1$–$C_6$-alkyl or when taken together are —$CH_2CH_2$— or —$CH_2CH_2CH_2$—with an alkylating agent in an aprotic solvent at a temperature between −20° C. and 100° C. in the presence of a base, optionally in the presence of water and a phase transfer catalyst, to provide a compound represented by the formula:

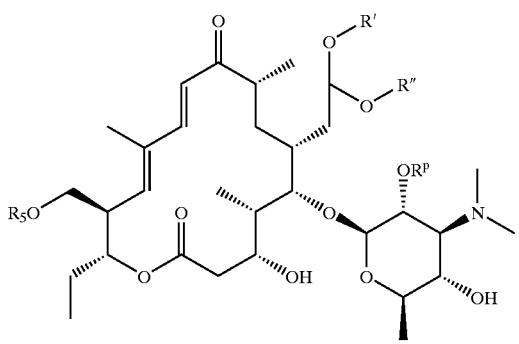

(2) reacting the compound from step (1) with one or more silylating agent(s), optionally with the addition of a catalyst in an aprotic solvent at a temperature between 0° C. and 50° C. for 1 to 48 hours to provide a compound represented by the formula:

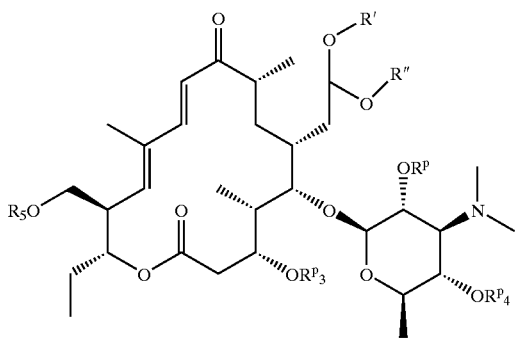

wherein $R^P_3$ and $R^P_4$ are each a hydroxy protecting group;
(3) reacting the compound from step (2) with an acid in an organic solvent at a temperature between −20° C. and 100° C. for 1 to 24 hours to provide a compound represented by the formula:

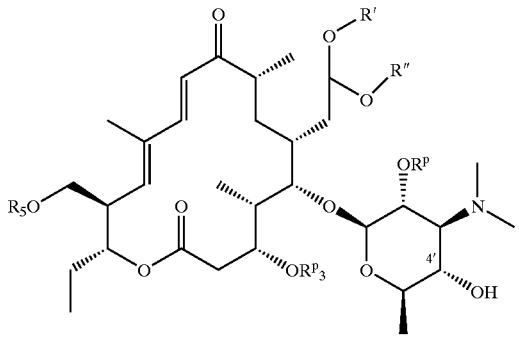

(4) reacting the compound from step (3) with an alkylating agent in an aprotic solvent at a temperature between −20° C. and 100° C. in the presence of a base, optionally in the presence of water and a phase transfer catalyst to provide a compound represented by the formula:

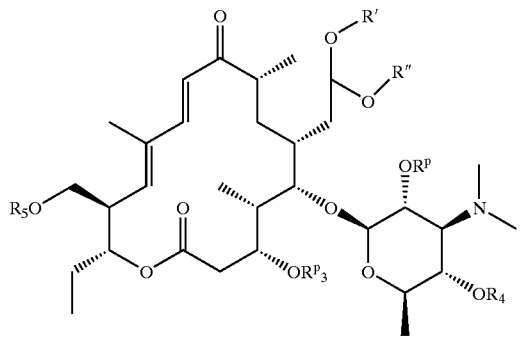

optionally deprotecting the compound from step (4) by:
i. treating with an aqueous acid in an organic solvent at a temperature between 0° C. and 100° C. for 1 to 24 hours; and
ii. stirring in methanol at a temperature between room temperature and reflux temperature for 4 to 24 hours;
to provide a compound represented by Formula I where A is —CHO, $R_1$ and $R_2$ taken together are=O, $R_3$ is hydrogen.

13. A process for the preparation of a compound represented by Formula I as defined in claim 1 comprising:
(1) reacting a compound represented by the formula:

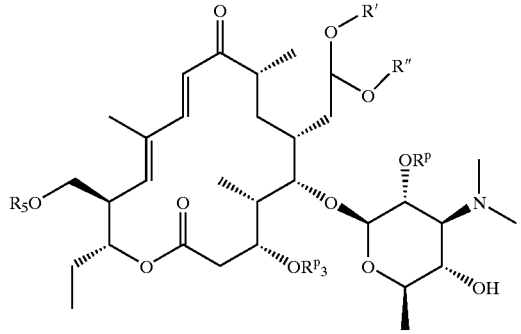

wherein $R_5$ is as defined in claim 1, $R^P$ and $R^P{}_3$ are each a hydroxy protecting group and R' and R" are each $C_1$–$C_6$-alkyl or when taken together are —$CH_2CH_2$— or —$CH_2CH_2CH_2$—,
with $RCHCHCH_2O(CO)O$-t-Butyl in the presence of a palladium catalyst to provide a compound represented by the formula:

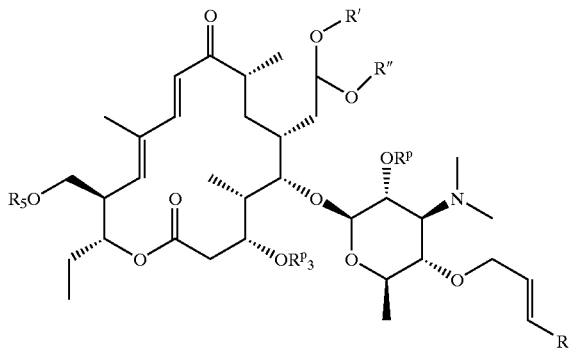

wherein R is hydrogen, aryl, substituted aryl, heteroaryl or substituted heteroaryl, optionally reacting the compound from step (1) with a reducing agent, optionally in the presence of a metal catalyst, or under hydrogenation conditions, to provide a compound represented by the formula:

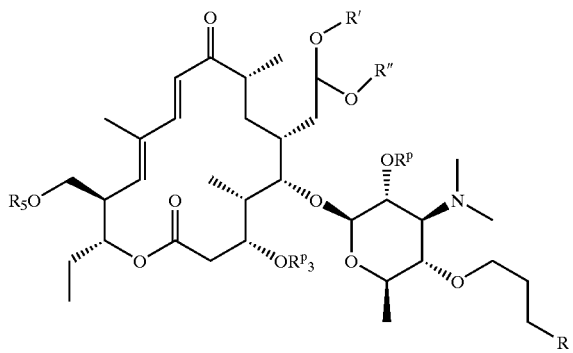

and (2) deprotecting the compound of step (1) by:
i. treating with an aqueous acid in an organic solvent at a temperature from 0° C. to 100° C. for 1 to 24 hours; and
ii. stirring in methanol at a temperature between room temperature and reflux temperature for 4 to 24 hours;

to provide a compound represented by Formula I, wherein $R_4$ is —$(CH_2)_3$—R or —$CH_2(CH)_2$—R, A is —CHO, $R_1$ and $R_2$ taken together are=O, $R_3$ is hydrogen.

14. A process for the preparation of a compound represented by the formula:

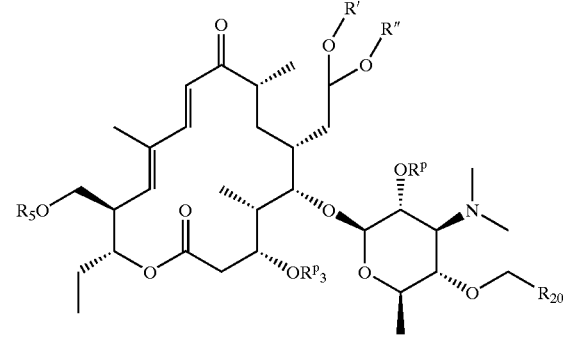

wherein $R^P$ and $R^P{}_3$ are each independently hydrogen or a hydroxy protecting group, $R_{20}$ is selected from CC—R or CH=CH—R, R' and R" are each $C_1$–$C_6$-alkyl or when taken together are —$CH_2CH_2$—or —$CH_2CH_2CH_2$—, R is aryl, substituted aryl, heteroaryl or substituted heteroaryl, comprising:

(1) reacting a compound represented by the formula:

wherein, $R^P$ and $R^P_3$ are hydroxy protecting groups, with an allyl halide or a propargyl halide, optionally reducing the product with a borane or stannane reagent, to give a vinyl borane or vinyl stannane derivative represented by the formula:

where $R_{30}$ is selected from CC—M or CH=CH—M, M is hydrogen, $B(OH)_2$ or $SnBu_3$, and (2) reacting the compound from step (a) with a compound represented by the formula R—X wherein R is as previously defined and X is a halide or triflate, in the presence of a palladium catalyst to give a compound represented by the formula:

15. A compound according to claim 1 which is selected from the group consisting of:

Compound of Formula I: A is —CHO, $R_1$ and $R_2$ taken together are=O, $R_3$ is H, $R_4$ is H, $R_5$ is 4-quinoline-carboxyl and $R^P$ is H;

Compoumd of Formula I; A is —CHO, $R_1$ and $R_2$ taken together are=O, $R_3$ is H, $R_4$ is H, $R_5$ is 3-pyridyl-acetyl and $R^P$ is H;

Compoumd of Formula I: A is —CHO, $R_1$ and $R_2$ taken together are=O, $R_3$ H, $R_4$ is H, $R_5$ is 3-pyridine-propionyl and $R^P$ is H;

Compoumd of Formula I: A is —CHO, $R_1$ and $R_2$ taken together are=O, $R_3$ is H, $R_4$ is H, $R_5$ is 3-pyridine-acrylyl and $R^P$ is H;

Compoumd of Formula I: A is —CHO, $R_1$ and $R_2$ taken together are=O, $R_3$ is H, $R_4$ is H, $R_5$ is $C(O)NH_2$ and $R^P$ is H;

Compoumd of Formula I: A is —CHO, $R_1$ and $R_2$ taken together are=O, $R_3$ is H, $R_4$ is H, $R_5$ is C(O)NHPhenyl and $R^P$ is H;

Compoumd of Formula I: A is —CHO, $R_1$ and $R_2$ taken together are=O, $R_3$ is H, $R_4$ is H, $R_5$ is C(O)NH-p-tolyl and $R^P$ is H;

Compoumd of Formula I: A is —CHO, $R_1$ and $R_2$ taken together are=O, $R_3$ is H, $R_4$ is H, $R_5$ is C(O)NH-4-methylthiophenyl and $R^P$ is H;

Compoumd of Formula I: A is —CHO, $R_1$ and $R_2$ taken together are=O, $R_3$ is H, $R_4$ is H, $R_5$ is C(O)NH-4-methoxyphenyl and $R^P$ is H;

Compoumd of Formula I: A is —CHO, $R_1$ and $R_2$ taken together are=O, $R_3$ is H, $R_4$ is H, $R_5$ is C(O)NH-4-dimethylaminophenyl and $R^P$ is H;

Compoumd of Formula I: A is —CHO, $R_1$ and $R_2$ taken together are=O, $R_3$ is H, $R_4$ is H, $R_5$ is C(O)NH-4-phenoxyphenyl and $R^P$ is H;

Compoumd of Formula I: A is —CHO, $R_1$ and $R_2$ taken together are=O, $R_3$ is H, $R_4$ is H, $R_5$ is C(O)NH-4-cyanophenyl and $R^P$ is H;

Compoumd of Formula I: A is —CHO, $R_1$ and $R_2$ taken together are=O, $R_3$ is H, $R_4$ is H, $R_5$ is C(O)NH-4-nitrophenyl and $R^P$ is H;

Compoumd of Formula I: A is —CHO, $R_1$ and $R_2$ taken together are=O, $R_3$ is H, $R_4$ is H, $R_5$ is C(O)NH-α,α,α-trifluoro-p-tolyl and $R^P$ is H;

Compoumd of Formula I: A is —CHO, $R_1$ and $R_2$ taken together are=O, $R_3$ is H, $R_4$ is H, $R_5$ is C(O)NH-4-fluoro-3-nitrophenyl and $R^P$ is H;

Compoumd of Formula I: A is —CHO, $R_1$ and $R_2$ taken together are=O, $R_3$ is H, $R_4$ is H, $R_5$ is C(O)NH-3,4-difluorophenyl and $R^P$ is H;

Compoumd of Formula I: A is —CHO, $R_1$ and $R_2$ taken together are=O, $R_3$ is H, $R_4$ is H, $R_5$ is C(O)NH-3,5-difluorophenyl and $R^P$ is H;

Compoumd of Formula I: A is —CHO, $R_1$ and $R_2$ taken together are=O, $R_3$ is H, $R_4$ is H, $R_5$ is C(O)NH-4-acetylphenyl and $R^P$ is H;

Compound of formula I: A is —CHO, $R_1$ and $R_2$ taken together are=O, $R_3$ is H, $R_4$ is H, $R_5$ is C(O)NH-(4-fluoro)phenyl and $R^P$ is H;

Compoumd of Formula I: A is —CHO, $R_1$ and $R_2$ taken together are=O, $R_3$ is H, $R_4$ is H, $R_5$ is C(O)NH-(4-chloro)phenyl and $R^P$ is H;

Compoumd of Formula I: A is —CHO, $R_1$ and $R_2$ taken together are=O, $R_3$ is H, $R_4$ is H, $R_5$ is C(O)NH-(4-bromo)phenyl and $R^P$ is H;

Compoumd of Formula I: A is —CHO, $R_1$ and $R_2$ taken together are=O, $R_3$ is H, $R_4$ is H, $R_5$ is C(O)NHCH$_2$Pheny1 and $R^P$ is H;

Compoumd of Formula I: A is —CHO, $R_1$ and $R_2$ taken together are=O, $R_3$ is H, $R_4$ is H, $R_5$ is C(O)NHCH$_2$CH$_2$Phenyl and $R^P$ is H;

Compoumd of Formula I: A is —CHO, $R_1$ and $R_2$ taken together are=O, $R_3$ is H, $R_4$ is H, $R_5$ is C(O)NHCH$_2$CH$_2$Br and $R^P$ is H;

Compoumd of Formula I: A is —CHO, $R_1$ and $R_2$ taken together are=O, $R_3$ is H, $R_4$ is H, $R_5$ is C(O)NHCH$_2$CHCH$_2$ and $R^P$ is H;

Compoumd of Formula I: A is —CHO, $R_1$ and $R_2$ taken together are=O, $R_3$ is H, $R_4$ is H, $R_5$ is C(O)NHCH$_2$CHCH-3-quinolyl and $R^P$ is H;

Compoumd of Formula I: A is —CHO, $R_1$ and $R_2$ taken together are=O, $R_3$ is H, $R_4$ is H, $R_5$ is CH$_2$OCH$_3$ and $R^P$ is H;

Compoumd of Formula I: A is —CHO, $R_1$ and $R_2$ taken together are=O, $R_3$ is H, $R_4$ is H, $R_5$ is CH$_2$OCH$_2$Phenyl and $R^P$ is H;

Compoumd of Formula I: A is —CHO, $R_1$ and $R_2$ taken together are=O, $R_3$ is CH$_2$OCH$_2$Phenyl, $R_4$ is H, $R_5$ is CH$_2$OCH$_2$Phenyl and $R^P$ is H;

Compoumd of Formula I: A is —CHO, $R_1$ and $R_2$ taken together are=O, $R_3$ is H, is H, is CH$_3$ and is H;

Compoumd of Formula I: A is —CHO, $R_1$ and $R_2$ taken together are=O, $R_3$ is H, $R_4$ is H, $R_5$ is CH$_2$CCH and $R^P$ is H;

Compoumd of Formula I: A is —CHO, $R_1$ and $R_2$ taken together are=O, $R_3$ is H, $R_4$ is H, $R_5$ is (CH$_2$)$_4$Br and $R^P$ is H;

Compoumd of Formua I: A is —CHO, $R_1$ and $R_2$ taken together are=O, $R_3$ is H, $R_4$ is H, $R_5$ is CH$_2$CHCHCH$_2$Cl and $R^P$ is H;

Compoumd of formula I: A is —CHO, $R_1$ and $R_2$ taken together are=O, $R_3$ is H, $R_4$ is H, $R_5$ is CH$_2$Phenyl and $R^P$ is H;

Compoumd of Formula I: A is —CHO, $R_1$ and $R_2$ taken together are=O, $R_3$ is H, $R_4$ is H, $R_5$ is CH$_2$CHCH$_2$ and $R^P$ is H Compoumd of Formula I: A is —CHO, $R_1$ and $R_2$ taken together are=O, $R_3$ is CH$_2$CHCH$_2$, $R_4$ is H, $R_5$ is CH$_2$CHCH$_2$ and $R^P$ is H;

Compoumd of Formula I: A is —CHO, $R_1$ and $R_2$ taken together are=O, $R_3$ is H, $R_4$ is H, $R_5$ is CH$_2$CHCH-(3-quinolyl) and $R^P$ is H;

Compoumd of Formula I: A is —CHO, $R_1$ and $R_2$ taken together are=O, $R_3$ is H, $R_4$ is CH$_2$CHCH-(3-quinolyl) and $R^P$ is H;

Compoumd of Formula I: A is —CHO, $R_1$ and $R_2$ taken together are=O, $R_3$ is H, $R_4$ is (t-butoxycarboxy)-3-(3-quinolyl), $R_5$ is CH$_2$-phenyl, and $R^P$ is H;

Compoumd of Formula I: A is —CHO, $R_1$ and $R_2$ taken together are=O, $R_3$ is H, $R_4$ is CH$_2$CHCH$_2$, $R_5$ is H and $R^P$ is H;

Compoumd of Formula I: A is —CHO, $R_1$ and $R_2$ taken together are=O, $R_3$ is H, $R_4$ is CHCHCH$_2$-3-quinolyl, $R_5$ is H and $R^P$ is H;

Compoumd of Formula I: A is —CHO, $R_1$ and $R_2$ taken together are=O, $R_3$ is H, $R_4$ is CHCHCH$_2$-3-quinolyl, $R_5$ is —C(O)NH-Phenyl and $R^P$ is H;

Compoumd of Formula I: A is —CHO, $R_1$ and $R_2$ taken together are=O, $R_3$ is H, $R_4$ is CH$_3$, $R_5$ is H and $R^P$ is H;

Compoumd of Formula I: A is —CHO, $R_1$ and $R_2$ taken together are=O, $R_3$ is H, $R_4$ is CH$_2$-phenyl, $R_5$ is H and $R^P$ is H;

Compoumd of Formula I: A is —CHO, $R_1$ and $R_2$ taken together are=O, $R_3$ is H, $R_4$ is CH$_2$-phenyl, $R_5$ is H and $R^P$ is H;

Compoumd of Formula I: A is —CHO, $R_1$ and $R_2$ taken together are=O, $R_3$ is H, $R_4$ is CH$_2$CCH, $R_5$ is CH$_3$ and $R^P$ is H;

Compoumd of Formula I: A is —CHO, $R_1$ and $R_2$ taken together are=O, $R_3$ is H, $R_4$ is 2-fluoro-3-nitrobenzyl, $R_5$ is CH$_3$ and $R^P$ is H;

Compoumd of Formula I: A is —CHO, $R_1$ and $R_2$ taken together are=O, $R_3$ is H, $R_4$ is (2-pyridyl)thiophenyl, $R_5$ is CH$_3$ and $R^P$ is H;

Compoumd of Formula I: A is —CHO, $R_1$ and $R_2$ taken together are=O, $R_3$ is H, $R_4$ is CH$_2$CC-(3-quinolyl), $R_5$ is CH$_3$ and $R^P$ is H;

Compoumd of Formula I: A is —CHO, $R_1$ and $R_2$ taken together are=O, $R_3$ is H, $R_4$ is CH$_2$CC-(3-pyrimidyl), $R_5$ is CH$_3$ and $R^P$ is H;

Compoumd of Formula I: A is —CHO, $R_1$ and $R_2$ taken together are=O, $R_3$ is H, $R_4$ is CH$_2$CC-(3-pyridinyl), $R_5$ is CH$_3$ and $R^P$ is H;

Compoumd of Formula I: A is —CHO, $R_1$ and $R_2$ taken together are=O, $R_3$ is H, $R_4$ is CH$_2$CHCH-(3-pyrimidinyl), $R_5$ is CH$_3$ and $R^P$ is H; and Compoumd of Formula I: A is —CHO, $R_1$ and $R_2$ taken together are=O, $R_3$ is H, $R_4$ is CH$_2$CH$_2$CH$_2$-(3-pyrimidinyl), $R_5$ is CH$_3$ and $R^P$ is H.

* * * * *

UNITED STATES PATENT AND TRADEMARK OFFICE
CERTIFICATE OF CORRECTION

PATENT NO. : 6,753,415 B2
DATED : June 22, 2004
INVENTOR(S) : Ly Tam Phan et al.

It is certified that error appears in the above-identified patent and that said Letters Patent is hereby corrected as shown below:

Column 63,
Line 47, delete "$R_4$, $R_5$"

Column 67,
Line 65, delete "Compoumd" and insert -- Compound --.

Column 68,
Lines 1, 4, 7, 11, 14 and 17, delete "Compoumd" and insert -- Compound --;
Lines 20, 23, 27, 30, 33, 36, 39, and 42, delete "Compoumd" and insert -- Compound --;
Lines 46, 49, 52, 55, 59, 62 and 65, delete "Compoumd" and insert -- Compound --.

Column 69,
Lines 1, 4, 7, 11, 14, 17, 20 and 23, delete "Compoumd" and insert -- Compound --;
Line 12, delete "$CH_{20}CH_3$" and insert -- $CH_2OCH_3$ --;
Line 21, delete "is H, is $CH_3$ and is H" and insert -- $R_4$ is H, $R_5$ is $CH_3$ and $R^P$ is H --;
Lines 26, 29, 32, 35, 38, 41, 45 and 48, delete "Compoumd" and insert -- Compound --.

Column 70,
Lines 1, 4, 8, 11, 15, 18, 22 and 25, delete "Compoumd" and insert -- Compound --;
Lines 29, 32, 35, 39, 42 and 44, delete "Compoumd" and insert -- Compound --.

Signed and Sealed this

Seventh Day of September, 2004

JON W. DUDAS
*Director of the United States Patent and Trademark Office*